US007128912B2

(12) United States Patent
Höök et al.

(10) Patent No.: US 7,128,912 B2
(45) Date of Patent: Oct. 31, 2006

(54) FIBRONECTIN BINDING PROTEIN COMPOSITIONS AND METHODS OF USE

(75) Inventors: Magnus Höök, Houston, TX (US); Joseph M. Patti, Cumming, GA (US); Karen L. House-Pompeo, Valdosta, GA (US); Pietro Speziale, Pavia (IT); Danny Joh, Houston, TX (US); Martin J. McGavin, Etobicoke (CA)

(73) Assignees: The Texas A&M University System, College Station, TX (US); University Degli Studi di Pavia, Pavia (IT); University of Manitoba, Winnipeg (CA)

( * ) Notice: Subject to any disclaimer, the term of this patent is extended or adjusted under 35 U.S.C. 154(b) by 237 days.

(21) Appl. No.: 10/731,238

(22) Filed: Dec. 10, 2003

(65) Prior Publication Data

US 2005/0123552 A1   Jun. 9, 2005

Related U.S. Application Data

(62) Division of application No. 09/010,317, filed on Jan. 21, 1998, now Pat. No. 6,685,943.

(60) Provisional application No. 60/036,139, filed on Jan. 21, 1997.

(51) Int. Cl.
*A61K 39/00* (2006.01)

(52) U.S. Cl. .............................. 424/185.1; 424/184.1; 424/190.1; 514/12; 514/13; 514/14; 514/15

(58) Field of Classification Search ............. 424/184.1, 424/185.1, 190.1; 514/12, 13, 14, 15
See application file for complete search history.

(56) References Cited

FOREIGN PATENT DOCUMENTS

WO    WO-92/02555    2/1992

OTHER PUBLICATIONS

McGavin et al., "Fibronectin Binding Determinants of the Staphylococcus aureus Fibronectin Receptor" May 5, 1991, vol. 266, No. 13, The Journal of Biological Chemistry USA.

*Primary Examiner*—Robert A. Zeman
(74) *Attorney, Agent, or Firm*—B. Aaron Schulman, Esq.; Stites & Harbison, PLLC

(57) ABSTRACT

Disclosed are antibodies that block the binding of fibronectin protein to fibronectin. Also disclosed are site specifically-mutated and truncated peptide epitopes derived from the fnbA and fnbB genes of *Staphylococcus aureus*, the fnbA and fnbB genes of *Streptococcus dysgalactiae*, and the sfb gene of *Streptococcus pyogenes*, and nucleic acid segments encoding these peptides and epitopes. The anti-(fibronectin binding site) antibodies, peptides and epitopes that give rise to antibodies that block the binding of fibronectin binding proteins to fibronectin, and DNA segments encoding these proteins and are of use in various screening, diagnostic and therapeutic applications including active and passive immunization and methods for the prevention of streptococcal and staphylococcal colonization in animals or humans. These DNA segments and the peptides derived therefrom are proposed to be of use directly in the preparation of vaccines and also for use as carrier proteins in vaccine formulations.

4 Claims, 18 Drawing Sheets

FIG. 1

Figure 2A:
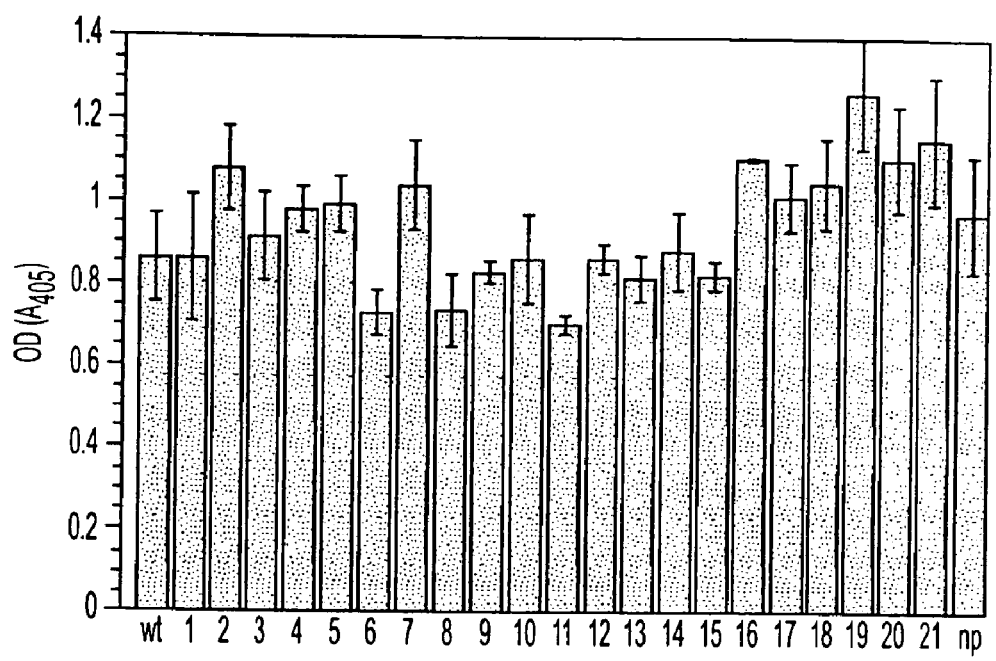

|    |    | DU | D1 | D2 | D3 | D4 |    |
|----|----|----|----|----|----|----|----|

GST—        GST-DU
  GST—      GST-D1
    GST—    GST-D2
      GST—   GST-D3
        GST— GST-D4
  GST——  GST-D12
  GST———  GST-D123
GST—————  GST-DU1234

FIG. 4A

IgG ADDED (μg)

FIBRONECTIN BINDING PROTEIN COMPOSITIONS AND METHODS OF USE

CROSS-REFERENCE TO RELATED APPLICATIONS

The present application is a divisional application of U.S. application Ser. No. 09/010,317, filed Jan. 21, 1998, now U.S. Pat. No. 6,685,943 and claims the benefit of U.S. Provisional Application Ser. No. 60/036,139, filed Jan. 21, 1997.

The present application claims the priority of co-pending U.S. Provisional Patent Application Ser. No. 60/036,139, filed Jan. 21, 1997, the entire disclosure of which is incorporated herein by reference without disclaimer.

The U.S. Government owns rights in the present invention pursuant to Grant AI20624 from the National Institutes of Health.

1. BACKGROUND OF THE INVENTION

1.1. Field of the Invention

The present invention relates generally to the field of molecular biology. More particularly, certain embodiments concern methods and compositions comprising DNA segments and proteins derived from bacterial species. More particularly, the invention provides fnbA nucleic acid and FnBPA amino acid compositions from *Staphylococcus aureus*. Also disclosed are peptide epitopes and protein sequences comprising site-specifically-modified or truncated fibronectin (Fn) binding site domains, and antibodies derived from immunization of animals with these peptide epitopes and binding site domains. Various methods for making and using these antibodies, peptides and DNA segments, peptides and nucleic acid segments encoding modified ligand binding site domains, and native and synthetic proteins are disclosed, such as, for example, the use of antibodies and/or DNA segments as diagnostic probes and templates for protein production, and the use of antibodies, proteins, fusion protein carriers, peptides and nucleic acid segments in various pharmacological and immunological applications.

1.2. Description of the Related Art

1.2.1 MSCRAMMs

Bacterial adherence to host tissue involves specific microbial surface adhesins of which a subfamily termed MSCRAMMs specifically recognize extracellular matrix (ECM) components. Many pathogenic bacteria have been shown to specifically recognize and bind to various components of the extracellular matrix in an interaction which appears to represent a host tissue colonization mechanism. This adherence involves a group of bacterial proteins termed MSCRAMMs (microbial surface components recognizing adhesive matrix molecules) (Patti et al., 1994; Patti and Höök, 1994).

Figure 1:
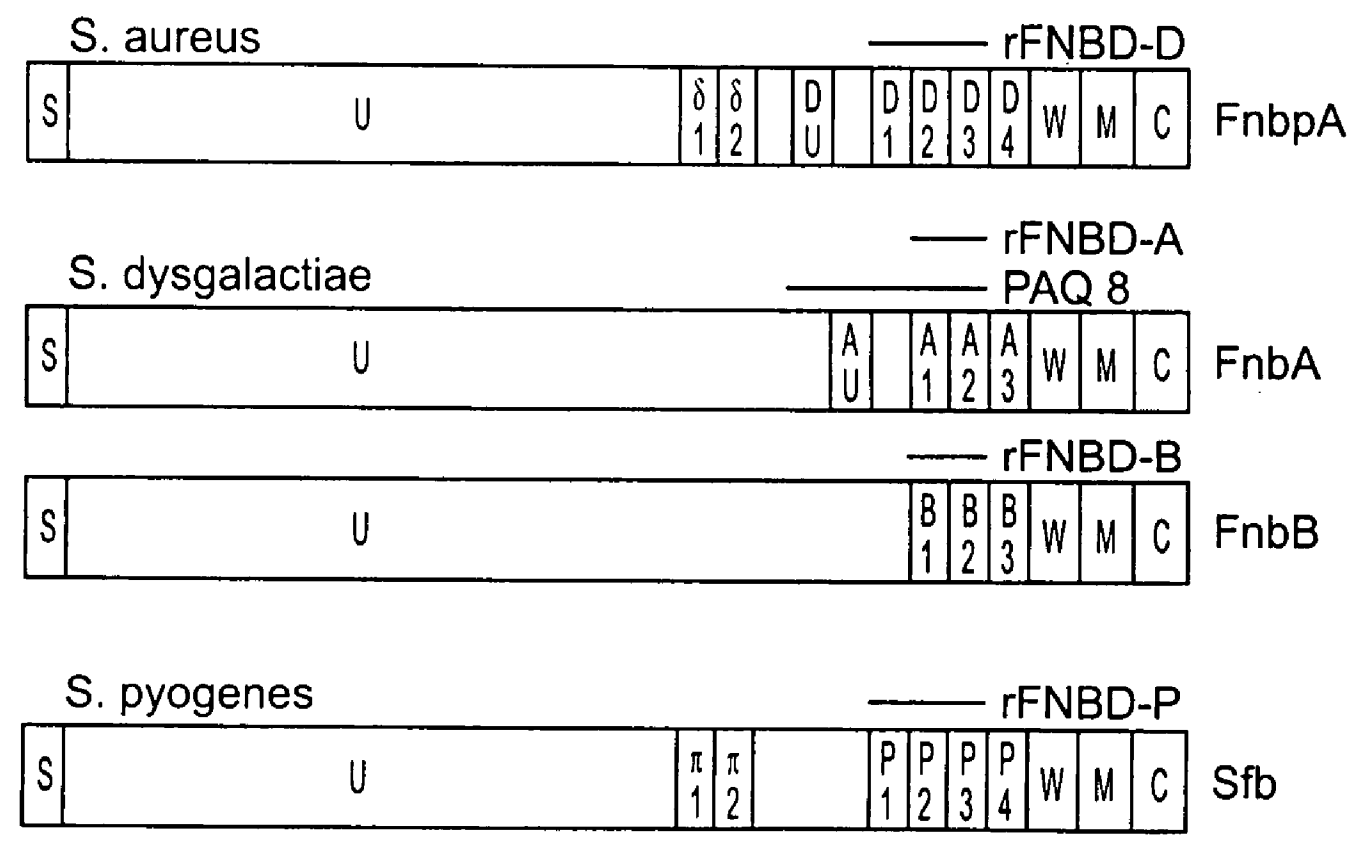

Several Fn binding MSCRAMMs have been isolated and characterized from different Gram-positive bacteria. Genes encoding Fn binding MSCRAMMs from *Staphylococcus aureus* (Signäs et al., 1989), *Streptococcus pyogenes* (Talay et al., 1994; Hansky et al., 1992) and *Streptococcus dysgalactiae* (Lindgren et al., 1993) have been cloned and sequenced. The deduced amino acid sequences revealed 60–100 kDa proteins with very similar structural organization. The N-terminal signal sequence is followed by a long stretch of unique sequence which in some cases is interrupted by two copies of an approximately 30 amino acid long segment. The ligand binding site is located just N-terminal of a proline-rich domain, which is believed to anchor the proteins in the cell wall. This domain is followed by the sequence LPXTGX (SEQ ID NO: 1) which is a cell wall targeting signal (Schneewind et al., 1995), a stretch of hydrophobic residues representing a trans-membrane unit and a short C-terminal cytoplasmic domain containing a cluster of positively charged residues. The primary Fn-binding sites on these MSCRAMMs consist of 30–42 amino acid long motifs repeated 3–4 times, and most of the repeated units contain a consensus sequence (Lindgren et al., 1993; McGavin et al., 1993). This domain is composed of a unit of 37–40 amino acids, repeated three or four times (FIG. 1).

Recombinant proteins corresponding to the repeat regions from the different Fn binding MSCRAMMs are all capable of inhibiting the binding of Fn to different Gram-positive bacteria, including *S. aureus*, *S. dysgalactiae* and *S. pyogenes* (Joh et al., 1994). Furthermore, studies using individual synthetic peptides revealed that a number of the repeat units retain Fn-binding activity, and interfere with binding of Fn by all of the Gram-positive species tested. These data suggest that the binding sites in Fn for the different MSCRAMMs are either overlapping or closely spaced on the matrix protein.

The repeat regions have been overexpressed as recombinant fusion proteins in *Escherichia coli* where the recombinant Fn binding domains (rFnBD) are linked to a stretch of histidine residues which are utilized for affinity purification of the rFnBD proteins. These proteins have been designated as rFnBD-D, rFnBD-A, rFnBD-B, and rFnBD-F, respectively FIG. 1. The rFnBDs were found to exhibit similar binding kinetics and dissociation constants; for example, the dissociation constants of the four recombinant proteins binding to porcine Fn was determined by biosensor analysis to be in the low nM range with the dominant dissociation rates varying between $1 \times 10^{-1}$ and $6 \times 10^{-1} \cdot s^{-1}$. Additionally, the recombinant proteins have been shown to have cross-species specificity and inhibit binding of Fn to many different bacterial cells (Joh et al., 1994).

The repeated units of the Fn binding domains of the different MSCRAMMs are strikingly similar, and appear to contain a consensus sequence (McGavin et al., 1991; House-Pompeo et al., 1996). The repeat units have a high number of acidic residues, and there are conserved hydrophobic and acidic residues at certain positions. Overall there is a high degree of sequence similarity between repeated units in a specific MSCRAMM as well as between MSCRAMMs from different species. Synthetic peptides, analogous to the repeated units, also bind Fn, and by amino acid substitution in these peptides it has been determined that all conserved residues are not needed for Fn binding (McGavin et al., 1991).

Fn is a disulfide-linked dimeric glycoprotein that is found in a soluble form in body fluids and a fibrillar form in the extracellular matrix. The primary biological function of Fn appears to be related to its ability to serve as a substrate for the adhesion of animal cells. This adhesion is mediated by a family of dimeric receptors which recognize and bind to specific sites in the central part of Fn. The primary binding sites in Fn for MSCRAMMs from Gram-positive bacteria has been localized to the Fn $NH_2$-terminal domain (N29) (Mosher and Proctor, 1980; Speziale et al., 1984). This domain is composed of five type I modules which are about 45 amino acids in length. The structure of N29 is a series of anti-parallel β-sheets stabilized by several disulfide bonds interspersed at regular intervals in the sequences (Potts and Campbell, 1994; Venyaminov et al., 1983). The ability to bind Fn is located exclusively within the C-terminal 20 amino acids of each D-motif (Huff et al., 1994; McGavin et al., 1993; McGavin et al., 1991). These amino acids contain the sequence GG(X3,4)(I/V)DF, which is present in repeated motifs of other Fn-binding adhesins, and within the Fn-binding A2 motif of *S. dysgalactiae* FnBA, changes to either of the GG or IDF sequences resulted in loss of Fn-binding (McGavin et al. 1993).

The *S. aureus* Fn-binding MSCRAMM contains an additional ligand binding site in an approximately 30 amino acid long segment which has been designated Du that encompasses the consensus sequence and is located N-terminal of the repeat region. This segment can also interact with Fn and its N-terminal domain (designated N29) (Jönsson, 1992).

*S. aureus* possesses two tandem fnb genes, encoding Fn-binding proteins FnBPA and FnBPB (Jönsson et al., 1991; Signäs et al., 1989), each of which possesses three consecutive 37- or 38 amino acid D-motifs, designated D1, D2, and D3. In tandem, these motifs comprise a high affinity Fn-binding domain, D1–3. Synthetic peptides representing each motif are also individually capable of low affinity Fn-binding, and can competitively inhibit Fn-binding to *S. aureus* (Huff et al., 1994; Signäs et al., 1989).

1.2.2 Attempts to Generate Antibodies that Block Fn Binding have Failed

In all of the Fn-binding MSCRAMMs identified so far, the primary ligand binding sites have been located to domains composed of a 37–42 amino acid motif repeated 3–5 times (McGavin et al., 1993). Unfortunately, attempts to generate blocking antibodies employing both synthetic peptides and different forms of the D1–3 immunogen have been largely unsuccessful (Ciborowski et al., 1992; Rozalska et al., 1994; Speziale et al., 1996). Previous attempts to generate high affinity antibodies that could block *S. aureus* binding to Fn have had little success. For example, when rabbit polyclonal antibodies were generated to both a recombinant form of the *S. aureus* Fn-binding MSCRAMM rFnBD-D and to the Fn-binding synthetic peptide D2, although the titer and specificity of these antisera were good, and the IgG isolated from both immune sera recognized their respective antigens in a Western blot, the isolated IgG from the immune sera did not inhibit the binding of *S. aureus* to Fn.

Interestingly, antibodies purified from mice immunized with a β-D-galactosidase Fn-binding MSCRAMM fusion protein did not block the binding of *S. aureus* to $^{125}$I-Fn (Ciborowski et al., 1992). However, antibodies raised against the β-D-galactosidase Fn-binding MSCRAMM fusion protein that had been treated with formalin possessed moderate blocking activity. These findings suggest that modification of the antigen's protein structure was a critical factor in determining its ability to generate blocking antibodies.

It is possible that the *S. aureus* Fn-binding MSCRAMM interacts with Fn via an "induced fit" binding mechanism. Data supporting the concept of an "induced fit" mechanism of Fn binding by Fn-binding MSCRAMMs has recently been obtained by both immunological (Speziale et al., 1996) and physical biochemical (House-Pompeo et al., 1996) techniques.

A monoclonal antibody 3A10, isolated from a mouse injected with the *S. dysgalactiae* Fn-binding MSCRAMM FnBA, was recently identified and characterized. The epitope for 3A10 was localized to a newly-identified Fn binding motif (designated Au) just upstream of the repeat domain of the primary ligand binding site on FnBA. The antibody 3A10 enhanced Fn binding to Au rather than inhibiting the binding. This effect was demonstrated in two different assay systems. First, 3A10 elevated the ability of the Au-containing proteins and synthetic peptides to compete with bacterial cells for binding to Fn. Secondly, 3A10 dramatically increased the binding of biotin-labeled forms of the Au-containing proteins to the ligand immobilized on a blotting membrane. Purified 3A10 IgG did not recognize the antigen by itself, and Fn was required for the immunological interaction between the antibody and the epitope. This induction effect of Fn was shown in both Western blot and ELISA analyses in which immobilized Au-containing molecules were probed with 3A10 with varying concentrations of Fn. These data and subsequent biophysical studies indicate that the ligand binding sites of FnBA has little or no secondary structure. However, when encountered by Fn, they appear to undergo a structural rearrangement resulting in expression of a ligand-induced binding site (LIBS). The data revealed that 3A10 specifically recognized a LIBS generated by complex formation between Fn and FnBA.

1.3 Deficiencies in the Prior Art

The emerging antibiotic resistance in many bacterial species including *Staphylococcus aureus* and various staphylococcal and streptococcal species is being seen as a potential threat to mankind (Begley, 1994). Particularly worrisome is the multidrug resistance of *Staphylococcus aureus*. Today, almost half of the staphylococcal strains causing nosocomial infections are resistant to all antibiotics except vancomycin and it appears to be only a question of time before vancomycin will become ineffective (Begley, 1994). It is in this scenario that one must consider new strategies in attempts to prevent and treat infection. A detailed knowledge of the molecular pathogenesis of infections caused by staphylococci and streptococci would provide an important base in the design of these strategies. MSCRAMMs mediating microbial adhesion to the host tissues are an attractive target in the development of new antimicrobial agents since it appears to represent a critical first step in the pathogenic process of most infections.

It is clear that while a variety of approaches to the treatment of bacterial diseases have experienced some success, the growing problems of antibiotic resistance, variability of antigens between species and in the same species through mutation of antigens, and the inefficient immune systems in young children, the elderly and other immunocompromised patients, all present difficulties that need to be overcome. Thus, there exists today an immediate need for an effective treatment for streptococcal and staphylococcal pathogens that can be used for a variety of infections in both man and animals.

Burnham and coworkers reported monoclonal antibodies (mAbs) were raised to the native D1–D4 epitope protein sequence (WO 94/18327), however the biological or possible inhibitory activity of these mAbs was not demonstrated.

Interestingly, antibodies purified from mice immunized with a β-galactosidase Fn-binding MSCRAMM fusion protein did not block the binding of *S. aureus* to $^{125}$I-Fn (Ciborowski et al., 1992). However, antibodies raised against the β-galactosidase Fn-binding MSCRAMM fusion protein that had been treated with formalin possessed moderate blocking activity. These findings suggest that modification of the antigen's protein structure was a factor in determining its ability to generate blocking antibodies. Formalin treatment is a general method of inactivating proteins by inducing Schiff bases in lysine residues. However, the reaction is reversible and the molecule can potentially regain functionality, and therefore negate the beneficial effects of such formalin treatment.

There are several possible reasons for these results, e.g., when an active Fn-binding MSCRAMM is injected into an animal, one may assume that the bacterial protein immediately complexes with Fn. In such a complex, the surface of the MSCRAMM representing the binding site will be occupied and not available for immunological recognition. If this argument is correct, it would represent a clever previously unknown strategy used by microbes to avoid host defense mechanisms.

The fact that it has not been possible to generate blocking antibodies to the native Fn binding proteins has precluded their use in active and passive immunization methods directed toward preventing bacterial infection. Therefore, the creation of site-specifically-modified epitopes in the Fn-binding MSCRAMMs which would lead to the creation of antigens that generate high-affinity blocking antibodies would represent a significant breakthrough in the field of infectious disease, and in particular, revolutionize the manner in which staphylococcal and streptococcal diseases are treated, thereby obviating the need for antibiotic therapies to treat bacterial infection. Likewise, the development of mAb groups which recognize multiple Fn-binding epitopes from a single FnBP would facilitate methods for inhibiting Fn binding to FnBPs using monoclonal antibodies. Methods of altering DNA sequences encoding peptide epitopes would provide a stable, reproducible means for incorporating changes in the peptide sequence, and therefore represent a superior advancement over current formalin denaturation of native proteins. The development of methods of inhibiting bacterial adhesion to host cells by inhibiting ECM component interactions with bacterial cell surface proteins would provide a marked improvement in the state of the art for treatment of such infections.

2. SUMMARY OF THE INVENTION

The present invention overcomes one or more of these and other drawbacks inherent in the prior art by providing novel compositions and methods for their use, for example in the treatment of bacterial infection and the prevention of bacterial adhesion using non-antibiotic strategies. The present invention provides, for the first time, antibodies that block the binding of fibronectin to fibronectin binding proteins. These antibodies are raised against peptides that, while based upon epitopes from the fibronectin binding domain of fibronectin binding proteins, do not bind to fibronectin. Thus, once introduced into an animal, these peptide epitopes do not form a complex with fibronectin. This allows antibodies to be made against the uncomplexed peptide epitope, which antibodies inhibit or block the binding of fibronectin to fibronectin binding proteins.

Disclosed are antibodies that inhibit or block the binding of a fibronectin binding protein to fibronectin, and peptide compositions that, upon immunization into a selected animal, produce such antibodies. Also disclosed are methods for the use of the novel peptide and antibody compositions in the treatment of microbial infections mediated by the inhibition of microbial binding to the host cell ECM component, Fn. Also disclosed are methods for active and passive immunization against microbial pathogens, such as streptococcal and staphylococcal pathogens, exemplified using peptide epitopes from the fibronectin binding domain of selected fibronectin binding proteins. Particular aspects of the invention relate to novel nucleic acid segments encoding these epitopes, and methods for the use of such nucleic acid segments in a variety of diagnostic and therapeutic regimens.

The invention first provides a composition comprising an antibody that binds to a fibronectin binding domain of a fibronectin binding protein and inhibits binding of the fibronectin binding protein to fibronectin. Thus in particular embodiments, these antibodies are referred to as blocking antibodies. In preferred aspects of the invention, the antibody binds to a peptide or epitope of the fibronectin binding domain that, when the peptide is not an integral part of the fibronectin binding domain, does not specifically bind to fibronectin. That is to say, in certain preferred aspects, the peptide itself, in isolation, does not bind to fibronectin.

In particular embodiments, the antibody binds to a fibronectin binding domain of a microbial fibronectin binding protein, preferably a streptococcal or a staphylococcal fibronectin binding protein. In other preferred aspects, the antibody binds to a fibronectin binding domain of a streptococcal Sfb, FnBA or FnBB or staphylococcal FnBPA or FnBPB fibronectin binding protein. In still other preferred aspects, the antibody binds to a fibronectin binding domain of a fibronectin binding protein expressed from a staphylococcal fnbA gene, particularly the fnbA gene of *Staphylococcus aureus*.

Both polyclonal antibodies and monoclonal antibodies that inhibit the binding of fibronectin binding proteins to fibronectin are provided herein. Preferred are antibodies that bind to the same epitope as monoclonal antibody 9C3 or 11A5, including the monoclonal antibodies 9C3 or 11A5 themselves.

In certain embodiments, the antibody is linked to a detectable label, such as, but not limited to, a radioactive label, a fluorogenic label, a nuclear magnetic spin resonance label, biotin, avidin or an enzyme that generates a colored product upon contact with a chromogenic substrate, including, but not limited to, alkaline phosphatase, hydrogen peroxidase or glucose oxidase enzyme.

In certain aspects of the present invention, the antibody composition is dispersed in a pharmaceutically acceptable excipient or medium.

The invention further provides a composition comprising an isolated peptide of a fibronectin binding domain of a fibronectin binding protein, wherein the peptide does not bind to fibronectin. As used herein in regard to the instant isolated peptide compositions, the term "of a fibronectin binding domain of a fibronectin binding protein" will be understood to mean that the isolated peptide is sufficiently similar to a portion of the wild-type sequence of the fibronectin binding domain of the fibronectin binding protein to allow the generation of an antibody that binds both to the isolated peptide and the fibronectin binding domain. Included within this description are isolated peptides wherein the sequence of the isolated peptide is or has been mutated, or is different enough to prevent binding of the isolated peptide to fibronectin.

Thus isolated peptide fragments from wild-type or naturally occurring variants and synthetic or recombinant peptides corresponding to wild-type, naturally occurring variants or introduced mutations that do not correspond to a naturally occurring fibronectin binding domain of a fibronectin binding protein are encompassed in the present invention. In preferred aspects, the isolated peptide comprises at least a first mutation as compared to the corresponding amino acid sequence from a wild type fibronectin binding domain. In yet other embodiments, the isolated peptide has been engineered to comprise the mutation.

Included within the term "engineered" are mutations introduced into the peptide, for example through peptide synthesis or site-directed mutagenesis.

The isolated peptides only need be of a sufficient length to allow for the generation of an antibody that binds both to the isolated peptide and the fibronectin binding domain, and blocks the binding of the fibronectin binding protein to fibronectin. In certain aspects, peptides comprising at least about 5, about 6, about 7, about 8, about 9, about 10, about 11, about 12, about 13, about 14, about 15, about 16, about 17, about 18, about 19, about 20, about 22, about 24, about 25, about 30, about 35, about 40, about 45 or about 50 contiguous amino acids are preferred. In other preferred aspects of the invention, the isolated peptide comprises at least about 6 contiguous amino acids from the wild type sequence of the fibronectin binding domain. In more preferred embodiments, the isolated peptide comprises a contiguous amino acid sequence of at least about 8 amino acids from SEQ ID NO:60 or SEQ ID NO:61. In still more preferred aspects, the isolated peptide comprises the contiguous amino acid sequence of SEQ ID NO:60 or SEQ ID NO:61.

In aspects of the invention, the isolated peptide compositions are used to generate an immunological response in an animal. In these aspects, the compositions preferably further comprise an adjuvant. Furthermore, in these aspects of the invention, the isolated peptide composition is preferably dispersed in a pharmaceutically acceptable excipient.

In particular embodiments of the present invention, the isolated peptide is operatively linked to a selected amino acid sequence. Thus the invention provides compositions comprising a fusion protein comprising at least a first peptide of a fibronectin binding domain of fibronectin binding protein operatively linked to a selected amino acid sequence, wherein the first peptide does not specifically bind to fibronectin. In preferred aspects, the first peptide is operatively linked to a selected carrier molecule or amino acid sequence, including, but not limited to, keyhole limpet hemocyanin (KLH) and bovine serum albumin (BSA).

Further provided is a composition comprising an isolated nucleic acid segment that encodes a peptide of a fibronectin binding domain of a fibronectin binding protein, wherein the peptide does not specifically bind to fibronectin.

The invention also provides a pharmaceutical composition comprising, in a pharmaceutically acceptable excipient, an effective amount of an antibody that binds to a fibronectin binding domain of a fibronectin binding protein and inhibits binding of the fibronectin binding protein to fibronectin, an isolated peptide of a fibronectin binding domain of a fibronectin binding protein, wherein the peptide does not specifically bind to fibronectin, or an isolated nucleic acid segment that encodes a peptide of a fibronectin binding domain of a fibronectin binding protein, wherein the peptide does not specifically bind to fibronectin.

The compositions of the present invention are contemplated for use in the preparation of an immunizing formulation. Thus, the invention provides for the use of the instant compositions in the preparation of an immunizing formulation.

The present invention also contemplates the use of the compositions provided herein in the preparation of a medicament for the prevention or treatment of an infection in an animal, or in the preparation of a formulation that inhibits the binding of microorganisms to fibronectin. Thus the invention also provides for the use of the instant compositions in the preparation of a medicament for preventing or treating an infection or in the preparation of a formulation that inhibits the binding of microorganisms to fibronectin.

The present invention further provides a method of identifying a peptide of a fibronectin binding domain of a fibronectin binding protein that does bind to fibronectin, comprising contacting a candidate peptide with fibronectin under conditions effective to allow binding of fibronectin to the fibronectin binding domain of a fibronectin binding protein, and identifying a positive candidate peptide that does not bind to fibronectin.

Also provided is a method of generating an antibody that binds to a fibronectin binding domain of a fibronectin binding protein and inhibits binding of the fibronectin binding protein to fibronectin, comprising administering to an animal a pharmaceutical composition comprising an immunologically effective amount of an isolated peptide of a fibronectin binding domain of a fibronectin binding protein, wherein the peptide does not specifically bind to fibronectin.

In certain aspects of the invention, the pharmaceutical composition is prepared by contacting a candidate peptide with fibronectin under effective binding conditions, and identifying a positive candidate peptide that does not bind to fibronectin and dispersing the positive candidate peptide in a pharmaceutically acceptable diluent. In preferred aspects, a plurality of candidate peptides are contacted with fibronectin under effective binding conditions, and one or more positive candidate peptide(s) that do not bind to fibronectin are identified. The plurality of candidate peptides can be generated by mutagenizing a plurality of peptides, exemplified by, but not limited to, replacing each residue of a selected peptide with proline residues, or in other embodiments by fractionating or fragmenting a native or naturally occurring fibronectin binding domain of a fibronectin binding protein, for example by digesting the fibronectin binding domain with a selected protease. The positive candidate peptides thus identified can be, in certain aspects of the invention, linked to a carrier protein and/or admixed with an adjuvant, or dispersed in a pharmaceutically acceptable medium or excipient.

In yet other aspects, the pharmaceutical composition comprises an immunologically effective amount of a peptide having the amino acid sequence of SEQ ID NO:60 or SEQ ID NO:61. In certain preferred embodiments, the pharmaceutical composition is designed for administration to an animal that has, is suspected of having, or is at risk of developing a microbial infection.

The invention additionally provides a method for detecting a fibronectin binding protein in a sample, comprising contacting a sample suspected of containing a fibronectin binding protein with an antibody that binds to a fibronectin binding domain of a fibronectin binding protein and inhibits binding of the fibronectin binding protein to fibronectin, under conditions effective to allow the formation of immune complexes, and detecting the immune complexes so formed.

In particular embodiments of the invention, the fibronectin binding protein is expressed by a microorganism, exemplified by, but not limited to, a *streptococcus* or a *staphylococcus*, and the sample is suspected of containing the microorganism. In certain preferred aspects, the fibronectin binding protein is expressed by *Staphylococcus aureus*. As the fibronectin binding proteins expressed by microorganisms localizes to the cell surface, in preferred aspects the fibronectin binding proteins are detected on or at the surface of the microbial cells.

Also provided are kits comprising, in suitable container means, an antibody that binds to a fibronectin binding domain of a fibronectin binding protein and inhibits binding of the fibronectin binding protein to fibronectin, an isolated peptide of a fibronectin binding domain of a fibronectin binding protein, wherein the peptide does not specifically bind to fibronectin, or an isolated nucleic acid segment that encodes a peptide of a fibronectin binding domain of a fibronectin binding protein, wherein the peptide does not specifically bind to fibronectin.

In certain embodiments of the present invention, the kits comprise, in suitable container means, a first antibody that binds to a fibronectin binding domain of a fibronectin binding protein and inhibits binding of the fibronectin binding protein to fibronectin. Thus in certain aspects, the invention provides immunodetection kits. In particular aspects, the immunodetection kits further comprise an immunodetection reagent, such as a detectable label that is linked to the first antibody. In other preferred aspects, the immunodetection kits further comprise a second antibody that binds to the first antibody.

Also provided are therapeutic kits, which comprise, in suitable container means, a therapeutically effective amount of the antibody, the isolated peptide or the isolated nucleic acid segment is comprised in a pharmaceutically acceptable formulation. In preferred embodiments of the instant therapeutic kits, the antibody inhibits the binding of streptococci or staphylococci to fibronectin. In yet other preferred aspects, the pharmaceutically-acceptable formulation is suitable for topical, parenteral or oral administration.

The invention further provides a method of preventing or treating a microbial infection in an animal, comprising administering to the animal a therapeutically effective amount of a pharmaceutical composition comprising, an antibody that binds to a fibronectin binding domain of a fibronectin binding protein and inhibits binding of the fibronectin binding protein to fibronectin, an isolated peptide of a fibronectin binding domain of a fibronectin binding protein, wherein the peptide does not specifically bind to fibronectin, or an isolated nucleic acid segment that encodes a peptide of a fibronectin binding domain of a fibronectin binding protein, wherein the peptide does not specifically bind to fibronectin, wherein the pharmaceutical composition prevents or inhibits microbial infection in the animal. As used herein, the term "therapeutically effective amount" will be understood as an amount effective to inhibit the binding of the fibronectin binding protein of the microbe to the fibronectin of the animal. In preferred aspects of the present invention, the method prevents, inhibits or treats streptococcal or staphylococcal infection or colonization in the animal or human subject.

3. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1. Domain organization of Fn receptors from *Staphylococcus aureus, Streptococcus dysgalactiae*, and *Streptococcus pyogenes*. Fn-binding repeats are represented by A, B, D, and P. S, signal sequences; U, sequence unique to the Fn receptor; W, cell-wall spanning region M, membrane-spanning region; C, intracellular sequence. The recombinant proteins correspond to the regions indicated by rFNBD-D, rFNBD-A, PAQ8, rFNBD-B, and rFNBD-P. Au and DU regions represent novel ligand binding sites identified by the present inventors.

Figure 2B:
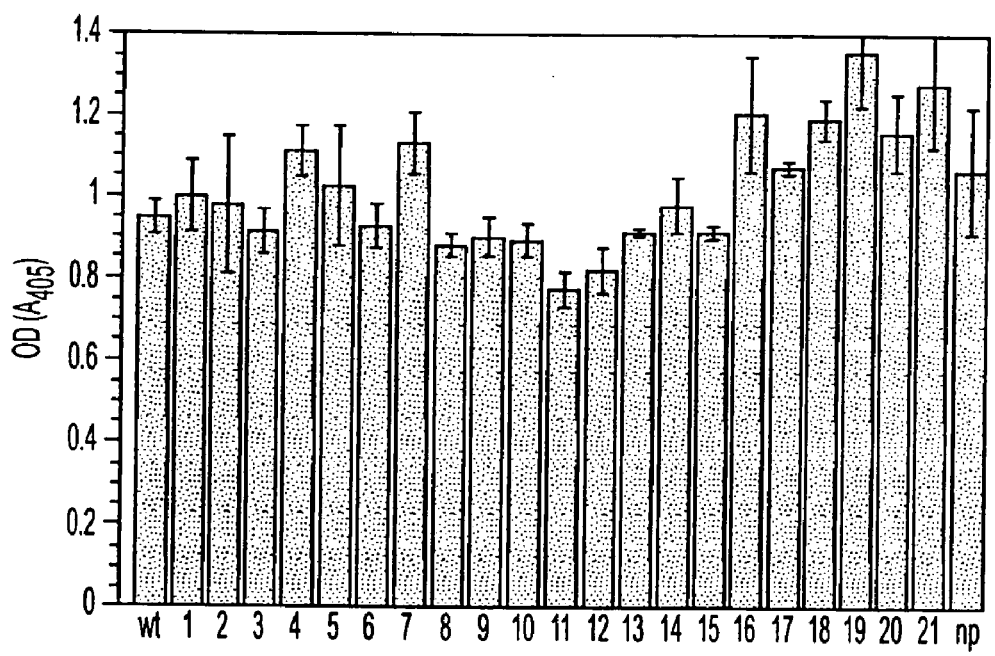
Figure 2C:
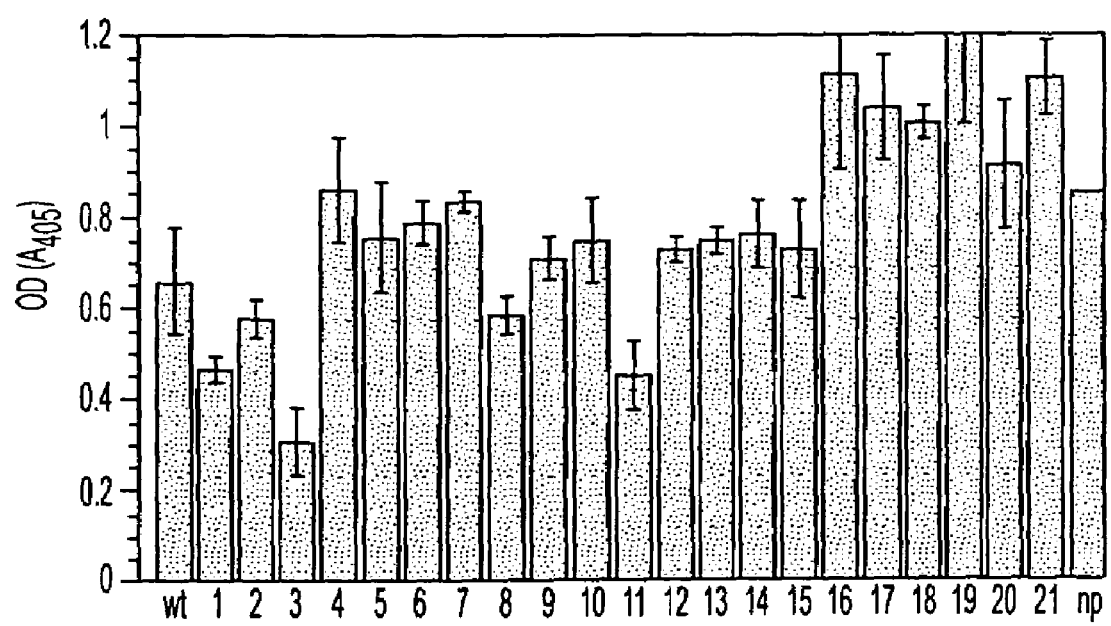

FIG. 2A, FIG. 2B and FIG. 2C. Inhibition of *S. aureus* binding to immobilized fibronectin by wild-type and mutant D3 peptides 1 through 21 (Table 3). NP indicates the amount of adherent bacteria in the absence of inhibitor. FIG. 2A. Peptides tested at 5 μg/well. FIG. 2B. Peptides tested at 50 μg/well. FIG. 2C. Peptides tested at 250 μg/well.

Figure 3A:
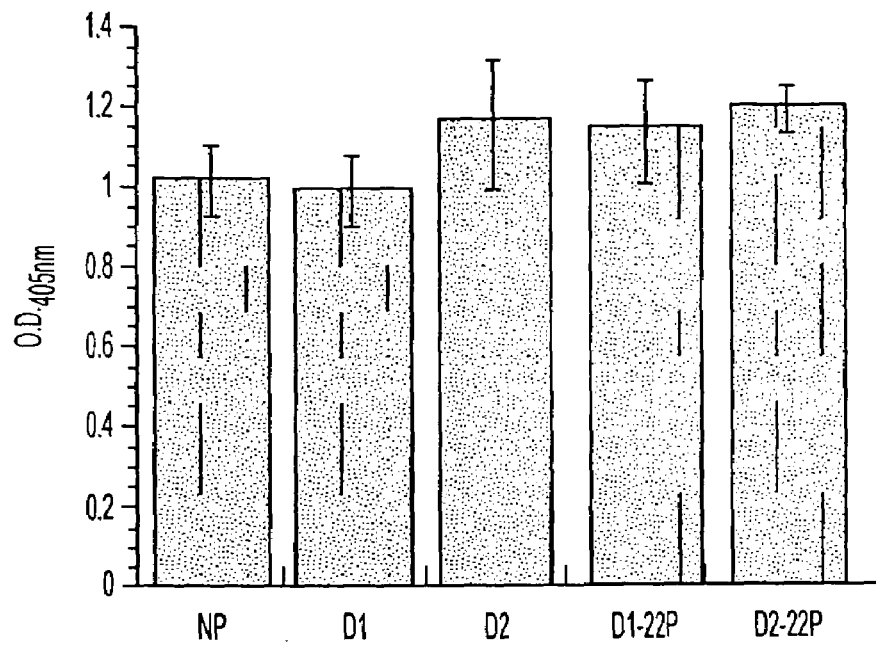
Figure 3B:
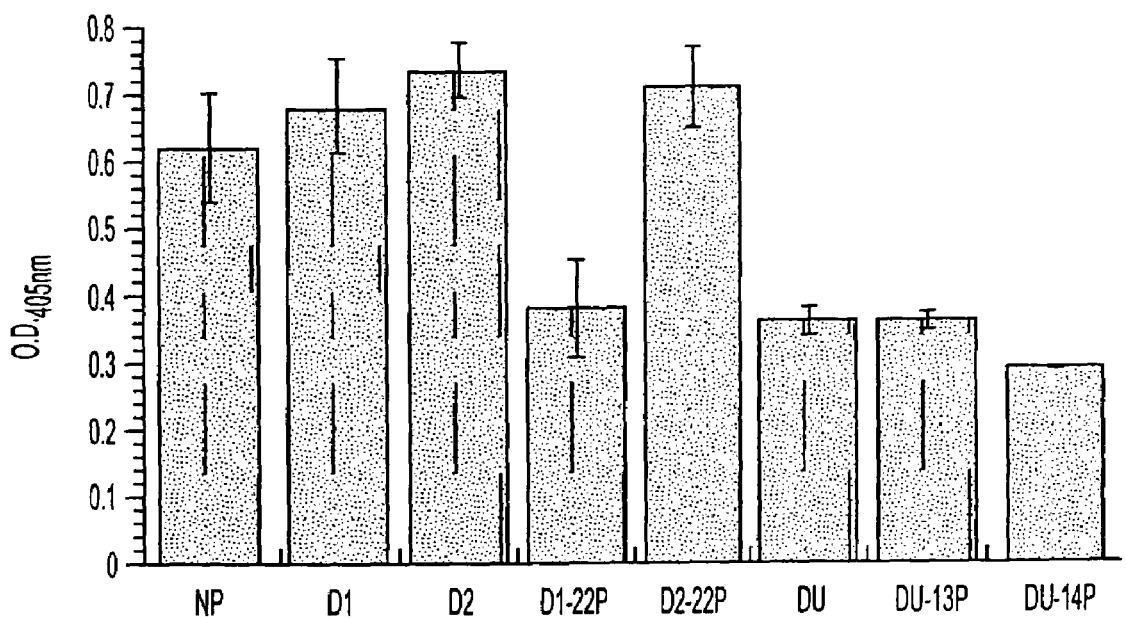

FIG. 3A and FIG. 3B. FIG. 3A. Inhibition of *S. aureus* binding to immobilized fibronectin by wild-type peptides D1 and D2 and mutant derivatives. NP indicates the amount of adherent bacteria in the absence of inhibitor. All peptides were tested at 10 μg/well. FIG. 3B. Inhibition of *S. aureus* binding to immobilized fibronectin by wild-type peptides D1. D2 and DU and mutant derivatives. NP indicates the amount of adherent bacteria in the absence of inhibitor. All peptides were tested at 250 μg/well.

Figure 4B:
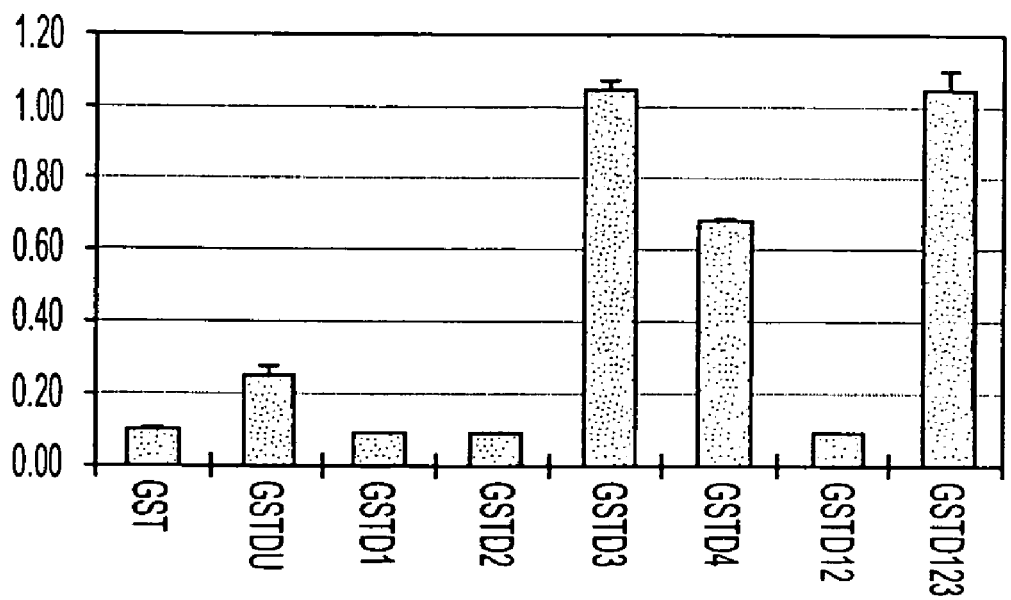
Figure 4C:
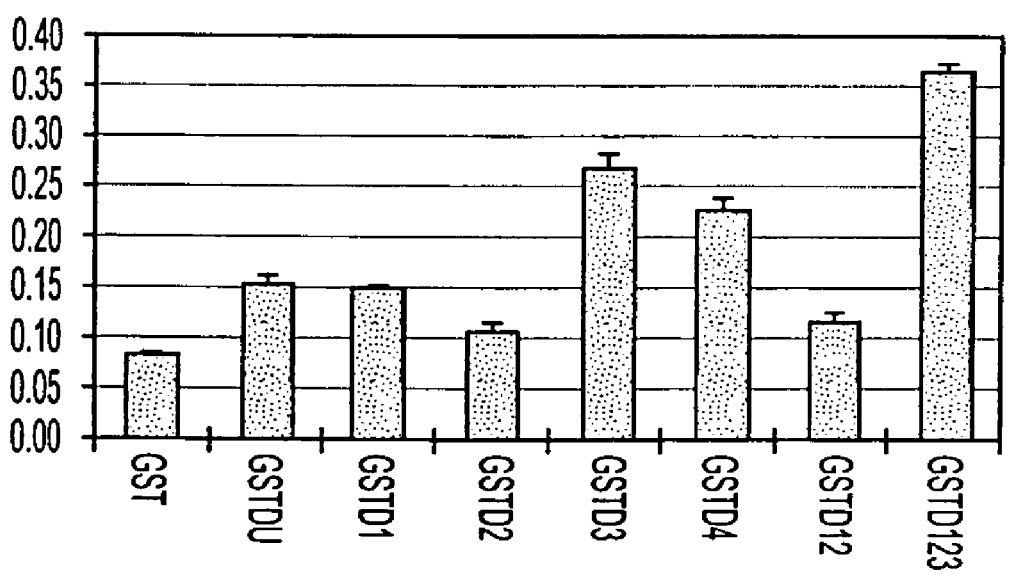

FIG. 4A, FIG. 4B and FIG. 4C. FIG. 4A. Glutathione S transferase fusion proteins containing segments of the *S. aureus* FnBPA. FIG. 4B. Localization of the epitopes for anti-D3pep antibodies. FIG. 4C. Localization of the epitopes for anti-Fn-peps antibodies.

Figure 5A:
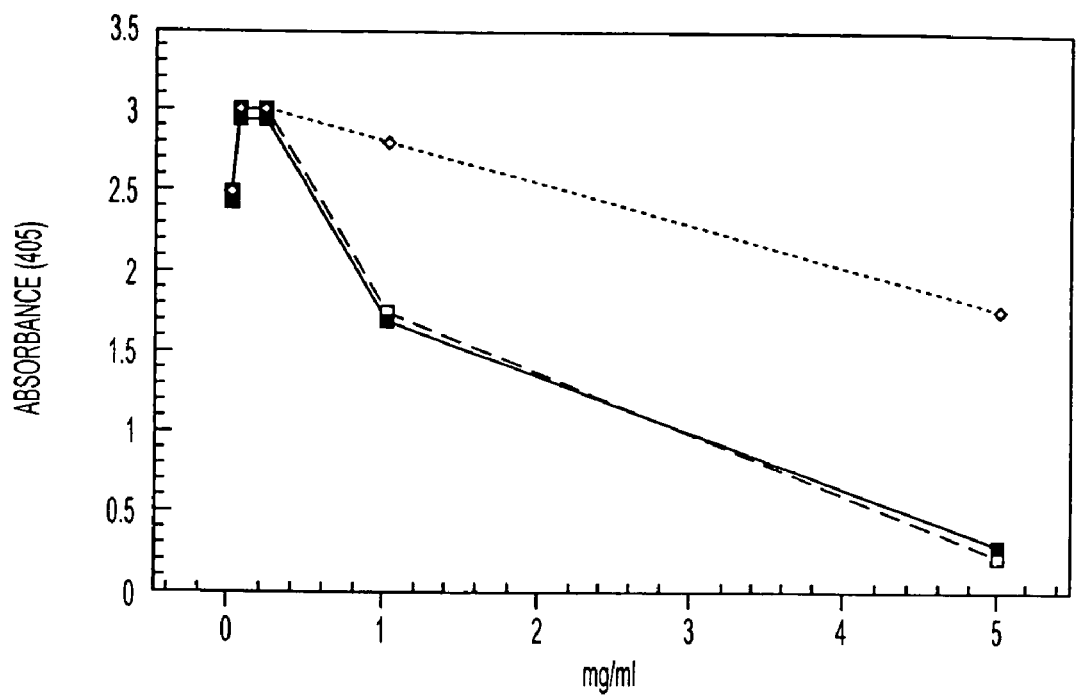
Figure 5B:
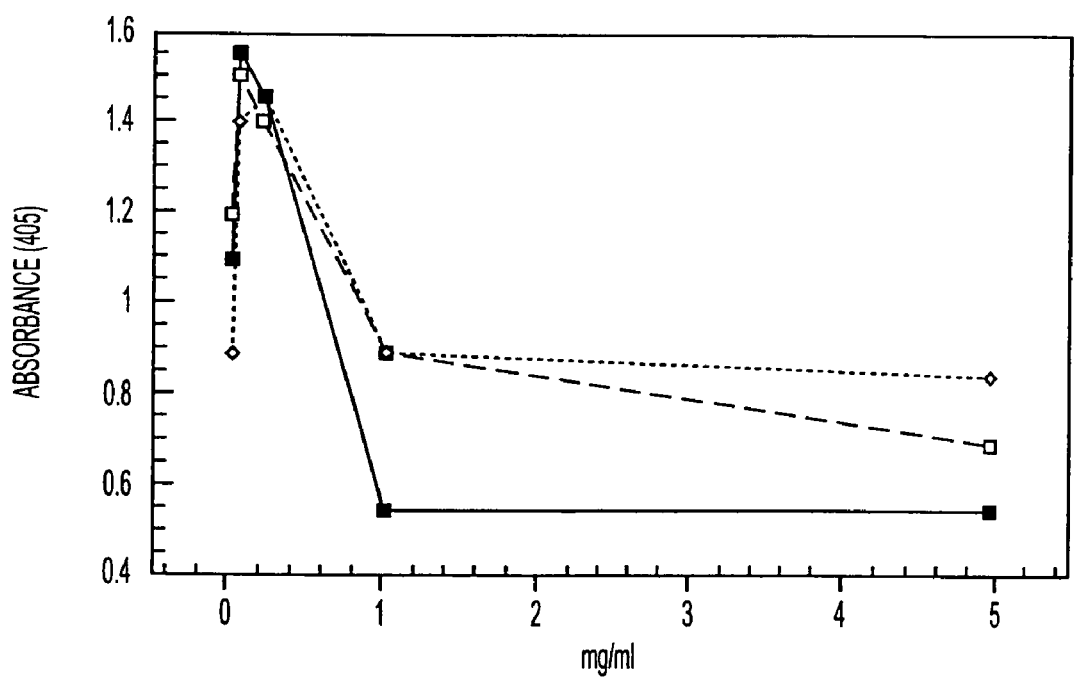

FIG. 5A and FIG. 5B. Inhibitory activity of anti-D3pep (□) and anti-Fn-peps (■) antibodies versus preimmune IgG (○). FIG. 5A. Shown is the binding of GST-D3 to immobilized Fn. FIG. 5B. Shown is the binding of GST-D 123 (GSTD1–3) to Fn.

Figure 6:
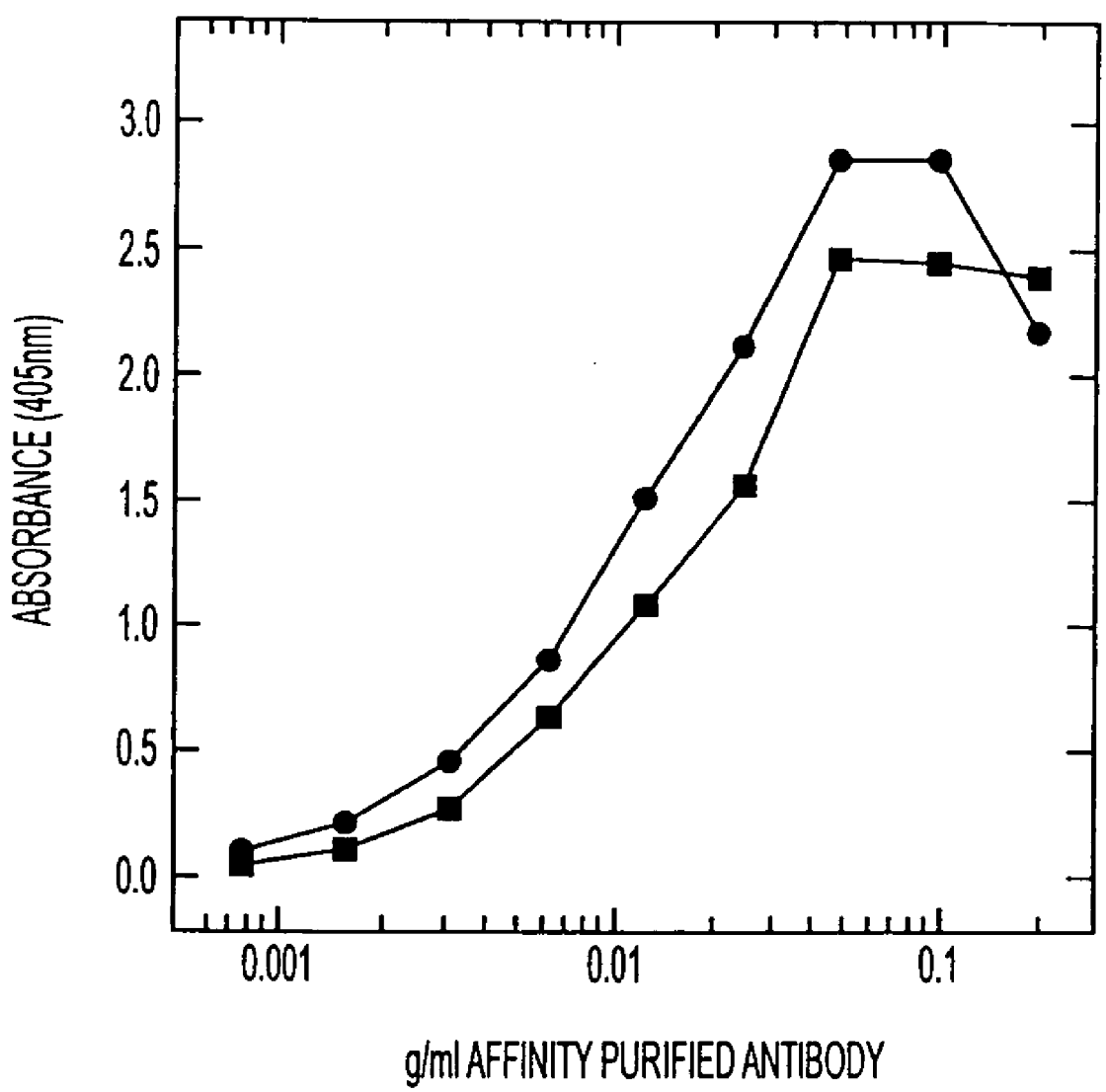

FIG. 6. Titration of affinity purified antibodies obtained by immunizing with D 1–3 (●), or GSTD 1–3 (■). Microtiter plates were coated with 1 μg/ml D 1–3, and incubated with the indicated concentrations of affinity purified antibodies.

Figure 7:
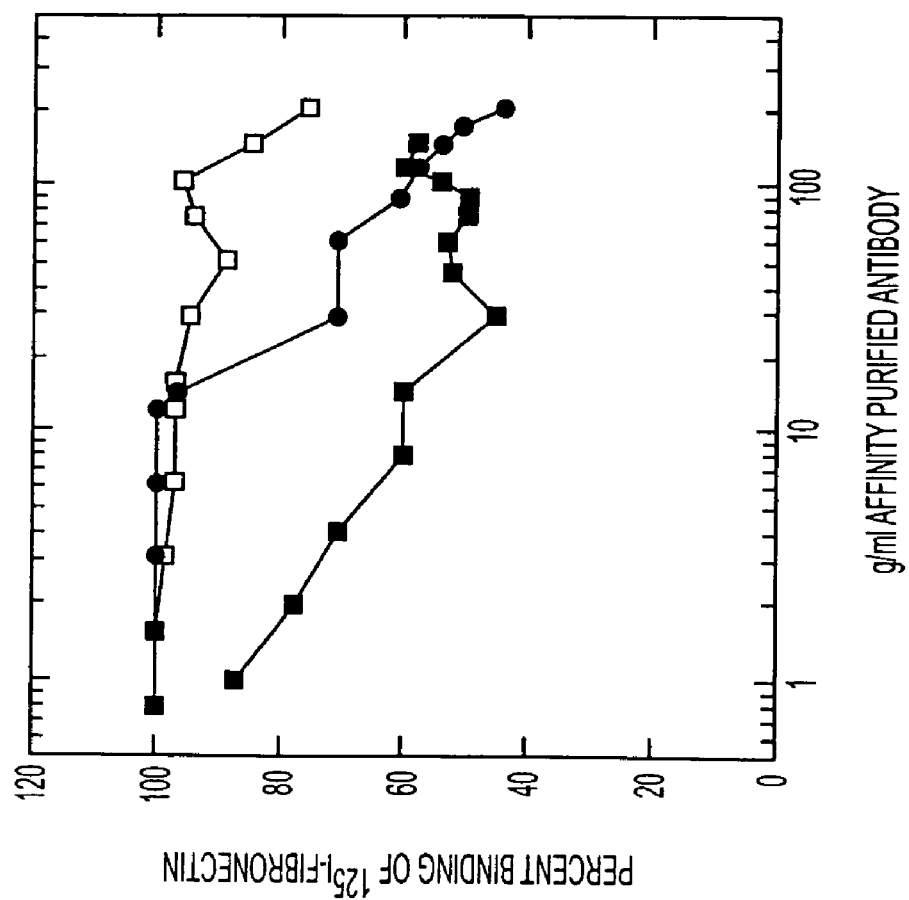

FIG. 7. Inhibition of $^{125}$I-Fn binding to *S. aureus* L857 cells by pre-immune antibodies (□), or affinity purified antibodies obtained by immunizing with GSTD1–3 (■), or D1–3 (●). Results are expressed as the percentage of $^{125}$I-Fn bound in the absence of added antibody. Each point represents the average of duplicate determinations.

Figure 8B:
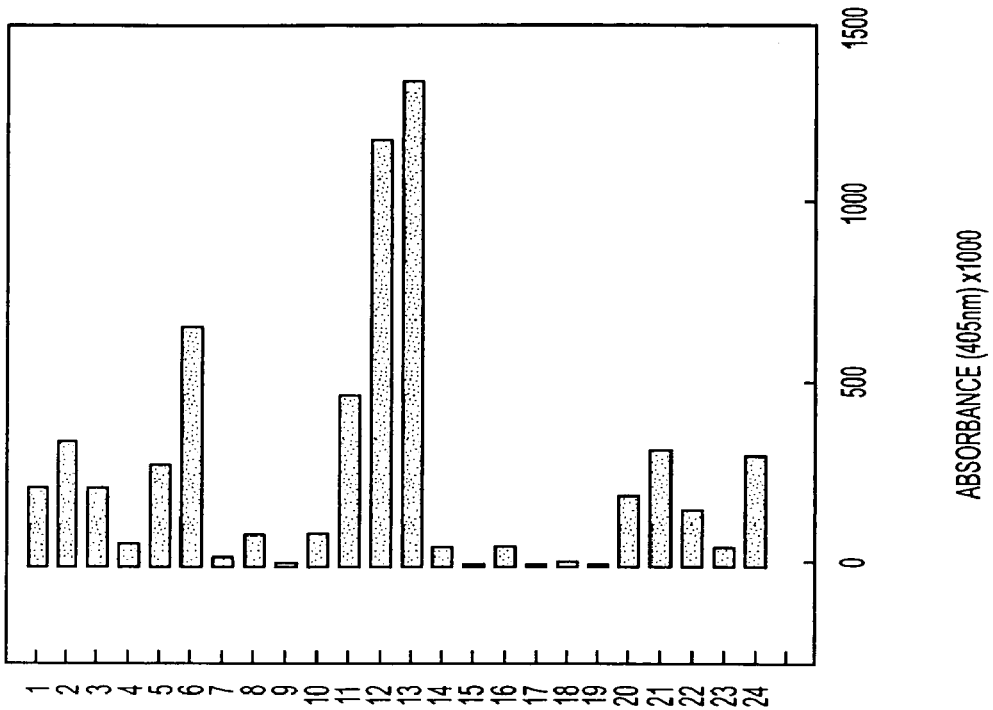
Figure 8A:
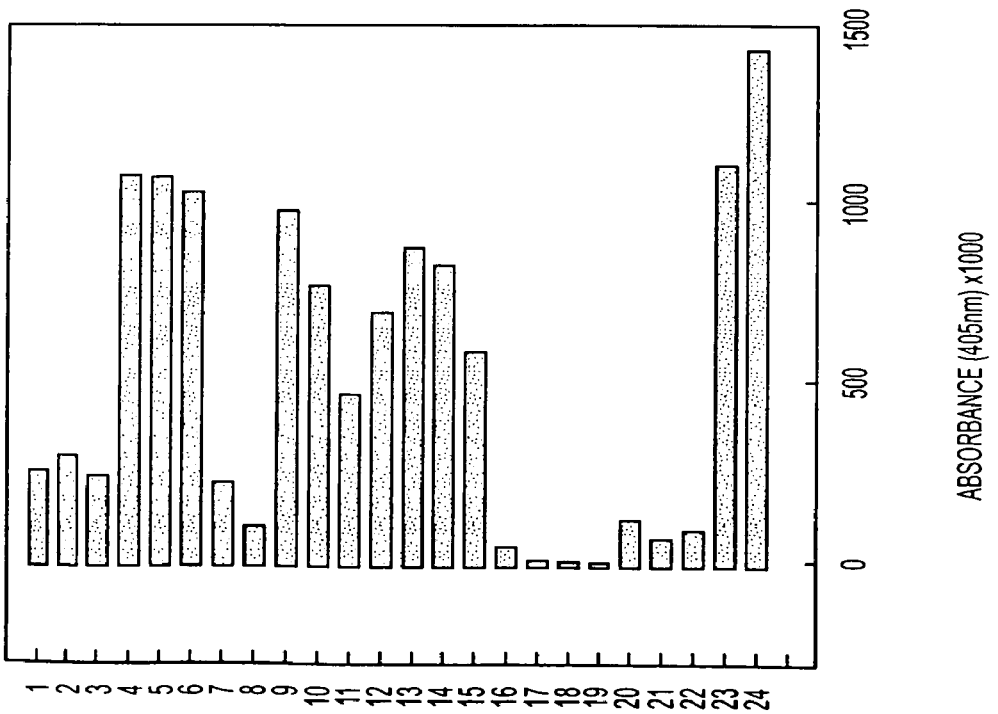

FIG. 8A and FIG. 8B. Epitope mapping of affinity purified antibodies obtained by immunizing with D1–3 (FIG. 5A), or GSTD1–3 (FIG. 8B). Peptide sequences are listed in Table 9 in descending order from the N-terminus of D1, and ending with EEDTEKDKPK (peptide #24; SEQ ID NO:2), in which the C-terminus represents residue 18 of the D2 motif. D1 or D2 designation in Table 9 indicates the span of peptides in which one or more amino acids are contributed by either of the D1 or D2 motifs. Biotinylated peptides were captured in wells of streptavidin coated microtiter plates and incubated for 60 minutes with 100 μl aliquots of 50 ng/ml affinity purified antibody. Each value represents the average of triplicate determinations.

Figure 9A:
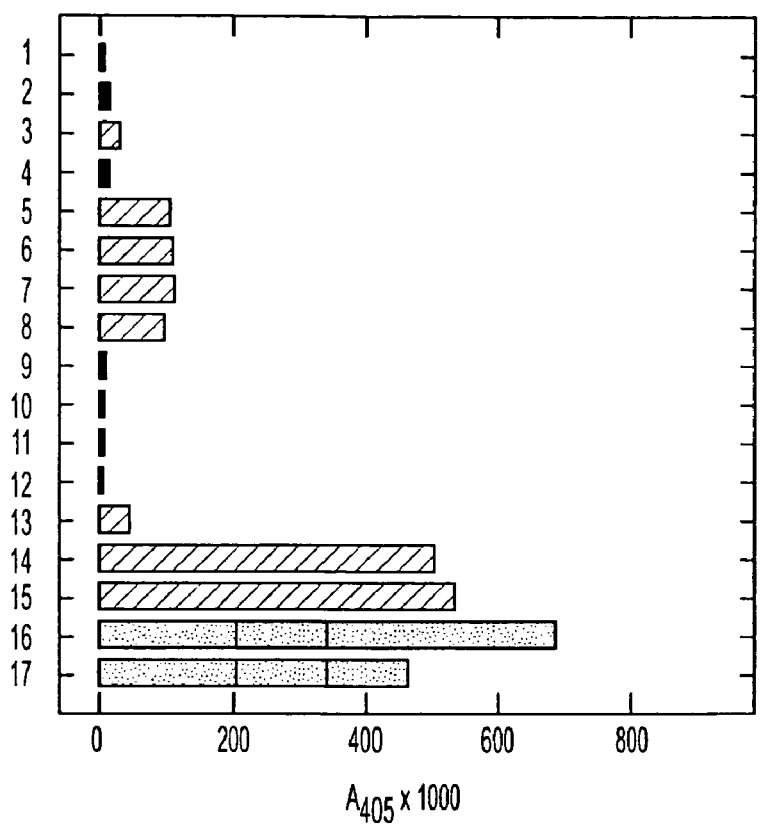
Figure 9B:
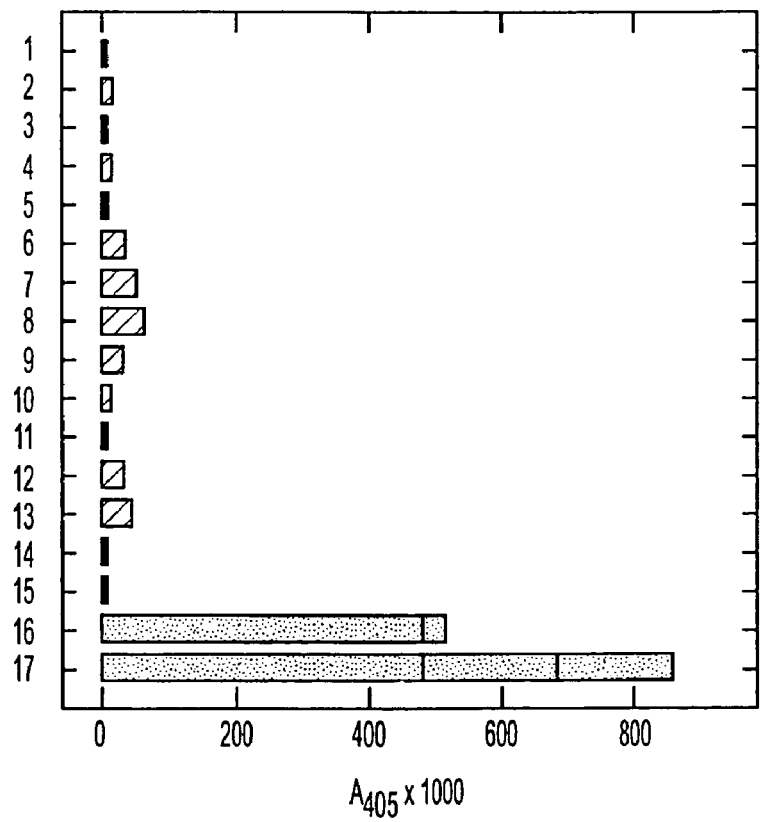

FIG. 9A and FIG. 9B. Recognition of decapeptides spanning the D3 motif, by affinity purified-antibodies generated with D1–3 (FIG. 9A) or GSTD1–3 (FIG. 9B) as immunogens. Peptide sequences are listed in Table 10. Shaded bars represent the response towards control peptides $D1_{11-20}$, and $D1_{23-32}$ of the D1 motif. The assay was conducted as described for FIG. 9 above.

Figure 10:
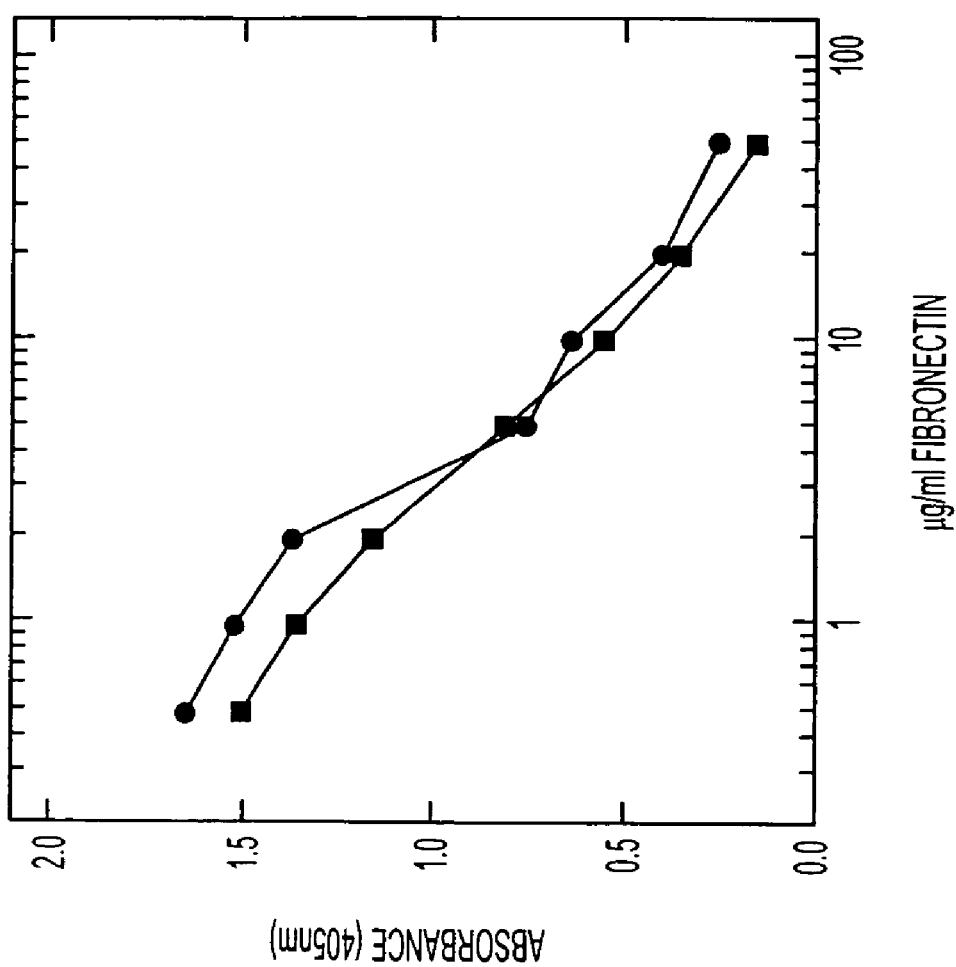

FIG. 10. Competition between soluble Fn, and anti-$D1_{21-34}$ ( ) or anti-$D3_{20-33}$ (■) F(ab')$_2$ fragments for binding to FnBP purified from *S. aureus* strain Newman. The F(ab')$_2$ fragments were diluted to 100 μg/ml in antibody buffer containing the indicated concentrations of soluble Fn, and added to wells of Corning microtiter plates coated with 5 μg/ml of FnBP. Secondary antibody was alkaline-phosphatase conjugated F(ab')$_2$ fragment of F(ab')2-specific goat anti-rabbit IgG.

Figure 11:
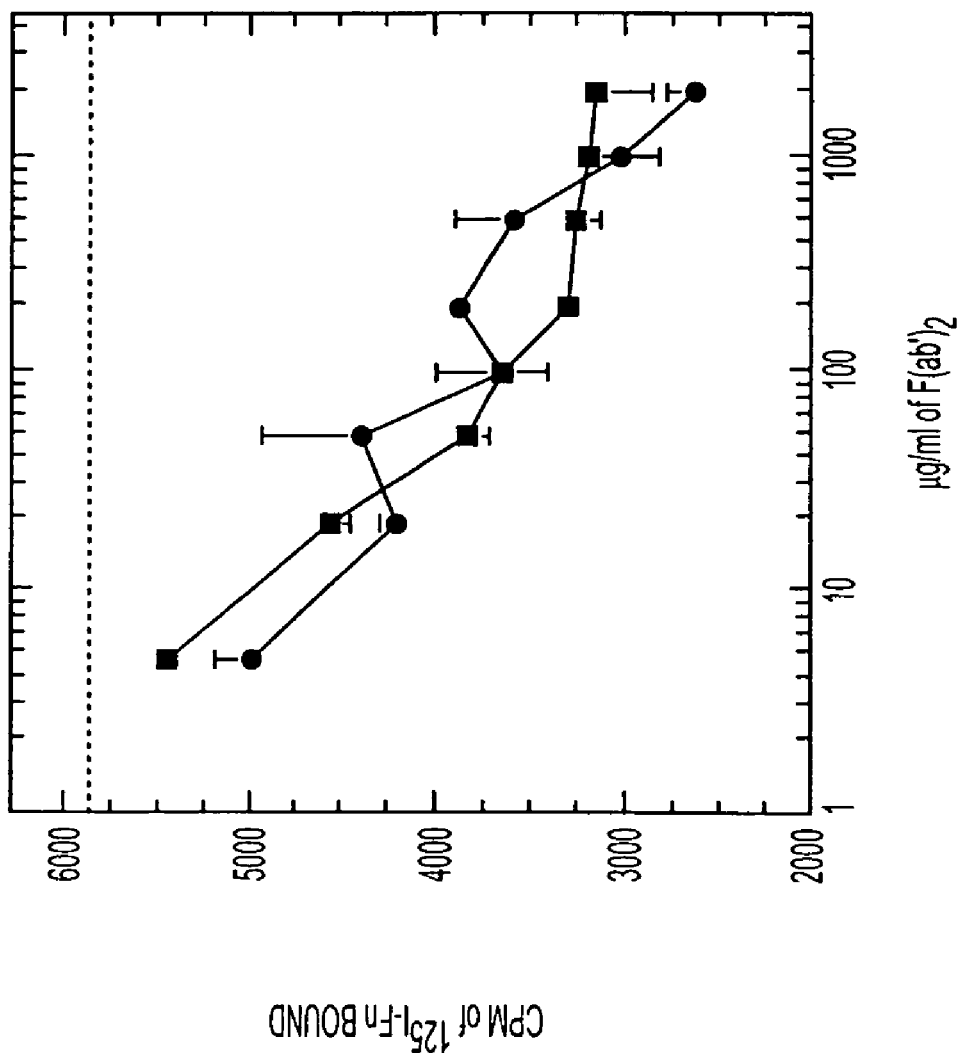

FIG. 11. Inhibition of $^{125}$I-fibronectin-binding to *S. aureus* L857 by anti-$D1_{21-34}$ (●) or anti-$D3_{20-33}$ (■) F(ab')$_2$ fragments. Each point represents the average of triplicate determinations, and the dashed line indicates the amount of binding in the absence of added F(ab')$_2$ fragments. Preimmune F(ab')$_2$ did not inhibit Fn-binding at any of the concentrations assayed.

Figure 12:
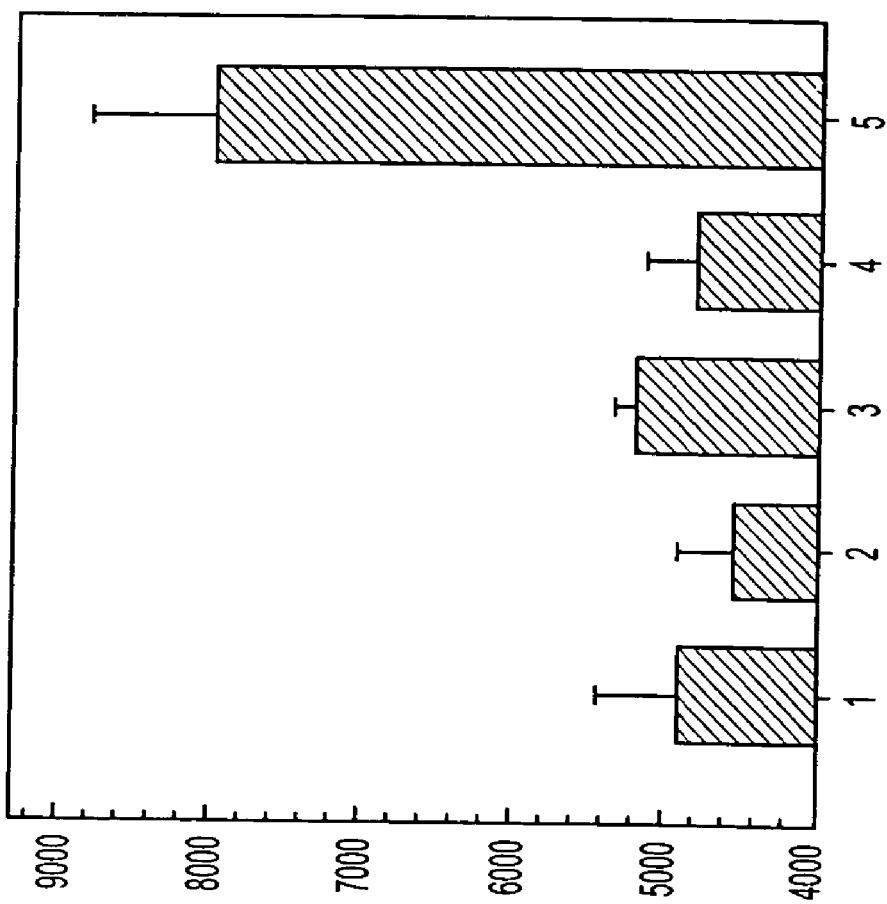

FIG. 12. Assay for additive or synergistic inhibition of Fn-binding by mixtures of anti-D1$_{21-34}$ and D3$_{20-33}$ F(ab')$_2$ fragments at concentrations of 100 μg/ml (bar 1) and 200 μg/ml (bar 2), compared to inhibition by 100 μg/ml of anti-D1$_{21-34}$ (bar 3) or D3$_{20-33}$ (bar 4) F(ab')$_2$ alone. Bar 5 represents the binding in the absence of added F(ab')$_2$ fragments, and each column represents the average of triplicate determinations.

Figure 13A:
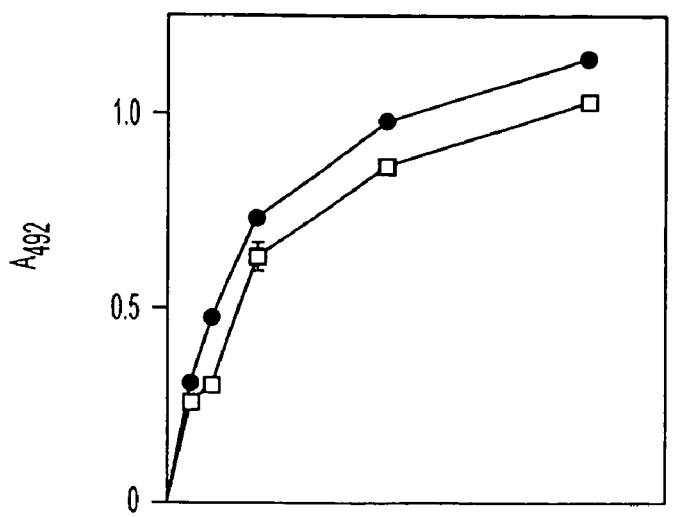
Figure 13B:
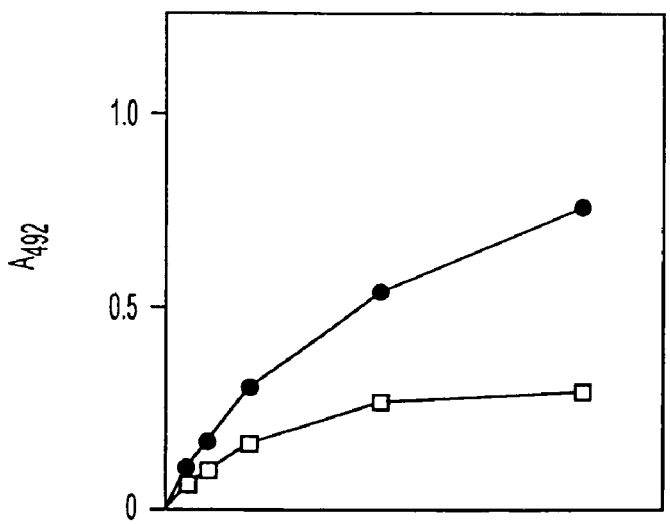
Figure 13C:
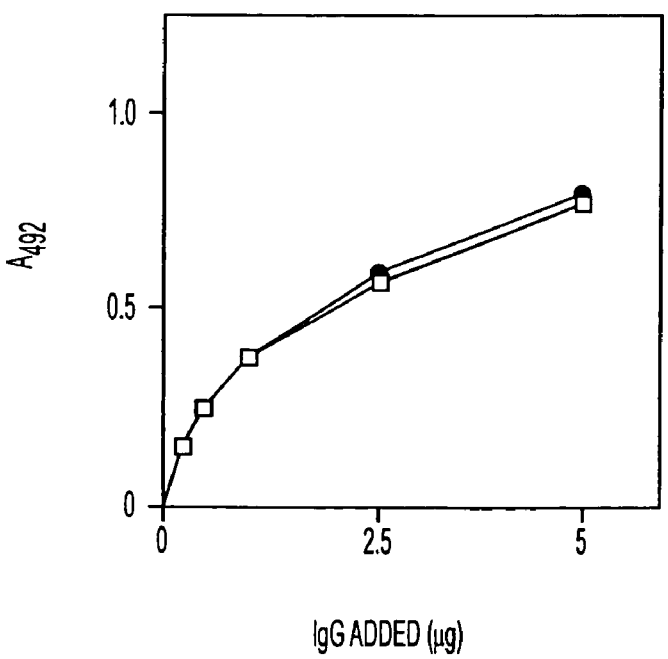

FIG. 13A, FIG. 13B and FIG. 13C. Isolation of anti-LIBS antibodies. IgG obtained from patient I.Z. were loaded on GST-Du1234-Sepharose and fractionated. GST-Du1234 protein immobilized onto microtiter wells (1 μg in 100 μl) was assayed in the absence (□) or presence (●) of N29 with either 100 μl of 20 μg/ml of unfractionated IgG (FIG. 13A), material eluted in the flow-through of the column (FIG. 13B), or antibodies bound and eluted from the affinity matrix (FIG. 13C).

Figure 14A:
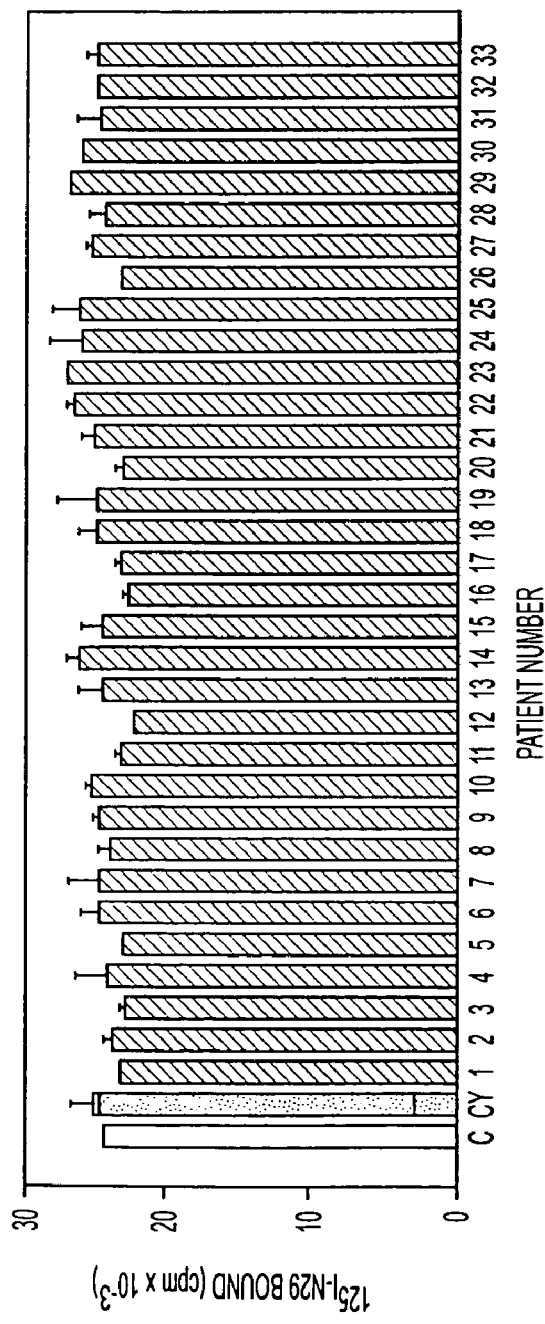
Figure 14B:
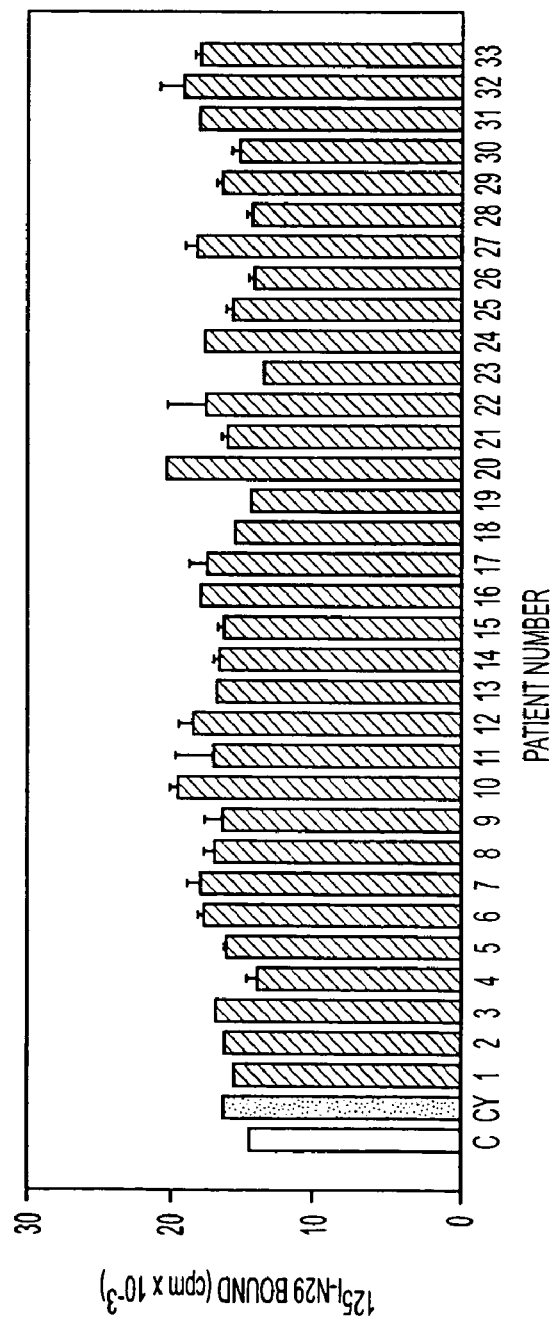

FIG. 14A and FIG. 14B. Antibodies to FnBPA do not inhibit fibronectin binding to S. aureus. FIG. 14A. GST-Du1234 was immobilized onto microtiter wells (1 μg/well) and probed with 8×10$^4$ cpm of $^{125}$I-labeled N29 in the presence of 2 μg of purified IgG from patient sera. After extensive washing with phosphate-buffered saline containing 0.1% Tween 20, the plates were incubated with 200 μl of 2% SDS of 37° C. for 30 min and the radioactivity associated to the wells quantitated in a γ counter. FIG. 14B. Cells of S. aureus Cowan 1 (1×10$^8$) were incubated with $^{125}$I-N29 (5×10$^4$ cpm) in the presence of 50 μg of IgG isolated from patient sera. Bacterial binding in the absence of antibodies was set as 100.

Figure 15:
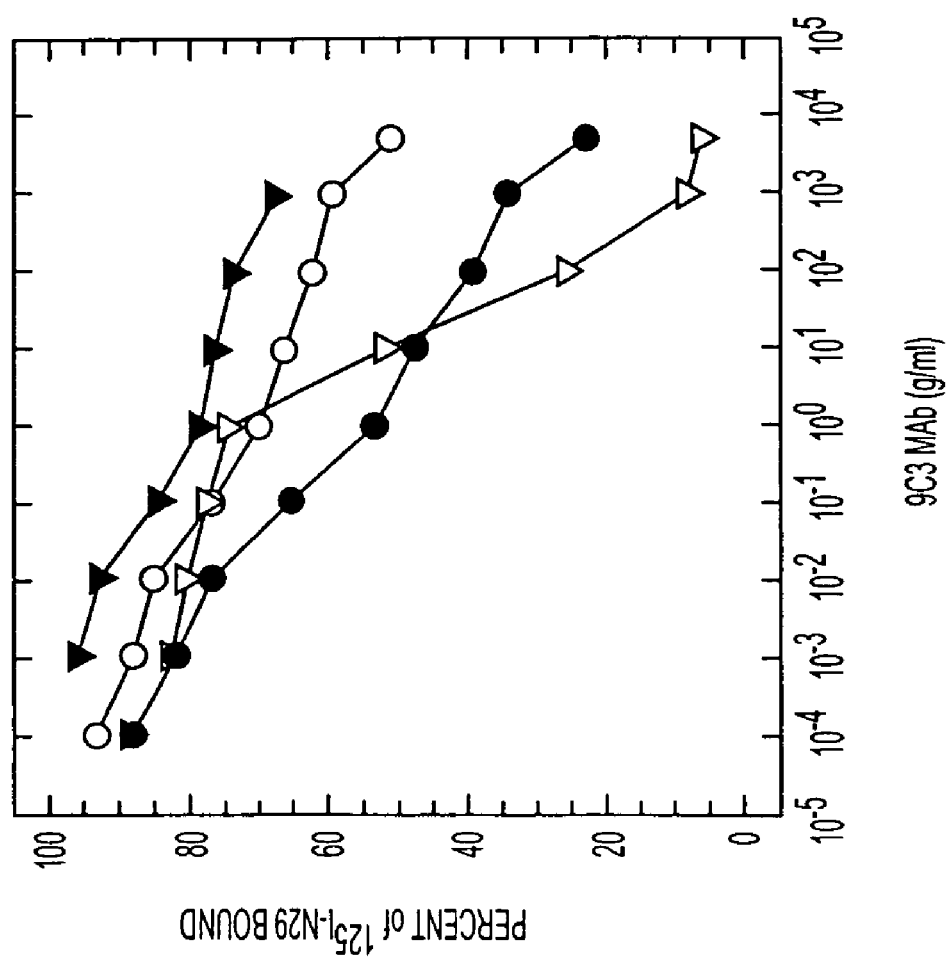

FIG. 15. Inhibition of $^{125}$I-N29 fragment of Fn binding to S. aureus fnbA encoded proteins by mAb 9C3. Corning polystyrene ELISA well strips were coated with 1 μg/ml of recombinant proteins D1–3 (○), D2–3 ( ), GSTD3 (△) or 1×10$^8$ CFU S. aureus cells (▲), followed by various concentrations of mAb 9C3. Then $^{125}$I-N29 fragment of Fn (50,000 cpm) was added, and the amount of $^{125}$I-N29 fragment bound was quantified. The percentage of $^{125}$I-N29 bound is shown on the vertical axis, and the concentration of the 9C3 mAb is shown on the horizontal axis.

Figure 16:
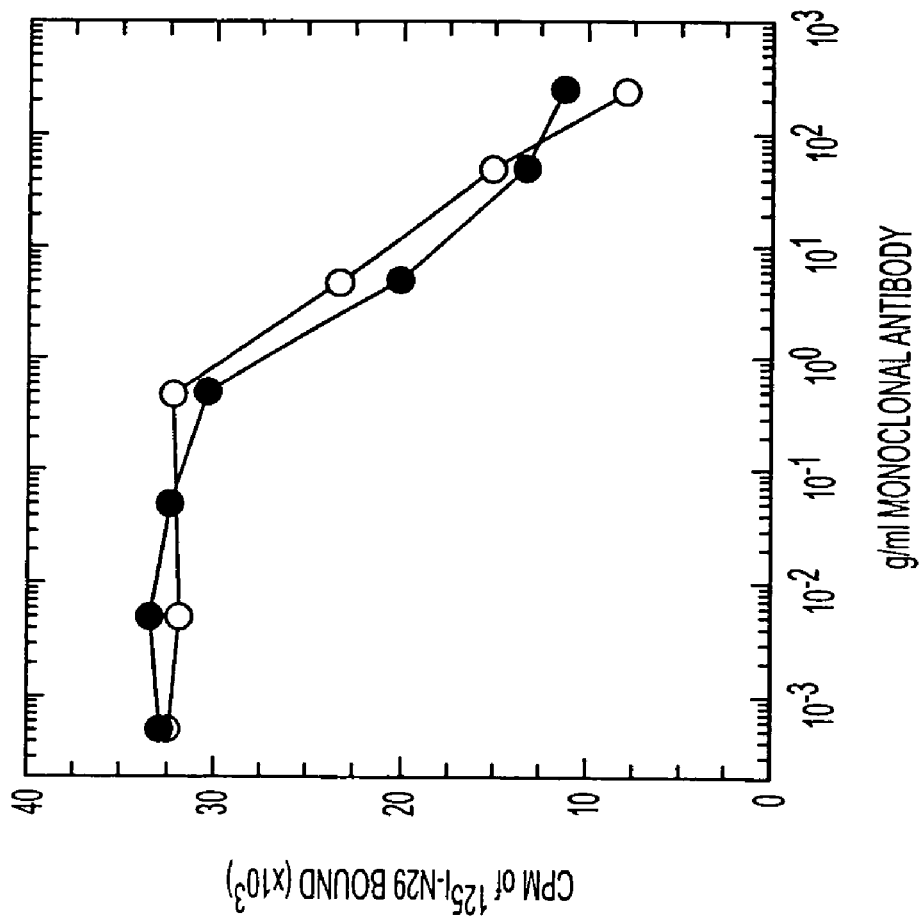

FIG. 16. Inhibition activity of 9C3 and 11A5 monoclonal antibodies. Corning polystyrene ELISA well strips were coated with 1 μg/ml of the recombinant protein GSTD3, followed by various concentrations of mAb 9C3 (●) or mAb 11A5 (○). Then $^{125}$I-N29 fragment of Fn (50,000 cpm) was added, and the amount of $^{125}$I-N29 fragment bound was quantified. The cpm (×10$^3$) of bound $^{125}$I-N29 is shown on the vertical axis, and the concentration of the 9C3 and 11A5 mAbs are shown on the horizontal axis.

4. DETAILED DESCRIPTION OF THE PREFERRED EMBODIMENTS

The present invention overcomes the drawbacks inherent in the prior art by providing, for the first time, antibodies that block the binding of fibronectin to fibronectin binding proteins. These antibodies are raised against peptides that, while based upon epitopes from the fibronectin binding domain of fibronectin binding proteins, do not bind to fibronectin. Previous attempts to produce such blocking antibodies have failed. The inventors reasoned that this failure was due, in part, to the rapid complexation of fibronectin with fibronectin binding proteins and fragments thereof upon introduction into an animal. Thus, the inventors reasoned that peptide epitopes that do not bind to fibronectin, even though based on a fibronectin binding domain of a fibronectin binding protein, do not form a complex with fibronectin in vivo. This allows antibodies to be made against the uncomplexed peptide epitope, which antibodies inhibit or block the binding of fibronectin to fibronectin binding proteins.

The invention provides compositions and methods comprising antibodies that inhibit or block the binding of a fibronectin binding protein to fibronectin, peptides that, upon immunization into a selected animal, produce such antibodies, methods for the identification of such peptides, and nucleic acid segments encoding such peptides. The instant compositions are useful in a wide variety of embodiments, including, but not limited to, diagnosis and/or treatment of microbial infections mediated by the inhibition of microbial binding to the host cell fibronectin, and methods for active and passive immunization against microbial pathogens, such as streptococcal and staphylococcal pathogens, exemplified using peptide epitopes from the fibronectin binding domain of selected fibronectin binding proteins. The compositions of the present invention include a variety of diagnostic and therapeutic kits.

The technology described herein is used to develop methods and compositions that specifically interfere with bacterial adhesion and the subsequent colonization of host tissues, thus resulting in the prevention of infection. The disclosed methods and compositions are broadly applicable, and have the potential to increase the effectiveness of antibiotic therapy in many situations, and replace antibiotic therapy in a number of other applications. The technology represents a needed and desirable alternative to conventional antibiotic treatment of bacterial pathogens by providing cost-effective prophylactic treatment methods based on the prevention of bacterial adhesion to ECM substrata.

MSCRAMMs (on the bacterial cell surface) and ligands (within the host tissue) are the molecules that interact in a lock and key fashion resulting in the adherence of bacteria to the host. Complete blockage of microbial adhesion is not required to prevent infection. It is only necessary to keep the bacterial inoculum below a critical mass. Several strategies have been developed and are summarized below:

(1) MSCRAMM-Specific Antibody Compositions

High affinity antibodies generated against MSCRAMMs bind to the bacteria and prevent adhesion to host tissues. In addition, antibody coated bacteria are more easily recognized by the immune system resulting in more efficient killing of the bacteria.

(2) Ligand Analogs

Molecules, mimicking specific structure(s) within host tissues that pathogenic bacteria attach, are used to saturate the MSCRAMMs on the surface of the bacteria, thereby preventing adhesion.

(3) MSCRAMM Analogs

Molecules, mimicking the bacterial MSCRAMM are used to saturate the binding site within host tissues, resulting in the inhibition of bacterial adhesion.

The expected efficacy of this approach is based on the documented increased susceptibility of microorganisms to host defenses and antibiotics in the period immediately after contamination, or while circulating in blood, and before attachment to host tissues (Chuard et al., 1993). Conversely, once a bacterial colony has adhered and begun to colonize the host, a biofilm surrounding the bacteria often develops. As a result the bacteria become resistant to many host defense mechanisms and antibiotic attack.

4.1 Abbreviations

ECM, extracellular matrix; Fn, Fibronectin; N29, fibronectin N-terminal fragment; N31, N-terminal tryptic digest fragment of Fn; rFnBD, recombinant fibronectin binding domain; FI, fibronectin Type I repeat; PBS, phosphate-buffered saline; CD, circular dichroism; BSA, bovine serum albumin; GuHCl, guanidine hydrochloride; AAA, amino acid analysis; ANS, 8-anilino-1-naphthalenesulfonic acid; LIBS, ligand-induced binding site; aa, amino acid; EDTA, ethylenediaminetetraacetate disodium; SDS, sodium dodecyl sulfate; PAGE, polyacrylamide gel electrophoresis; DMSO, dimethyl sulfoxide; ELISA, enzyme-linked immunosorbent assay; 9C3 or 11A5 ascites fluid, ascites fluid obtained from mice injected with cloned hybridoma cells expressing the monoclonal antibody 9C3 or 11A5; 9C3 or 11A5 ascites IgG, IgG purified from 9C3 or 11A5 ascites fluid; 9C3 or 11A5 IgG, IgG purified from cultured cloned hybridoma cells expressing 9C3 or 11A5.

4.2 Extracellular Matrix

The ECM contains numerous glycoproteins and proteoglycans which, through inter- and intramolecular interactions, form insoluble matrices. The ECM has a structural function in the tissues but also affects the cellular physiology of the organism. Perhaps the best characterized biological functions of the ECM are related to its ability to serve as a substrata for the adhesion of host tissue cells. This process involves the integrins, a family of heterodimeric ($\alpha/\beta$) cell surface receptors which recognize specific structures in many of the ECM proteins (Hynes, 1992). It is clear that many bacteria also have taken advantage of the ECM as a substrate for adhesion. Like most eukaryotic tissue cells, many bacteria have developed several parallel adhesion mechanisms and this apparent redundancy may reflect the importance of host tissue adherence for the prosperity of the bacteria.

4.2.1 Fibronectin

Fn was the first ECM protein shown to mediate substrate adhesion of eukaryotic tissue cells. Fn is a dimeric glycoprotein with a molecular weight of 410–460 kDa depending on alternative splicing of pre-mRNA and the extent of post-translational modification. Fn is found deposited on the surface of most cells, in the ECM of many tissues, as well as in body fluids such as blood plasma (Hynes, 1989). The structures in the host ligand protein Fn recognized by the MSCRAMMs from staphylococci and streptococci has been partly defined. The N-terminal domain in Fn is the major site recognized by S. aureus (Mosher and Proctor, 1980). This domain is composed of five so called type I units. Recombinant versions of this domain in which different type I units have been deleted failed to bind to bacterial cells (Scottile et al., 1991) suggesting that the five type I units are required for forming a structural unit recognized by the MSCRAMM. However, recent studies by Ingham et al. suggest that the primary binding site is located in type I modules numbered 4 and 5. In addition, S. aureus and S. pyogenes appear to bind to sites in Fn outside of the N-terminal domain (Speziale et al., 1984; Bozzini et al., 1992) possibly via the MSCRAMM with broad specificity for ECM proteins described previously (Jönsson et al., 1995).

4.2.2 Fibrinogen

Fibrinogen (Fib) is produced by hepatocytes and is a major protein in blood plasma. During blood coagulation, fibrinogen is converted to fibrin which aggregates and forms the core of the clot. Fn, which contains Fib-binding sites is incorporated into the clot, and these interacting molecules are subsequently linked to each other through the action of a transglutaminase (Factor XIII). Fn in the ECM together with Fib in the clot can serve as substrata for the adhesion of microorganisms. Furthermore, materials placed into the body rapidly become coated with plasma proteins such as Fib and Fn and these surfaces are then colonized by bacteria that specifically bind to the adsorbed host proteins (Bisno and Waldvogel, 1989). In Fib, a putative binding site for staphylococcal cells has been localized to the C-terminal domain of the $\gamma$-chain and a synthetic peptide corresponding to this domain inhibits the staphylococcal induced "clumping" of Fib (Strong et al., 1982). This domain in Fib is also recognized by the platelet gpIIbIIIa integrin and appears to be exposed when Fib is adsorbed on biomaterial surfaces inducing platelet aggregation (Farrell et al., 1994) but is perhaps cryptic and not exposed in soluble Fib.

4.2.3 Collagen

Collagenous proteins are the major constituents of the ECM (Bornstein and Sage, 1980). Most collagens are synthesized intracellularly as precursor molecules and undergo extensive posttranslational processing prior to secretion and incorporation into the ECM or other collagen-rich tissues such as cartilage (Ramachandran and Reddi, 1976). To date over 18 different type of collagens have been defined, and they are loosely categorized into five groups (Vanderrest and Garrone, 1991). These groups are:

(1) collagens participating in quarter-staggered fibrils, collagen types I, II, III, V, and XI;

(2) fibril-associated with interrupted triple helices, collagen types XII, XIV, and IX;

(3) collagens forming sheets, collagen types IV, VIII, and X;

(4) collagens forming beaded filaments, collagen type VI; and (5) collagens forming anchoring fibrils, collagen type VII.

4.2.4 Fn-Binding MSCRAMM

A Fn-binding MSCRAMM from S. aureus was the first MSCRAMM to be characterized. These studies involved the purification of the native staphylococcal protein (Fröman et al., 1987) followed by the cloning and sequencing of the corresponding gene (Flock et al., 1987). The primary ligand binding site was localized to a domain composed of a 38 amino acid long motif that was repeated 3 times (Signäs et al., 1989). Subsequently, a second gene was characterized encoding a highly homologous Fn-binding MSCRAMM from S. aureus (Jönsson et al., 1991). Two Fn-binding MSCRAMMs were also isolated from Streptococcus dysgalactiae (Lindgren et al., 1992) and sequence analyses of the corresponding genes revealed a protein organization similar to the protein isolated from S. aureus (Lindgren et al., 1993). These proteins also contained domains composed of approximately 40 amino acid long motifs which were repeated 3–4 times and were found to represent the primary ligand binding sites. Fn-binding MSCRAMMs have also been characterized from Streptococcus pyogenes (Kreikemeyer et al., 1995; Sela et al., 1993; Talay et al., 1992). The genes encoding these proteins have been sequenced, and it has been shown that the primary ligand binding site in these proteins is also located to a domain composed of an approximately 40 amino acid long motif repeated 3–4 times (Joh et al., 1994). Sequence comparison of repeated motifs in the different MSCRAMMs revealed a consensus sequence (Joh et al., 1994; McGavin et al., 1993). A number of other bacterial species have been shown to bind Fn and some of the microbial proteins responsible for this interaction have been identified.

4.2.5 Fibrinogen-Binding MSCRAMM

Three staphylococcal proteins appear to bind Fib (Bodön and Flock, 1994). One of these proteins is a cell-associated form of coagulase which is primarily secreted by the bacteria. The gene encoding the "clumping factor" that appears to be the major Fib-binding MSCRAMM expressed by *S. aureus* was recently cloned and sequenced (McDevitt et al., 1994; 1992). The third Fib-binding protein binds a large number of ECM proteins including Fn and Fib (Homonylo-McGavin et al., 1993; Jönsson et al., 1995). Cloning and sequencing of the gene encoding this protein revealed a protein largely composed of a 100 amino acid long motif repeated 6 times. A subsegment in the repeated unit of 30 amino acids has a very high degree of sequence similarity with the peptide binding domain of mammalian MHC II molecules.

Functionally, the staphylococcal protein also shows similarities with MHC II molecules in that it can bind nonglycosylated proteins and synthetic peptides (Jönsson et al., 1995). It is possible that this protein is responsible for the observed binding of several ECM molecules (e.g., vitronectin, bone sialoprotein and thrombospondin) and that the repertoire of MSCRAMMs on staphylococcal cells is less complex than what would be implicated by a one ligand one adhesin paradigm.

4.2.6 Collagen-Binding MSCRAMM

In addition to expressing Fn-binding and Fib-binding MSCRAMMs, *S. aureus* can express a collagen-binding MSCRAMM (Speziale et al., 1986). The cloning, sequencing, and expression of a gene named cna, encoding a *S. aureus* collagen-binding MSCRAMM has been reported (Patti et al., 1992). The cna gene encodes an 1183 amino acid long polypeptide with characteristics of surface proteins from Gram-positive bacteria. A signal sequence (S) is followed by a large non-repetitive region (A). Immediately following is a 187 amino acid motif (B). PCR™ analyses of the cna gene from different clinical isolates reveals that the MSCRAMM can occur in at least four forms containing one, two, three, or four B repeats (Switalski et al., 1993). The B region is followed by a putative cell wall associated region (W), a hydrophobic transmembrane segment (M), and a short cytoplasmic tail (C) rich in positively charged amino acids. Analyses of a number of different clinical isolates revealed that only *S. aureus* strains expressing collagen binding activity contained the cna gene.

The collagen binding domain (CBD) was localized within the 135-kDa *S. aureus* collagen adhesin (Patti et al., 1993). Using deletion mutagenesis in combination with Western ligand blot and direct binding assays, the CBD was initially found to reside within the approximate 55 kDa A domain (CBD 30–529) of the adhesin. Subsequent studies localized the CBD to a 168 amino acid long segment (CBD 151–318) within CBD (30–529). More recently a discrete collagen binding site has been identified within the *S. aureus* collagen adhesin that is located in a region between amino acids $D^{209}$ and $Y^{233}$. Moreover, two residues $N^{232}$ and $Y^{233}$ were shown to be required for complete collagen binding activity (Patti et al., 1995).

It has been demonstrated that the collagen-binding MSCRAMM is needed not only for the adherence of bacteria to collagen-coated substrates, but also to cartilage, a complex collagen-containing tissue. All strains tested that expressed the collagen-binding MSCRAMM were able to adhere to cartilage, whereas those strains lacking the collagen-binding MSCRAMM did not adhere. Furthermore, pre-incubation of the collagen-binding MSCRAMM with polyclonal antibodies against the native MSCRAMM or blocking of the ligand binding site in the substrate with soluble recombinant receptor protein resulted in effective inhibition of bacterial attachment. The collagen adhesin is both necessary and sufficient for mediating adherence to cartilage, since polystyrene beads coated with the purified collagen-binding MSCRAMM protein attached to cartilage discs, whereas beads coated with a *S. aureus* Fn-binding MSCRAMM failed to attach (Switalski et al., 1993).

4.3 Biological Importance of MSCRAMMs

The importance of different Fn and Fib-binding MSCRAMMs as adhesins is now clearly established. These bacterial surface adhesins mediate microbial adhesion to different supporting materials coated with isolated Fn or Fib and to biomaterials conditioned with blood plasma. Bacterial colonization of implanted biomaterials is often responsible for the development of life-threatening infections. The ability of *S. aureus* MSCRAMM isogenic mutants to adhere to serum-conditioned polymeric biomaterials was studied in a canine arteriovenous shunt model. A *S. aureus* Fib-binding MSCRAMM mutant (clf) showed over an 80% reduction in the ability to bind the plasma-conditioned shunt compared to the parental strain. Complementation of the isogenic strain with an intact copy of the clf gene completely restored its ability to attach to the shunt (Vaudaux et al., 1995).

The virulence of a series of coa- and clf- *S. aureus* isogenic mutants was analyzed in a rat model of catheter-induced endocarditis (EE) (Moreillon et al., 1995). Inactivation of the gene encoding coagulase did not affect the ability of the *S. aureus* mutant to induce EE. However, the ability to induce EE was significantly diminished in mutants lacking only clumping factor or both clumping factor and coagulase. Additional studies have investigated the virulence of Fn and Fib-binding MSCRAMM negative double mutants in this model.

The biological importance of a collagen-binding adhesin in the pathogenesis of septic arthritis has been examined by comparing the virulence of two sets of *S. aureus* mutants in an animal model (Patti et al., 1994). Collagen adhesin negative isogenic mutant PH100 was constructed by replacing the chromosomal collagen adhesin gene (cna) in a clinical strain Phillips, with an inactivated copy of the gene. Collagen adhesin positive mutant *S. aureus* CYL574 was generated by introducing the cna gene into CYL316, a strain that normally lacks the cna gene. Greater than 70% of the mice injected with the CNA+ strains developed clinical signs of arthritis, whereas less than 27% of the animals injected with CNA+ strains showed symptoms of disease. Furthermore, mice injected with the CNA+ strain Phillips had remarkably elevated levels of IgG1 and IL-6 when compared to mice injected with the CNA+ mutant PH100. Taken together these results demonstrate that the collagen adhesin plays an important role in the pathogenesis of septic arthritis induced by *S. aureus*.

4.4 Characterization of LIBS in Fn-Binding MSCRAMMS

The "induced fit" ligand binding mechanism of the Fn-binding MSCRAMM (ligand induced binding site; LIBS) has immunological consequences in that it does not allow the generation of high affinity blocking antibodies. Furthermore, the Fn binding sequence contains several similar (but not identical) sequences, each of which is capable of ligand binding. Hence, a sequence specific antibody may recognize an epitope in one of the Fn binding sequences and interfere with its ligand binding, while leaving some or all of the other binding sequences intact. This may represent a clever previously unknown strategy used by microbes to avoid host defense mechanisms. Therefore, only Fn-binding MSCRAMMs that lack binding activity would be expected to serve as antigens for producing blocking antibodies.

The contribution to Fn binding by the acidic residues in FnBPA has been previously determined by chemical modification using 1-ethyl-3-(3-dimethylaminopropyl) carbodiimide (EDC) mediated condensation of glycine methyl ester on the carboxyl group (McGavin et al., 1991). These modification studies indicated that COOH groups play a critical role in the ability of the MSCRAMM to bind Fn. Conversely, dihydroxypropylation reduction of lysine residues and the oxidation of tyrosine residues by the addition of tetranitromethane had no affect on Fn binding.

Based on this observation, the inventors hypothesized that only Fn-binding MSCRAMMs that lack binding activity should lead to blocking antibodies. A recombinant version of the Fn-binding MSCRAMM rFnBD-D was chemically modified with EDC as previously described (McGavin et al., 1991) and tested for its ability to inhibit Fn binding to S. aureus. The modified rFnBD-D exhibited no inhibitory activity, whereas the native rFnBD-D inhibited Fn binding to S. aureus in a dose-dependent manner. The chemically modified rFnBD-D was then used to immunize rabbits. Subsequent studies with the immune sera and purified IgG from the immunized rabbit indicated that the antibodies raised reacted strongly toward the antigen, but exhibited little reactivity to the native rFnBD-D. Moreover, the purified immune IgG did not inhibit the binding of Fn to S. aureus. With efficiencies of approximately 98%, chemical modification had the advantage of providing a quick and efficient method for probing entire classes of amino acids. However, an inherent disadvantage in this global approach is that the contribution to binding of individual amino acids was not detected.

4.4.1 Analyses of Recombinant FnBPS

Biophysical characterization of recombinant Fn-binding MSCRAMMs originating from several different species of Gram-positive bacteria have suggested an "induced fit" binding interaction. The far-UV CD spectra (190–250 nm) of recombinant forms of the ligand binding domain, in a phosphate buffered saline solution at neutral pH, were characteristic of a protein containing little or no regular secondary structure. The intrinsic viscosity of this domain was found to be the same in the presence or absence of 6 M guanidine hydrochloride, indicating that the native and denatured conformations are indistinguishable. On addition of Fn N-terminus as ligand to the recombinant adhesin there was a large change in the resulting far-UV CD difference spectra. At a 4.9 molar excess of the N-terminus the difference spectra shifted to what was predominately a β-sheet conformation, as judged by comparison with model far-UV CD spectra. The Fn N-terminal domain undergoes a minute but reproducible blue-shift of its intrinsic tryptophan fluorescence on addition of rFnBD-A, which contains no tryptophan residues. Since this result indicates that there is no large change in the environment of the tryptophan residues of the N-terminus on binding, the large shift in secondary structure observed by CD analysis is attributed to induction of a predominately β-sheet secondary structure in the adhesin on binding to Fn N-terminus.

In vivo, there may be several reasons to explain these results, e.g., when an active Fn-binding MSCRAMM (recombinant or bacterial cell surface localized) enters an animal, we can assume that the protein quickly recognizes and binds Fn present in the serum. If blocking antibodies were not already present or if they existed in extremely low concentrations, then the Fn-binding site on the MSCRAMM would bind Fn and important epitopes would no longer be available for antigen recognition by the immunoglobulins.

If this argument is correct, it would represent a clever previously unknown strategy used by microbes to avoid host defense mechanisms. Recent studies by the inventors suggest this is exactly what is happening in patients infected with S. aureus. The antibodies from patients that have had clinically diagnosed S. aureus infections were analyzed (See Example 10 and FIG. 13A, FIG. 13B, FIG. 13C, FIG. 14A and FIG. 14B). Purified IgG from the serum of these children did not significantly inhibit the binding of S. aureus to Fn, even though ELISA showed that the IgG recognized the Fn-binding MSCRAMM. Most interesting was the finding that in ELISA the IgG reacted most strongly to the Fn-binding MSCRAMM complexed with Fn. Taken together, these data indicate the lack of blocking antibodies against the Fn-binding MSCRAMM is not a laboratory phenomenon or artifact of experimental design. Rather, S. aureus has found a way to protect a critical adhesin from host defense mechanisms. Moreover, it indicates that site-specific alterations in the Fn-binding MSCRAMM are necessary to create an antigen that will generate high affinity blocking antibodies.

4.5 Fibronectin Binding Protein-Derived Peptides and Epitopes

Because of the pivotal role that tissue adherence plays in the pathogenic process, bacterial adherence has been identified as a target in new strategies to prevent and treat infections. The present invention demonstrates it is possible to use adhesins, and MSCRAMMs in particular, in the development of vaccines and the production of antibodies to aid conventional host defense and block tissue adherence.

4.5.1 Epitopic Core Sequences

The present invention is also directed to protein or peptide compositions, free from total cells and other peptides, which comprise a purified protein or peptide which incorporates an epitope that is immunologically cross-reactive with one or more of the antibodies of the present invention.

As used herein, the term "incorporating an epitope(s) that is immunologically cross-reactive with one or more anti-FnBP antibodies" is intended to refer to a peptide or protein antigen which includes a primary, secondary or tertiary structure similar to an epitope located within an FnBP polypeptide. The level of similarity will generally be to such a degree that monoclonal or polyclonal antibodies directed against the FnBP polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of MSCRAMM epitopes, and particularly Fn-binding epitopes such as those derived from sfb-, fnbA, fnbB, fnA, or fnB gene products and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 5 to about 25 amino acids in length, and more preferably about 8 to about 20 amino acids in length. It is proposed that shorter antigenic peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to MSCRAMM-related sequences, and particularly those FnBP domains which bind the ECM component, Fn. It is proposed that these regions represent those which are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen binding sites on MSCRAMM epitope-specific antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence expected by the present disclosure is generally on the order of about 5 amino acids in length, with sequences on the order of 8 or 25 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar7 software, DNAStar, Inc., Madison, Wis.) may also be useful in designing synthetic FnBPs, and FnBP-derived epitopes and epitope analogs in accordance with the present disclosure.

The peptides provided by this invention are ideal targets for use as vaccines or immunoreagents for the treatment of various staphylococcal- and streptococcal-related diseases, and in particular, those caused by species which contain Fn-binding MSCRAMM genes, and hence those which express either the sfb, fnbA, fnbB, fnA or fnB gene product on the cell surface and in turn interact with ECM components such as Fn to promote bacterial adhesion to host cells.

In this regard, particular advantages may be realized through the preparation of synthetic peptides that include epitopic/immunogenic-core sequences. These epitopic core sequences may be identified as hydrophilic and/or mobile regions of the polypeptides or those that include a T cell motif. It is known in the art that such regions represent those that are most likely to promote B cell or T cell stimulation, and, hence, elicit specific antibody production. In the case of preventing bacterial adhesion, the preparation of epitopes which produce antibodies which inhibit the interaction of a Fn-specific MSCRAMM gene product and Fn is particularly desirable.

To confirm that a protein or peptide is immunologically cross-reactive with, or a biological functional equivalent of, one or more epitopes of the disclosed peptides is also a straightforward matter. This can be readily determined using specific assays, e.g., of a single proposed epitopic sequence, or using more general screens, e.g., of a pool of randomly generated synthetic peptides or protein fragments. The screening assays may be employed to identify either equivalent antigens or cross-reactive antibodies. In any event, the principle is the same, i.e., based upon competition for binding sites between antibodies and antigens.

Suitable competition assays that may be employed include protocols based upon immunohistochemical assays, ELISAs, RIAs, Western or dot blotting and the like. In any of the competitive assays, one of the binding components, generally the known element, such as the FnBP-derived peptide, or a known antibody, will be labeled with a detectable label and the test components, that generally remain unlabeled, will be tested for their ability to reduce the amount of label that is bound to the corresponding reactive antibody or antigen.

As an exemplary embodiment, to conduct a competition study between an MSCRAMM and any test antigen, one first labels FnBPA with a detectable label, such as, e.g., biotin or an enzymatic, radioactive or fluorogenic label, to enable subsequent identification. One then incubates the labeled antigen with the test antigen to be examined at various ratios (e.g., 1:1, 1:10 and 1:100) and, after mixing, one then adds the mixture to a known antibody, such as 9C3 or 11A5. Preferably, the known antibody is immobilized, e.g., by attaching to an ELISA plate. The ability of the mixture to bind to the antibody is determined by detecting the presence of the specifically bound label. This value is compared to a control value in which no potentially competing (test) antigen is included in the incubation.

The assay may be any one of a range of immunological assays based upon hybridization, and the reactive antigens are detected by means of detecting their label, e.g., using streptavidin in the case of biotinylated antigens or by using a chromogenic substrate in connection with an enzymatic label or by simply detecting a radioactive or fluorescent label.

The reactivity of the labeled antigen, e.g., an FnBP-derived peptide, in the absence of any test antigen is the control high value. The control low value is obtained by incubating the labeled antigen with an excess of unlabeled FnBP antigen, when competition occurs and reduce binding. A significant reduction in labeled antigen reactivity in the presence of a test antigen is indicative of a test antigen that is "cross-reactive", i.e., that has binding affinity for the same antibody. "A significant reduction", in terms of the present application, may be defined as a reproducible (i.e., consistently observed) reduction in binding.

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Syntheses of epitopic sequences, or peptides which include an antigenic epitope within their sequence, are readily achieved using conventional synthetic techniques such as the solid phase method (e.g., through the use of a commercially-available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

4.5.2 Peptide Compositions

An important aspect of the present invention includes novel compositions comprising isolated and purified Sfb-, FnBA-, FnBB-, FnBPA- and FnBPB-derived peptides, modifications of these epitopic peptides, peptides derived from site-specifically-mutagenized nucleic acid segments encoding such peptides, and antibodies derived from such peptides. It will, of course, be understood that one or more than one MSCRAMM epitope-encoding nucleic acid segment may be used in the methods and compositions of the invention. The nucleic acid delivery methods may thus entail the administration of one, two, three, or more, MSCRAMM epitope-encoding nucleic acid segments encoding one or more peptide epitopes. The maximum number of nucleic acid segments that may be applied is limited only by practical considerations, such as the effort involved in simultaneously preparing a large number of nucleic acid segment constructs or even the possibility of eliciting an adverse cytotoxic effect.

The particular combination of nucleic acid segments may be two or more distinct nucleic acid segments derived from one or more species of streptococci or staphylococci; or it may be such that a nucleic acid segment from one gene encoding a Fn binding protein is combined with another nucleic acid segment and/or another peptide or protein such as a cytoskeletal protein, cofactor or other biomolecule; a hormone or growth factor gene may even be combined with a nucleic acid segment or gene encoding portions or all of a cell surface receptor capable of interacting with the polypeptide product of the first nucleic acid segment.

In using multiple nucleic acid segments, they may be combined on a single genetic construct under control of one or more promoters, or they may be prepared as separate constructs of the same or different types. Thus, an almost endless combination of different nucleic acid segments and genetic constructs may be employed. Certain combinations of nucleic acid segments may be designed to, or their use may otherwise result in, achieving synergistic effects on Fn binding and/or stimulation of an immune response against peptides derived from translation of such nucleic acid segments. Any and all such combinations are intended to fall within the scope of the present invention. Indeed, many synergistic effects have been described in the scientific literature, so that one of ordinary skill in the art would readily be able to identify likely synergistic combinations of nucleic acid segments, or even nucleic acid segment-peptide combinations.

It will also be understood that, if desired, the nucleic acid segment or gene encoding a particular MSCRAMM-derived peptide may be administered in combination with further agents, such as, e.g., proteins or polypeptides or various pharmaceutically-active agents. So long as the composition comprises a nucleic acid segment encoding all or portions of an MSCRAMM polypeptide, there is virtually no limit to other components which may also be included, given that the additional agents do not cause a significant adverse effect upon contact with the target cells or host tissues. The nucleic acids may thus be delivered along with various other agents as required in the particular instance. The formulation of pharmaceutically-acceptable excipients and carrier solutions are well-known to those of skill in the art, as is the development of suitable dosing and treatment regimens for using the particular compositions herein described in oral, parenteral, and/or intravenous administration and formulation.

4.5.3 Recombinant Vectors Expressing Sfb-, FnBA-, FnBB- FnBPA- and FnBPB-Derived Epitopes A particular aspect of this invention provides novel ways in which to utilize recombinant Sfb-, FnBA-, FnBB-, or FnBPA- or FnBPB-derived peptides, nucleic acid segments encoding these peptides, recombinant vectors and transformed host cells comprising *S. dysgalactiae* fnbA- or fnbB-derived DNA segments, recombinant vectors and transformed host cells comprising *S. aureus* fnbA- or fnbB-derived DNA segments, and recombinant vectors and transformed host cells comprising *S. pyogenes* sfb-derived DNA segments. As is well known to those of skill in the art, many such vectors and host cells are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a protein or peptide of interest (e.g., an FnBA or FnBB epitopic sequence from *S. dysgalactiae*, an FnBPA or FnBPB epitopic sequence from *S. aureus*, or an Sfb epitopic sequence from *S. pyogenes*) and does not include any coding or regulatory sequences that would have an adverse effect on cells. Therefore, it will also be understood that useful nucleic acid sequences may include additional residues, such as additional non-coding sequences flanking either of the 5' or 3' portions of the coding region or may include various regulatory sequences.

After identifying an appropriate epitope-encoding nucleic acid molecule, it may be inserted into any one of the many vectors currently known in the art, so that it will direct the expression and production of the protein or peptide epitope of interest (e.g., an FnBA or FnBB epitopic sequence from *S. dysgalactiae* or an FnBPA or FnBPB epitopic sequence from *S. aureus*) when incorporated into a host cell. In a recombinant expression vector, the coding portion of the DNA segment is positioned under the control of a promoter. The promoter may be in the form of the promoter which is naturally associated with an fnA, fnB, fnbA or fnbB gene or nucleic acid segment, as may be obtained by isolating the 5' non-coding sequences located upstream of the coding segment, for example, using recombinant cloning and/or PCR™ technology, in connection with the compositions disclosed herein. Direct amplification of nucleic acids using the PCR™ technology of U.S. Pat. Nos. 4,683,195 and 4,683,202 (herein incorporated by reference) are particularly contemplated to be useful in such methodologies.

In certain embodiments, it is contemplated that particular advantages will be gained by positioning the Sfb-, FnBA-, FnBB-, FnBPA- or FnBPB-encoding DNA segment under the control of a recombinant, or heterologous, promoter. As used herein, a recombinant or heterologous promoter is intended to refer to a promoter that is not normally associated with an sfb, fnbA, fnbB, fnA, or fnB gene segment in its natural environment. Such promoters may include those normally associated with other MSCRAMM-encoding genes, and/or promoters isolated from any other bacterial, viral, eukaryotic, or mammalian cell. Naturally, it will be important to employ a promoter that effectively directs the expression of the DNA segment in the particular cell containing the vector comprising the Sfb-, FnBA-, FnBB-, FnBPA- or FnBPB-epitope encoding nucleic acid segment.

The use of recombinant promoters to achieve protein expression is generally known to those of skill in the art of molecular biology, for example, see Sambrook et al., (1989). The promoters employed may be constitutive, or inducible, and can be used under the appropriate conditions to direct high level or regulated expression of the introduced DNA segment. For eukaryotic expression, the currently preferred promoters are those such as CMV, RSV LTR, the SV40 promoter alone, and the SV40 promoter in combination with the SV40 enhancer. Prokaryotic expression of nucleic acid segments of the present invention may be performed using methods known to those of skill in the art, and will likely comprise expression vectors and promoter sequences such as those provided by tac, trp, lac, lacUV5 or T7.

4.5.4 Expression of Recombinant Proteins

Recombinant clones expressing sfb-, fnbB-, fbA-, JbB and fnbA-derived nucleic acid segments may be used to prepare purified peptide antigens as well as mutant or variant protein species in significant quantities. The selected antigens, and variants thereof, are proposed to have significant utility in diagnosing and treating staphylococcal and streptococcal infections. For example, it is proposed that these antigens, or peptide variants, or antibodies against such antigens may be used in immunoassays to detect staphylococci or streptococci or as vaccines or immunotherapeutics to treat staphylococcal and/or streptococcal infections, and to prevent bacterial adhesion to ECM components such as Fn.

Since antibodies, including monoclonal antibodies, to the MSCRAMM epitopes of the present invention are described herein, the use of immunoabsorbent techniques to purify these peptides, or their immunologically cross-reactive variants, is also contemplated. It is proposed that useful antibodies for this purpose may be prepared generally by the techniques disclosed hereinbelow, or as is generally known in the art for the preparation of monoclonals (see, e.g., U.S. Pat. Nos. 4,514,498 and 4,740,467), and those reactive with the desired protein or peptides selected.

Additionally, by application of techniques such as DNA mutagenesis, the present invention allows the ready preparation of so-called "second generation" molecules having modified or simplified protein structures. Second generation proteins will typically share one or more properties in common with the full-length antigen, such as a particular antigenic/immunogenic epitopic core sequence. Epitopic sequences can be provided on relatively short molecules prepared from knowledge of the peptide, or encoding DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence. This is particularly desirable in the preparation of blocking antibodies which prevent bacterial adhesion to Fn, as outlined in Example 3.

4.5.5 Expression or SFB-, FnBA-, FnBB-, FnBPA- and FnBPB-Derived MSCRAMM Epitopes For the expression of MSCRAMM-derived epitopes, once a suitable clone or clones have been obtained, whether they be native sequences or genetically-modified, one may proceed to prepare an expression system for the recombinant preparation of MSCRAMM-derived epitopes. The engineering of DNA segment(s) for expression in a prokaryotic or eukaryotic system may be performed by techniques generally known to those of skill in recombinant expression. It is believed that virtually any expression system may be employed in the expression of MSCRAMM-derived MSCRAMM epitopes.

MSCRAMM-derived epitopes may be successfully expressed in eukaryotic expression systems, however, it is also envisioned that bacterial expression systems may be preferred for the preparation of MSCRAMM-derived epitopes for all purposes. The DNA sequences encoding the desired MSCRAMM-derived epitope (either native or mutagenized) may be separately expressed in bacterial systems, with the encoded proteins being expressed as fusions with D-galactosidase, ubiquitin, *Schistosoma japonicum* glutathione S-transferase, *S. aureus* Protein A, maltose binding protein, and the like. It is believed that prokaryotic expression systems, and particularly bacterial expression systems will ultimately have advantages over eukaryotic expression in terms of ease of use and quantity of materials obtained thereby.

It is proposed that transformation of host cells with DNA segments encoding such epitopes will provide a convenient means for obtaining MSCRAMM-derived epitope peptides. Genomic or extra-chromosomal sequences are suitable for eukaryotic expression when present in appropriate expression vectors, and under suitable conditions to permit expression of the encoded protein, as the host cell will, of course, process the nucleic acid transcripts to yield functional mRNA for subsequent translation into protein.

It is similarly believed that almost any eukaryotic expression system may be utilized for the expression of MSCRAMM-derived epitopes, e.g., baculovirus-based, glutamine synthase-based or dihydrofolate reductase-based systems may be employed. However, in preferred embodiments, it is contemplated that plasmid vectors incorporating an origin of replication and an efficient eukaryotic promoter, as exemplified by the eukaryotic vectors of the pCMV series, such as pCMV5, will be of most use.

For expression in this manner, one positions the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes MSCRAMM-derived epitope-encoding DNA sequences, an appropriate polyadenylation site (e.g., 5'-AATAAA-3') if one was not contained within the original cloned segment. Typically, the poly-A addition site is placed about 30 to 2000 nucleotides "downstream" of the termination site of the protein at a position prior to transcription termination.

It is contemplated that virtually any of the commonly employed host cells can be used in connection with the expression of MSCRAMM-derived epitopes in accordance herewith. Examples include cell lines typically employed for eukaryotic expression such as 239, AtT-20, HepG2, VERO, HeLa, CHO, WI 38, BHK, COS-7, RIN and MDCK cell lines.

It is contemplated that MSCRAMM-derived epitopic peptides may be "overexpressed", i.e., expressed in increased levels relative to its natural expression in human cells, or even relative to the expression of other proteins in a recombinant host cell containing MSCRAMM-derived epitope-encoding DNA segments. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural MSCRAMM-derived epitope-producing animal cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding an MSCRAMM-derived epitope peptide has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e. they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive promoters are generally viral in origin, and include the cytomegalovirus (CMV) promoter, the Rous sarcoma long-terminal repeat (LTR) sequence, and the SV40 early gene promoter. The use of these constitutive promoters will ensure a high, constant level of expression of the introduced genes. The inventors have noticed that the level of expression from the introduced genes of interest can vary in different clones, probably as a function of the site of insertion of the recombinant gene in the chromosomal DNA. Thus, the level of expression of a particular recombinant gene can be chosen by evaluating different clones derived from each transfection experiment; once that line is chosen, the constitutive promoter ensures that the desired level of expression is permanently maintained. It may also be possible to use promoters that are specific for cell type used for engineering, such as the insulin promoter in insulinoma cell lines, or the prolactin or growth hormone promoters in anterior pituitary cell lines.

4.5.6 DNA Segments

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding an MSCRAMM-derived peptide in its natural environment. Such promoters may include promoters normally associated with other genes, and/or promoters isolated from any viral, prokaryotic (e.g., bacterial), eukaryotic (e.g., fungal, yeast, plant, or animal) cell, and particularly those of mammalian cells. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter/expression systems contemplated for use in high-level expression include, but are not limited to the *Pichia* expression vector system (Pharmacia LKB Biotechnology), a baculovirus system for expression in insect cells, or any suitable yeast or bacterial expression system.

The ability of nucleic acid segments to be used as probes to specifically hybridize to MSCRAMM-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 48, about 50, about 51, about 54, about 57, about 60, about 63, about 66, about 69, about 72, about 75, about 90, or even of about 100 to about 200 nucleotides or so, identical or complementary to the DNA sequences disclosed herein, are particularly contemplated as hybridization probes for use in, e.g., Southern and Northern blotting. Smaller fragments will generally find use in hybridization embodiments, wherein the length of the contiguous complementary region may be varied, such as between about 10 and about 14 or even up to about 25, 50, or 100 nucleotides, but larger contiguous complementarity stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 15 to about 25 contiguous nucleotides, or even longer where desired.

Of course, fragments may also be obtained by other techniques such as, e.g. by mechanical shearing or by restriction enzyme digestion. Small nucleic acid segments or 5 fragments may be readily prepared by, for example, directly synthesizing the fragment by chemical means, as is commonly practiced using an automated oligonucleotide synthesizer. Also, fragments may be obtained by application of nucleic acid reproduction technology, such as PCR™ (exemplified in U.S. Pat. Nos. 4,683,202 and 4,683,195), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and are particularly suitable for isolating MSCRAMM-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal, 1976; Prokop, 1991; and Kuby, 1994, are particularly relevant, providing detailed methods and protocols for molecular biology methods, hybridization and instruction enzyme digestion, plasmid construction, DNA and RNA sequencing mutant construction and analysis and other related methods.

Of course, for some applications, for example, where one desires to prepare mutants employing a mutant primer strand hybridized to an underlying template or where one seeks to isolate MSCRAMM-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

4.5.7 Methods for the Use of Nucleic Acid Sequences

As mentioned, in certain aspects, the DNA sequence information provided by the present disclosure allows for the preparation of relatively short DNA (or RNA) sequences having the ability to specifically hybridize to nucleic acid sequences encoding portions of the sfb, fnbA, or fnbB genes from streptococci such as *S. pyogenes* and *S. dysgalactiae*, or the fnbA or fnbB gene from *S. aureus*, particularly those including the Au and DU epitopes located upstream of the A1–A3 and D1–D4 binding sites, respectively, which the inventors have shown to bind Fn. In these aspects, nucleic acid probes of an appropriate length are prepared based on a consideration of the natural sequence and the size of the particular DNA segment used. Such DNA segments may be those of native Sfb, FnBA, FnBB, FnBPA or FnBPB epitopes, or alternatively, may be DNA sequences which have undergone site-specific mutations to generate any of the novel peptides disclosed herein. The ability of such nucleic acid probes to specifically hybridize to the corresponding sfb, fnA, fnB, fnbA, or fnbB nucleic acid sequences, and particularly those of the Au and A1–A3 sites of *S. dysgalactiae* na or the DU and D1–D4 sites of *S. aureus* genes lend them particular utility in a variety of embodiments. Importantly, the probes can be used in a variety of diagnostic assays for detecting the presence of pathogenic organisms in a given sample, and particularly staphylococci and streptococci. However, other uses are envisioned, including the expression of protein products, the use of the sequence information for the preparation of mutant species primers, or primers for use in preparing other genetic constructions. Such primers may also be used as diagnostic compositions for the isolation and identification of epitope-encoding nucleic acid segments from related bacteria, and in particular, related staphylococci and streptococci.

To provide certain of the advantages in accordance with the present invention, the preferred nucleic acid sequence employed for hybridization studies or assays include sequences that have, or are complementary to, at least an about 14 or 15 to about 20 or so nucleotide stretch of the sequence, although sequences of about 30 to about 50 or so nucleotides are also envisioned to be useful. A size of at least 14–15 or 20 nucleotides in length helps to ensure that the fragment will be of sufficient length to form a duplex molecule that is both stable and selective. Molecules having complementary sequences over stretches greater than 14–15 or 20 bases in length are generally preferred, though, in order to increase stability and selectivity of the hybrid, and thereby improve the quality and degree of specific hybrid molecules obtained. Thus, one will generally prefer to design nucleic acid molecules having sfb-, fnA-, fnB-, fnbA-, or fnbB-gene-complementary stretches of 14–15 to 20–25 nucleotides, or even longer, such as about 30, or about 50, or about 100, or even about 200 nucleotides, where desired. Such fragments may be readily prepared by, for example, directly synthesizing the fragment by chemical means, by application of nucleic acid reproduction technology, such as the PCR™ technology of U.S. Pat. No. 4,683,202, or by introducing selected sequences into recombinant vectors for recombinant production.

The inventors further contemplate that such DNA segments will have utility in the overexpression of Sfb-, FnBA-, FnBB-, FnBPA and FnBPB-derived peptide epitopes described herein, and the preparation of recombinant vectors containing native and site-specific-mutagenized DNA segments comprising particular epitope regions such as the P1–P4 regions from the sfb gene of S. pyogenes; the Au and A1–A3 regions from the fnA-encoded S. dysgalactiae Fn binding protein, the DU and D1–D4 epitope regions of the S. aureus fnbA gene and the B1–B3 regions from the S. aureus fnbB gene.

In that MSCRAMM proteins are expressed by many staphylococcal and streptococcal pathogens, including S. aureus, S. pyogenes, and S. dysgalactiae, this invention will find particular utility as the basis for diagnostic hybridization assays for detecting sfb-, fnA-, fnB-, fnbB-, and fnbA-specific RNA or DNA in clinical samples. Exemplary clinical samples that can be used in the diagnosis of infections are thus any samples that could possibly include bacterial nucleic acid, including middle ear fluid, sputum, bronchoalveolar fluid and the like. Such samples may be of human, murine, equine, bovine, feline, porcine, or canine origins, and may be used in the diagnosis of streptococcal or staphylococcal infections in both human and veterinary subjects. A variety of hybridization techniques and systems are known that can be used in connection with the hybridization aspects of the invention, including diagnostic assays such as those described in U.S. Pat. No. 4,358,535, incorporated herein by reference. Samples derived from non-human mammalian sources, including animals of economic significance such as domestic farm animals, may also provide the basis for clinical specimens, particularly those animals which are susceptible to staphylococcal or streptococcal infection. Examples of such diseases for which aspects of the present invention find particular diagnostic and treatment methods include mastitis in bovines, or for diseases and conditions such as strangles, pneumonias, endometritis, and abortion in equines.

Accordingly, the nucleotide sequences of the invention are important for their ability to selectively form duplex molecules with complementary stretches of the nucleic acid segments encoding MSCRAMM epitopes. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids, for example, one will select relatively low salt and/or high temperature conditions, such as provided by about 0.02 M to about 0.15 M NaCl at temperatures of about 50° C. to about 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, conditions such as about 0.15 M to about 0.9 M salt, at temperatures ranging from about 20° C. to about 55° C. are used. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, one may desire to employ nucleic acid probes to isolate variants from clone banks containing mutated MSCRAMM-encoding clones. In particular embodiments, mutant clone colonies growing on solid media that contain variants of the MSCRAMM-encoding gene, could be identified on duplicate filters using hybridization conditions and methods, such as those used in colony blot assays, to only obtain hybridization between probes containing sequence variants and nucleic acid sequence variants contained in specific colonies. In this manner, small hybridization probes containing short variant sequences of these genes may be utilized to identify those clones growing on solid media that contain sequence variants of the entire genes. These clones can then be grown to obtain desired quantities of the variant nucleic acid sequences or the corresponding antigens.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, that are capable of giving a detectable signal. In preferred diagnostic embodiments, one will likely desire to employ an enzyme tag such as urease, alkaline phosphatase or peroxidase, instead of radioactive or other environmentally undesirable reagents. In the case of enzyme tags, calorimetric indicator substrates are known that can be employed to provide a means visible to the human eye or spectrophotometrically, to identify specific hybridization with pathogen nucleic acid-containing samples.

In other embodiments, it is proposed that the MSCRAMM-derived DNA sequences, or natural or synthetic variants thereof, may be used to provide highly specific and sensitive detection of staphylococcal or streptococcal isolates when used as reagents in polymerase chain reaction (PCR™) assays. In general, by applying the PCR™ technology as set out, e.g., in U.S. Pat. No. 4,683,202, one may utilize the nucleic acid sequences disclosed herein as oligonucleotide probes for the PCR™ amplification of defined regions of particular MSCRAMM-encoding genes, and particularly the FnBP-encoding nucleic acid segment in a sample. The amplified portion of the sequence may then be detected by hybridization with a hybridization probe containing a complementary sequence. In this manner, extremely small concentrations of nucleic acid may detected in a sample utilizing the disclosed nucleic acid sequences.

4.5.8 Methods of Nucleic Acid Delivery and DNA Transfection

In certain embodiments, it is contemplated that the nucleic acid segments disclosed herein will be used to transfect appropriate host cells. Technology for introduction of DNA into cells is well-known to those of skill in the art. Four general methods for delivering a nucleic segment into cells have been described: (1) chemical methods (Graham and Van Der Eb, 1973); (2) physical methods such as microinjection (Capecchi, 1980), electroporation (Wong and Neumann, 1982; Fromm et al., 1985) and the gene gun (Yang et al., 1990); (3) viral vectors (Lu et al., 1993; Eglitis and Anderson, 1988); and (4) receptor-mediated mechanisms (Curiel et al., 1991; Wagner et al., 1992).

4.5.9 Liposomes and Nanocapsules

In certain embodiments, the inventors contemplate the use of liposomes and/or nanocapsules for the introduction of particular peptides or nucleic acid segments into host cells. Such formulations may be preferred for the introduction of pharmaceutically-acceptable formulations of the nucleic acids, peptides, and/or antibodies disclosed herein. The formation and use of liposomes is generally known to those of skill in the art (see for example, Couvreur et al., 1977 which describes the use of liposomes and nanocapsules in the targeted antibiotic therapy of intracellular bacterial infections and diseases). Recently, liposomes were developed with improved serum stability and circulation half-times (Gabizon and Papahadjopoulos, 1988; Allen and Choun, 1987).

Nanocapsules can generally entrap compounds in a stable and reproducible way (Henry-Michelland et al., 1987). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1977; 1988).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of NILVs results in the formation of small unilamellar vesicles (SUVs) with diameters in the range of 200 to 500 C, containing an aqueous solution in the core.

In addition to the teachings of Couvreur et al. (1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

4.5.10 Recombinant Host Cells and Vectors

Particular aspects of the invention concern the use of plasmid vectors for the cloning and expression of recombinant peptides, and particular peptides incorporating either native, or site-specifically mutated MSCRAMM epitopes. The generation of recombinant vectors, transformation of host cells, and expression of recombinant proteins is well-known to those of skill in the art. Prokaryotic hosts are preferred for expression of the peptide compositions of the present invention. Some examples of prokaryotic hosts are *E. coli* strains JM101, XL1-Blue, RR1, LE392, B, X 1776 (ATCC No. 31537), and W3110 (F-, lambda-, prototrophic. ATCC No. 273325). *Enterobacteriaceae* species such as *Salmonella typhimurium* and *Serratia marcescens*, and other Gram-negative hosts such as various *Pseudomonas* species may also find utility in the recombinant expression of genetic constructs disclosed herein.

Alternatively, Gram-positive cocci such as *S. aureus, S. pyogenes, S. dysgalactiae, S. epidermidis, S. zooepidemicus, S. xylosus*, and *S. hominus*, and bacilli such as *Bacillus subtilis* may also be used for the expression of these constructs and the isolation of native or recombinant peptides therefrom.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* may be typically transformed using vectors such as pBR322, or any of its derivatives (Bolivar et al., 1977). pBR322 contains genes for ampicillin and tetracycline resistance and thus provides easy means for identifying transformed cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

Those promoters most commonly used in recombinant DNA construction include the β-lactamase (penicillinase) and lactose promoter systems (Chang et al., 1978; Itakura et al., 1977; Goeddel et al., 1979) or the tryptophan (trp) promoter system (Goeddel et al., 1980). The use of recombinant and native microbial promoters is well-known to those of skill in the art, and details concerning their nucleotide sequences and specific methodologies are in the public domain, enabling a skilled worker to construct particular recombinant vectors and expression systems for the purpose of producing compositions of the present invention.

In addition to the preferred embodiment expression in prokaryotes, eukaryotic microbes, such as yeast cultures may also be used in conjunction with the methods disclosed herein. *Saccharomyces cerevisiae*, or common baker's yeast is the most commonly used among eukaryotic microorganisms, although a number of other species may also be employed for such eukaryotic expression systems. For expression in *Saccharomyces*, the plasmid YRp7, for example, is commonly used (Stinchcomb et al., 1979; Kingsman et al., 1979; Tschemper et al., 1980). This plasmid already contains the trpL gene which provides a selection marker for a mutant strain of yeast lacking the ability to grow in tryptophan, for example ATCC 44076 or PEP4-1 (Jones, 1977). The presence of the trpL lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al, 1980) or other glycolytic enzymes (Hess et al, 1968; Holland et al, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3N of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts in the routine practice of the disclosed methods. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno. VSV, BPV) source, or may be provided by the host cell chromosomal replication mechanism. If the vector is integrated into the host cell chromosome, the latter is often sufficient.

4.5.11 pQE™ pQE™ (Qiagen Inc., Catsworth, Calif.) which results in the production of a fusion protein where the 10–25 amino acid long carrier contains six contiguous histidine residues. The $His_6$ sequence allows the rapid purification on a column of iminodiacetic acid derivatized Sepharose 6B Fast Flow chelated with $Ni^+$ ions. The inventors have shown that this system is a very effective expression system for preparing peptide compositions of the present invention, generating up to 50 mg of pure recombinant protein per liter of *E coli* culture. Overnight cultures of *E. coli* XL1-Blue (Stratagene) harboring the recombinant pFnBD plasmids are diluted 1:50 in 1 L of Luria Broth (Gibco BRL) containing 50 mg/mL ampicillin. *E. coli* cells are grown until the culture reached an $OD_{600}$ of 0.5–0.8. Expression of the rFnBD proteins is then induced by adding IPTG to a final concentration of 0.2 mM. After a three hour induction period, cells are collected by centrifugation, resuspended in 15 mL of Buffer A (5 mM imidazole, 0.5 M NaCl, 20 mM Tris-HCl, pH 7.9) and lysed by passage through a French press twice at 20,000 lb/in$^2$. Cell debris is removed by centrifugation at 50,000×g for 10 min and the supernatant is passed through a 0.45 µM filter. The recombinant proteins are purified by immobilized metal chelate chromatography, using a column of imminodiacetic acid/Sepharose 6B (Sigma, St. Louis, Mo.) charged with $Ni^{2+}$ (Porath et al., 1975; Hochuli et al., 1988). Supernatants from cells producing rFnBD-A or rFnBD-B and rFnBD-D or rFnBD-P are mixed with 1.5 mL and 0.7 mL charged resin respectively. Preliminary experiments revealed that these amounts of resin are optimal for the concentration of recombinant proteins in the supernatant. The mixtures are incubated end-over-end for 15 min. The resins with bound protein are centrifuged (1000×g for 5 min), washed twice with 10 mL Buffer A and transferred to columns. Subsequently the columns are washed with 10–20 mL additional Buffer A, and proteins are eluted with 40 mM imidazole in 20 mM Tris-HCl, 0.5 M NaCl, pH 7.9. Eluted proteins are dialyzed against PBS to remove imidazole. The polyhistidine leader of these rFnBD proteins has a relatively low affinity for the $Ni^{2+}$-chelated column when compared to other polyhistidine fusion proteins produced in our laboratory. If excess charged resin is used the recombinant proteins become contaminated by cellular proteins that have an affinity for the resin and are eluted with 10–50 mM imidazole. By design, the capacity of charged resins used is not quite enough to bind all of the recombinant protein present in the supernatant. This procedure yields 30 mg of rFnBD-A and rFnBD-B and 15 mg rFnBD-D and rFnBD-P of pure material.

4.5.12 pGEX pGEX (Pharmacia, Ltd. Piscataway, N.J.) encodes a fusion protein where the carrier glutathionine-S-transferase allows one-step purification on a column of glutathione-Sepharose (Smith and Johnson, 1988). This system has the advantage of producing peptides which effectively bind to microtiter plates or nitrocellulose membranes used in ELISA or Western blot type assays. In these cases, the pGEX system which generates fusion proteins with a longer carrier protein is a useful alternative expression system. Another advantage of this system, is the availability of selective proteolytic cleavage sites which have been introduced just C-terminal of the carrier, to allow removal of the peptide from the carrier protein once synthesized.

4.5.13 pMAL pMAL (New England Biolabs, Beverly Mass.) encodes a fusion protein with the maltose binding protein which again permits quick affinity purification according to the following procedure: The gene of interest is cloned into the pMALJ-p2 vector (New England Biolabs, Beverly, Mass.) downstream and inflame with the malE signal sequence and gene, which encodes a maltose-binding protein (MBP). The recombinant plasmid is transformed into E. coli and the culture is induced to overproduce the MBP-fusion protein by the addition of IPTG to the culture medium. The MBP-fusion protein can then be purified as described by (Riggs et al., 1992; Maina et al., 1988). Because of the carrier, the expressed fusion protein is transported to the periplasmic space where disulfide bonds can be formed. This system is particularly useful in the production of Fn type I domains, but may also be used to prepare many of the peptides of the present invention.

4.5.14 pBVL pBVL (PharMingen, San Diego, Calif.) which may be used in conjunction with Baculo Gold™ system to transfect insect cells and produce reasonable levels (1–3 mg/l) of recombinant protein in eukaryotic cells. This system is particularly preferred for the production of recombinant versions of host-ligand proteins.

Recombinant proteins so prepared find utility in the present invention in a variety of embodiments, including compositions for immunoassay reagents, antigen preparation for generation of immune responses in susceptible animals, vaccine formulations, and substrates for antibody production for use in passive and active immunization methods. For large-scale preparation of recombinant proteins, the following procedures may be used: Saturated overnight cultures of E. coli JM 101 (supE, ends, sbcB15, hsd R4, rpsL, thi)(lac-proAB) (F'traD36 proAB$^+$ lacI$^q$ Z)M15), E. coli JM105 (supE thi)(lac-proAB) (F'traD36 proAB$^+$ lacI$^q$ Z)M15), TG1 (supE hsd)5 thi)(lac-proAB)$^+$ (F$^+$traD36 proAB lacI$^q$ lacZ(M15)) (Carter et al., 1985), or XL1-Blue cells (Stratagene, La Jolla, Calif.) harboring expression plasmids are diluted 1:50 in Luria Broth (Gibco BRL, Grand Island, N.Y.) supplemented with ampicillin and allowed to grow until the culture reached an OD$_{600}$ of 0.6–0.7. Isopropyl-1-thio-β-D-galactopyranoside (IPTG: Gibco BRL, Grand Island, N.Y.) (final concentration 0.2 mM) is added to the cells and growth continued for another 2.5–5 hr at 37° C. The bacteria are collected by centrifugation and the bacterial pellets are resuspended in phosphate buffered saline (PBS; 10 mM phosphate, 0.14 M NaCl, pH 7.4). The cells are lysed by passage through a French press (SLM Instrument Inc., Urbana, Ill.) twice at 20,000 LB/in. The bacterial lysate is centrifuged at 102,000×g for 10 minutes to remove bacterial debris. The supernatant containing the soluble proteins is filtered through a 0.45 µM membrane (Nalgene, Rochester, N.Y.) and retained for further purification.

4.5.15 Screening Assays

Host cells that have been transformed may be used in the screening of natural and artificially derived compounds or mixtures to select those that are capable of complexing with the FnBPs of the present invention. This could be useful in the search for compounds that inhibit or otherwise disrupt, or even enhance the ability of the microorganism to bind Fn. It is contemplated that effective pharmaceutical agents may be developed by identifying compounds that complex with the particular MSCRAMM epitopes, including, for example, compounds isolated from natural sources, such as plant, animal and marine sources, and various synthetic compounds. Natural or man-made compounds that may be tested in this manner may also include various minerals and proteins, peptides or antibodies.

4.5.16 Site-Specific Mutagenesis

Site-specific mutagenesis is a technique useful in the preparation of individual peptides, or biologically functional equivalent proteins or peptides, through specific mutagenesis of the underlying DNA. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to about 25 nucleotides in length is preferred, with about 5 to about 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double-stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as them are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajai, 1991; Kuby, 1994; and Maniatis et al., 1982, each incorporated herein by reference, for that purpose.

4.5.17 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |

TABLE 1-continued

| Amino Acids | | | Codons | | | | | |
|---|---|---|---|---|---|---|---|---|
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

4.6 Antibody Compositions and Formulations thereof

Antibodies isolated from the antisera are useful for the specific detection of, for example, microorganisms such as streptococci or staphylococci or fibrinogen-binding proteins, or as research tools. The term "antibodies" as used herein includes monoclonal antibodies, polyclonal, chimeric, single chain, bispecific, simianized, and humanized antibodies as well as Fab fragments, including the products of an Fab immunoglobulin expression library.

Means for preparing and characterizing antibodies are well known in the art (See, e.g., Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-bencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep flog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody liter will be removed and the spleen lymphocytes obtained by homogenizing the spleen with a syringe. Typically, a spleen from an immunized mouse contains approximately about $5H\ 10^7$ to about $2H\ 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3x63-Ag8.653, P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4–1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al. (1977). The use of electrically induced fusion methods is also appropriate (Goding, 1986).

Fusion procedures usually produce viable hybrids at low frequencies, about $1\times10^{-6}$ to about $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine nucleotide is used, the media is supplemented with hypoxanthine.

The preferred selection medium is HAT. Only cells capable of operating salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines may also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

The present invention therefore encompasses anti-fibronectin binding protein antibodies and antibody-based compositions, such as antibody conjugates and immunotoxins, that bind to the same antigen as, or at the same epitopic sites as the monoclonal antibodies termed 9C3 and 11A5. Such anti-fibronectin binding protein antibodies may be of the polyclonal or monoclonal type, with monoclonals being generally preferred.

The identification of an antibody that binds to the same antigen as, or at the same epitopes as monoclonal antibodies 9C3 or 11A5 is a fairly straightforward matter. This can be readily determined using any one of variety of immunological screening assays in which antibody competition can be assessed.

For example, where the test antibodies to be examined are obtained from a different source to that of 9C3 or 11A5, e.g., a rabbit, or are even of a different isotype, simple competition assays may be employed in which 9C3 or 11A5 and the test antibodies are premixed and then applied to an antigen composition. By "antigen composition" is meant any composition that contains the antigen recognized by 9C3 and 11A5, a peptide corresponding to amino acids 20–33 of the D3 motif ($D3_{20-33}$; QFGGHNSVDFEEDT; SEQ ID NO:61) from S. aureus fnbA, in an accessible form, including tissue samples and various forms of purified or semi-purified antigens. Thus, protocols based upon immunohistochemical assays, ELISAs and Western blotting are suitable for use in such simple competition studies.

In such embodiments, one would pre-mix the 9C3 or 11A5 antibody with varying amounts of the test antibodies (e.g., 1:1, 1:10 and 1:100) for a period of time prior to applying to an antigen composition, such as a specimen from an animal, an antigen-coated well of an ELISA plate or an antigen adsorbed to a membrane (as in dot blots and Western blots). By using either anti-murine secondary antibodies one will be able to detect only the bound 9C3 or 11A5 antibodies—the binding of which will be reduced by the presence of a test antibody which recognizes the same epitope/antigen as the monoclonal antibodies 9C3 and/or 11A5.

To conduct an antibody competition study between 9C3 and/or 11A5 and any test antibody, one may first label 9C3 or 11A5 with a detectable label, such as, e.g., biotin or an enzymatic, radioactive or fluorescent label, to enable subsequent identification. In these cases, one would incubate the labeled antibodies with the antibodies to be examined (test antibodies) at various ratios (e.g., 1:1, 1:10 and 1:100) and, after a suitable period of time, one would then assay the reactivity of the labeled 9C3 or 11A5 antibodies and compare this with a control value in which no potentially competing (test) antibody was included in the incubation.

The assay may be any one of a range of immunological assays based upon antibody hybridization, and the 9C3 or 11A5 antibodies would be detected by means of detecting their label, e.g., using streptavidin in the case of biotinylated antibodies or by using a chromogenic substrate in connection with an enzymatic label or by simply detecting a radioactive or fluorescent label. An antibody that binds to substantially the same epitope/antigen as 9C3 or 11A5 will be able to effectively compete for binding and thus will significantly reduce 9C3 or 11A5 binding, as evidenced by a reduction in labeled antibody binding. In the present case, after mixing the labeled 9C3 or 11A5 antibodies with the test antibodies, suitable assays to determine the remaining reactivity include, e.g., ELISAs, RIAs, western or dot blots using a peptide corresponding to amino acids 20–33 of the D3 motif ($D3_{20-33}$; QFGGHNSVDFEEDT; SEQ ID NO:61) from S. aureus fnbA, immunoprecipitation of a protein comprising $D3_{20-33}$; ELISAs, RIAs or immunofluorescent staining of recombinant cells expressing a protein comprising $D3_{20-33}$; indirect immunofluorescent staining of microorganisms such as streptococci or staphylococci; reactivity with fibronectin binding protein cell surface determinants by FACS or indirect immunofluorescence.

The reactivity of the labeled 9C3 or 11A5 antibodies in the absence of any test antibody would be the control high value. The control low value would be obtained by incubating the labeled antibodies with unlabelled antibodies of the same type, when competition would occur and reduce binding of the labeled antibodies. A significant reduction in labeled antibody reactivity in the presence of a test antibody is indicative of a test antibody that recognizes the same epitope, i.e., one that "cross-reacts" with the labeled antibody. "A significant reduction" in terms of the present application may be defined as a reproducible (i.e., consistently observed) reduction in binding of 9C3 or 11A5 of at least about 1% at a ratio of about 1:1, or about 10% at a ratio of about 1:100, or more preferably, of between about 20% and about 50% at any ratio between about 1:1 and 1:100.

4.6.1 Blocking Antibodies

In another aspect, the present invention contemplates an antibody that is immunoreactive with a polypeptide of the invention. As stated above, one of the uses for MSCRAMM-derived peptides according to the present invention is to generate antibodies. Reference to antibodies throughout the specification includes whole polyclonal and monoclonal antibodies, and parts thereof, either alone or conjugated with other moieties. Antibody pans include Fab and $F(ab)_2$ fragments and single chain antibodies. The antibodies may be made in vivo in suitable laboratory animals or in vitro using recombinant DNA techniques. An antibody can be a polyclonal or a monoclonal antibody. In a preferred embodiment, an antibody is a polyclonal antibody. Means for preparing and characterizing antibodies are well known in the art (See, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for Sfb-, FnBA-, FnBB-, FnBPA- and FnBPB-derived MSCRAMM epitopes may be prepared using conventional immunization techniques, as will be generally known to those of skill in the art. A composition containing antigenic epitopes of particular Fn-binding MSCRAMMs (either synthetic peptides, site-specifically mutated, or truncated peptides) can be used to immunize one or more experimental animals, such as a rabbit or mouse, which will then proceed to produce specific antibodies against epitope-containing MSCRAMM peptides. Polyclonal antisera may be obtained, after allowing time for antibody generation, simply by bleeding the animal and preparing serum samples from the whole blood.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate mAbs (below).

One of the important features provided by the present invention is a polyclonal sera that is relatively homogenous with respect to the specificity of the antibodies therein. Typically, polyclonal antisera is derived from a variety of different "clones," i.e., B-cells of different lineage. Monoclonal antibodies, by contrast, are defined as coming from antibody-producing cells with a common B-cell ancestor, hence their "mono" clonality.

When peptides are used as antigens to raise polyclonal sera, one expects considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, an antisera that does not react or reacts poorly with the native molecule.

Polyclonal antisera according to present invention is produced against peptides that are predicted to comprise whole, intact epitopes. It is believed that these epitopes are, therefore, more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, i.e., the percentage of clone reacting with the same molecular determinant, is at least 80%. Even higher clonality—90%, 95% or greater—is contemplated.

To obtain monoclonal antibodies, one also initially immunizes an experimental animal, often preferably a mouse, with an MSCRAMM-derived epitope-containing composition. One then, after a period of time sufficient to allow antibody generation, obtains a population of spleen or lymph cells from the animal. The spleen or lymph cells are then fused with cell lines, such as human or mouse myeloma strains, to produce antibody-secreting hybridomas. These hybridomas may be isolated to obtain individual clones which can then be screened for production of antibody to the desired peptide.

Following immunization, spleen cells are removed and fused, using a standard fusion protocol with plasmacytoma cells to produce hybridomas secreting monoclonal antibodies against MSCRAMM-derived epitopes. Hybridomas which produce monoclonal antibodies to the selected antigens are identified using standard techniques, such as ELISA and Western blot methods. Hybridoma clones can then be cultured in liquid media and the culture supernatants purified to provide the MSCRAMM-derived epitope-specific monoclonal antibodies.

It is proposed that the monoclonal antibodies of the present invention will find useful application in standard immunochemical procedures, such as ELISA and Western blot methods, as well as other procedures which may utilize antibody specific to the MSCRAMM epitopes.

Additionally, it is proposed that monoclonal antibodies specific to the particular MSCRAMM-derived peptide may be utilized in other useful applications. For example, their use in immunoabsorbent protocols may be useful in purifying native or recombinant peptide species or synthetic or natural variants thereof.

In general, both poly- and monoclonal antibodies against these peptides may be used in a variety of embodiments. For example, they may be employed in antibody cloning protocols to obtain cDNAs or genes encoding the peptides disclosed herein or related proteins. They may also be used in inhibition studies to analyze the effects of MSCRAMM-derived peptides in cells or animals. Anti-MSCRAMM epitope antibodies will also be useful in immunolocalization studies to analyze the distribution of MSCRAMMs during various cellular events, for example, to determine the cellular or tissue-specific distribution of the MSCRAMM peptides under different physiological conditions. A particularly useful application of such antibodies is in purifying native or recombinant MSCRAMMs, for example, using an antibody affinity column. The operation of all such immunological techniques will be known to those of skill in the art in light of the present disclosure.

4.6.2 Bispecific Antibody Compositions

In general, the preparation of bispecific antibodies is also well known in the art, as exemplified by Glennie et al. (1987). Bispecific antibodies have been employed clinically, for example, to treat cancer patients (Bauer et al., 1991). One method for the preparation of bispecific antibodies involves the separate preparation of antibodies having specificity for different epitopes of one or more fibronectin binding domains from one or more fibronectin binding protein(s).

While numerous methods are known in the art for the preparation of bispecific antibodies, the Glennie et al. (1987) method involves the preparation of peptic F(ab'γ)$_2$ fragments from the two chosen antibodies, followed by reduction of each to provide separate Fab'γ$_{SH}$ fragments. The SH groups on one of the two partners to be coupled are then alkylated with a cross-linking reagent such as o-phenylenedimaleimide to provide free maleimide groups on one partner. This partner may then be conjugated to the other by means of a thioether linkage, to give the desired F(ab'γ)$_2$ heteroconjugate.

Due to ease of preparation, high yield and reproducibility, the Glennie et al. (1987) method is often preferred for the preparation of bispecific antibodies, however, there are numerous other approaches that can be employed and that are envisioned by the inventors. For example, other techniques are known wherein cross-linking with SPDP or protein A is carried out, or a trispecific construct is prepared (Titus et al., 1987; Tutt et al., 1991).

Another method for producing bispecific antibodies is by the fusion of two hybridomas to form a quadroma (Flavell et al., 1991, 1992; Pimm et al., 1992; French et al., 1991; Embleton et al., 1991). As used herein, the term "quadroma" is used to describe the productive fusion of two B cell hybridomas. Using now standard techniques, two antibody producing hybridomas are fused to give daughter cells, and those cells that have maintained the expression of both sets of clonotype immunoglobulin genes are then selected.

A preferred method of generating a quadroma involves the selection of an enzyme deficient mutant of at least one of the parental hybridomas. This first mutant hybridoma cell line is then fused to cells of a second hybridoma that had been lethally exposed, e.g., to iodoacetamide, precluding its continued survival. Cell fusion allows for the rescue of the first hybridoma by acquiring the gene for its enzyme deficiency from the lethally treated hybridoma, and the rescue of the second hybridoma through fusion to the first hybridoma. Preferred, but not required, is the fusion of immunoglobulins of the same isotype, but of a different subclass. A mixed subclass antibody permits the use if an alternative assay for the isolation of a preferred quadroma.

In more detail, one method of quadroma development and screening involves obtaining a hybridoma line that secretes the first chosen mAb and making this deficient for the essential metabolic enzyme, hypoxanthine-guanine phosphoribosyltransferase (HGPRT). To obtain deficient mutants of the hybridoma, cells are grown in the presence of increasing concentrations of 8-azaguanine ($1\times10^{-7}$M to $1\times10^{-5}$M). The mutants are subcloned by limiting dilution and tested for their hypoxanthine/aminopterin/thymidine (HAT) sensitivity. The culture medium may consist of, for example, DMEM supplemented with 10% FCS, 2 mM L-Glutamine and 1 mM penicillin-streptomycin.

A complementary hybridoma cell line that produces the second desired MAb is used to generate the quadromas by standard cell fusion techniques (Galfre et al., 1981), or by using the protocol described by Clark et al. (1988). Briefly, $4.5\times10^7$ HAT-sensitive first cells are mixed with $2.8\times10^7$ HAT-resistant second cells that have been pre-treated with a lethal dose of the irreversible biochemical inhibitor iodoacetamide (5 mM in phosphate buffered saline) for 30 minutes on ice before fusion. Cell fusion is induced using polyethylene glycol (PEG) and the cells are plated out in 96 well microculture plates. Quadromas are selected using HAT-containing medium. Bispecific antibody-containing cultures are identified using, for example, a solid phase isotype-specific ELISA and isotype-specific immunofluorescence staining.

In one identification embodiment to identify the bispecific antibody, the wells of microtiter plates (Falcon, Becton Dickinson Labware) are coated with a reagent that specifically interacts with one of the parent hybridoma antibodies and that lacks cross-reactivity with both antibodies. The plates are washed, blocked, and the supernatants (SNs) to be tested are added to each well. Plates are incubated at room temperature for 2 hours, the supernatants discarded, the plates washed, and diluted alkaline phosphatase-anti-antibody conjugate added for 2 hours at room temperature. The plates are washed and a phosphatase substrate, e.g., p-Nitrophenyl phosphate (Sigma, St. Louis) is added to each well. Plates are incubated, 3N NaOH is added to each well to stop the reaction, and the $OD_{410}$ values determined using an ELISA reader.

In another identification embodiment, microtiter plates pre-treated with poly-L-lysine are used to bind one of the target cells to each well, the cells are then fixed, e.g. using 1% glutaraldehyde, and the bispecific antibodies are tested for their ability to bind to the intact cell. In addition, FACS, immunofluorescence staining, idiotype specific antibodies, antigen binding competition assays, and other methods common in the art of antibody characterization may be used in conjunction with the present invention to identify preferred quadromas.

Following the isolation of the quadroma, the bispecific antibodies are purified away from other cell products. This may be accomplished by a variety of protein isolation procedures, known to those skilled in the art of immunoglobulin purification. Means for preparing and characterizing antibodies are well known in the art (See, e.g., Antibodies: A Laboratory Manual, 1988).

For example, supernatants from selected quadromas are passed over protein A or protein G sepharose columns to bind IgG (depending on the isotype). The bound antibodies are then eluted with, e.g. a pH 5.0 citrate buffer. The elute fractions containing the BsAbs, are dialyzed against an isotonic buffer. Alternatively, the eluate is also passed over an anti-immunoglobulin-sepharose column. The BsAb is then eluted with 3.5 M magnesium chloride. BsAbs purified in this way are then tested for binding activity by, e.g., an isotype-specific ELISA and immunofluorescence staining assay of the target cells, as described above.

Purified BsAbs and parental antibodies may also be characterized and isolated by SDS-PAGE electrophoresis, followed by staining with silver or Coomassie. This is possible when one of the parental antibodies has a higher molecular weight than the other, wherein the band of the BsAbs migrates midway between that of the two parental antibodies. Reduction of the samples verifies the presence of heavy chains with two different apparent molecular weights.

Furthermore, recombinant technology is now available for the preparation of antibodies in general, allowing the preparation of recombinant antibody genes encoding an antibody having the desired dual specificity (Van Duk et al., 1989). Thus, after selecting the monoclonal antibodies having the most preferred binding characteristics, the respective genes for these antibodies can be isolated, e.g., by immunological screening of a phage expression library (Oi and Morrison, 1986; Winter and Milstein, 1991). Then, through rearrangement of Fab coding domains, the appropriate chimeric construct can be readily obtained.

4.6.3 Humanized Antibody Compositions

Humanized monoclonal antibodies are antibodies of animal origin that have been modified using genetic engineering techniques to replace constant region and/or variable region framework sequences with human sequences, while retaining the original antigen specificity. Such antibodies are commonly derived from rodent antibodies with specificity against human antigens. Such antibodies are generally useful for in vivo therapeutic applications. This strategy reduces the host response to the foreign antibody and allows selection of the human effector functions.

The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non-immunogenic in humans and retain substantially the same affinity as the donor immunoglobulin to the antigen, such as a protein or other compound containing an epitope.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations and U.S. Pat. No. 4,867,973 which describes antibody-therapeutic agent conjugates.

U.S. Pat. No. 5,565,332 describes methods for the production of antibodies, or antibody fragments, which have the same binding specificity as a parent antibody but which have increased human characteristics. Humanized antibodies may be obtained by chain shuffling, perhaps using phage display technology, in as much as such methods will be useful in the present invention the entire text of U.S. Pat. No. 5,565,332 is incorporated herein by reference.

4.6.4 Detection of Peptide and Antibody Compositions

It will be further understood that certain of the polypeptides may be present in quantities below the detection limits of typical staining procedures such as Coomassie brilliant blue or silver staining, which are usually employed in the analysis of SDS/PAGE gels, or that their presence may be masked by an inactive polypeptide of similar $M_r$. Although not necessary to the routine practice of the present invention, it is contemplated that other detection techniques may be employed advantageously in the visualization of particular polypeptides of interest. Immunologically-based techniques such as Western blotting using enzymatically-, radiolabel-, or fluorescently-tagged antibodies described herein are considered to be of particular use in this regard. Alternatively, the peptides of the present invention may be detected by using antibodies of the present invention in combination with secondary antibodies having affinity for such primary antibodies. This secondary antibody may be enzymatically- or radiolabeled, or alternatively, fluorescently-, or colloidal gold-tagged. Means for the labeling and detection of such two-step secondary antibody techniques are well-known to those of skill in the art.

4.6.5 Immunoassays

As noted, it is proposed that native and synthetically-derived peptides and peptide epitopes of the invention will find utility as immunogens, e.g., in connection with vaccine development, or as antigens in immunoassays for the detection of reactive antibodies. Turning first to immunoassays, in their most simple and direct sense, preferred immunoassays of the invention include the various types of enzyme linked immunosorbent assays (ELISAs), as are known to those of skill in the art. However, it will be readily appreciated that the utility of MSCRAMM-derived proteins and peptides is not limited to such assays, and that other useful embodiments include RIAs and other non-enzyme linked antibody binding assays and procedures.

In preferred ELISA assays, proteins or peptides incorporating MSCRAMM-derived protein antigen sequences are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antisera, such as bovine serum albumin (BSA) or casein, onto the well. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)Tween™. These added agents also tend to assist in the reduction of nonspecific background. The layered antisera is then allowed to incubate for, e.g., from 2 to 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween™ or borate buffer.

Following formation of specific immunocomplexes between the test sample and the bound antigen, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugated anti-human IgG for a period of time and under conditions that favor the development of immunocomplex formation (e.g., incubation for 2 hours at room temperature in a PBS-containing solution such as PBS-Tween™).

After incubation with the second labeled or enzyme-tagged antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

ELISAs may be used in conjunction with the invention. In one such ELISA assay, proteins or peptides incorporating antigenic sequences of the present invention are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of powdered milk. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immuno-complexed material. A preferred washing procedure includes washing with a solution such as PBS/Tween®, or borate buffer.

Following formation of specific immunocomplexes between the test sample and the bound material, and subsequent washing, the occurrence of even minute amounts of immunocomplexes formed may be determined.

To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

4.6.6 Immunoprecipitation

The anti-MSCRAMM antibodies of the present invention are particularly useful for the isolation of Fn binding protein antigens by immunoprecipitation. Immunoprecipitation involves the separation of the target antigen component from a complex mixture, and is used to discriminate or isolate minute amounts of protein. For the isolation of cell-surface localized proteins such as Sfb, FnBA, FnBB, FnBPA and FnBPB, peptides must be solubilized from the bacterial cell wall by treatment with lysostaphin (S. aureus) or mutanolysin (streptococci), or alternatively, into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g., enzyme-substrate pairs.

4.6.7 Western Blots

The compositions of the present invention will find great use in immunoblot or western blot analysis. The anti-(MSCRAMM-encoded epitope) antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal. Immunologically-based detection methods for use in conjunction with Western blotting include enzymatically-, radiolabel-, or fluorescently-tagged secondary antibodies against the toxin moiety are considered to be of particular use in this regard.

4.7 Therapeutic, Diagnostic, and Immunological Kits

The invention also encompasses MSCRAMM-derived peptide antigen or antibody compositions together with pharmaceutically-acceptable excipients, carriers, diluents, adjuvants, and other components, such as additional peptides, antigens, cell membrane preparations, or even attenuated whole-cell compositions as may be employed in the formulation of particular vaccines.

Using the peptide antigens described herein, the present invention also provides methods of generating an immune response, which methods generally comprise administering to an animal, a pharmaceutically-acceptable composition comprising an immunologically effective amount of an MSCRAMM-derived peptide composition. Preferred animals include mammals, and particularly humans. Other preferred animals include murines, bovines, equines, porcines, canines, and felines. The composition may include partially or significantly purified MSCRAMM-derived peptide epitopes, obtained from natural or recombinant sources, which proteins or peptides may be obtainable naturally or either chemically synthesized, or alternatively produced in vitro from recombinant host cells expressing DNA segments encoding such epitopes. Smaller peptides that include reactive epitopes, such as those between about 30 and about 100 amino acids in length will often be preferred. The antigenic proteins or peptides may also be combined with other agents, such as other staphylococcal or streptococcal peptide or nucleic acid compositions, if desired.

By "immunologically effective amount" is meant an mount of a peptide composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in diagnostic embodiments, and will also have utility in various prophylactic or therapeutic embodiments. Therefore, although these methods for the stimulation of an immune response include vaccination regimens designed to prevent br lessen significant staphylococcal or streptococcal infections, and treatment regimens that may lessen the severity or duration of any infection, it will be understood that achieving either of these end results is not necessary for practicing these aspects of the invention. Such treatment methods may be used particularly for the treatment of infections caused by pathogens such as coagulase-positive staphylococci such as *Staphylococcus aureus*, coagulase-negative staphylococci such as *Staphylococcus epidermidis, Staphylococcus hemolyticus, Streptococcus dysgalactiae, Streptococcus pyogenes*, and related species.

In addition to the therapeutic compositions and methods described above, the proteins, nucleic acid molecules or antibodies are useful for interfering with the initial physical interaction between a pathogen and mammalian host responsible for infection, such as the adhesion of bacteria, particularly gram positive bacteria, to mammalian extracellular matrix proteins on in-dwelling devices or to extracellular matrix proteins in wounds; to block protein-mediated mammalian cell invasion; to block bacterial adhesion between mammalian extracellular matrix proteins and bacterial proteins that mediate tissue damage; and, to block the normal progression of pathogenesis in infections initiated other than by the implantation of in-dwelling devices or surgical techniques.

Further means contemplated by the inventors for generating an immune response in an animal includes administering to the animal, or human subject, a pharmaceutically-acceptable composition comprising an immunologically effective mount of a nucleic acid composition encoding a peptide epitope, or an immunologically effective mount of an attenuated live organism that includes and expresses such a nucleic acid composition. The "immunologically effective mounts" are those amounts capable of stimulating a B cell and/or T cell response.

Immunoformulations of this invention, whether intended for vaccination, treatment, or for the generation of antibodies useful in the detection of staphylococci and streptococci, or prevention of bacterial adhesion to ECM components such as Fn, may comprise site-specifically mutated, truncated, or synthetically-derived antigenic peptide fragments from these proteins. As such, antigenic functional equivalents of the proteins and peptides described herein also fall within the scope of the present invention. An "antigenically functional equivalent" protein or peptide is one that incorporates an epitope that is immunologically cross-reactive with one or more epitopes derived from any of the particular MSCRAMM proteins disclosed (e.g., FnBB, FnBA, FnBPB and FnBPA). Antigenically functional equivalents, or epitopic sequences, may be first designed or predicted and then tested, or may simply be directly tested for cross-reactivity.

In another embodiment, the novel peptides and proteins of the present invention may be used for the detection of antibodies reactive with such peptides in clinical samples such as serum, blood, or other solutions.

The identification or design of suitable MSCRAMM epitopes, and/or their functional equivalents, suitable for use in immunoformulations, vaccines, or simply as antigens (e.g., for use in detection protocols), is a relatively straight-forward matter. For example, one may employ the methods of Hopp, as enabled in U.S. Pat. No. 4,554,101, incorporated herein by reference, that teaches the identification and preparation of epitopes from amino acid sequences on the basis of hydrophilicity. The methods described in several other papers, and software programs based thereon, can also be used to identify epitopic core sequences, for example, Chou and Fasman (1974a,b; 1978a,b; 1979); Jameson and Wolf (1988); Wolf et al. (1988); and Kyte and Doolittle (1982) address this subject. The amino acid sequence of these "epitopic core sequences" may then be readily incorporated into peptides, either through the application of peptide synthesis or recombinant technology.

It is proposed that the use of shorter antigenic peptides, e.g., about 25 to about 50, or even about 15 to 25 amino acids in length, that incorporate DU, D1, D2, or D3 epitopes of the FnBPA protein from *S. aureus* will provide advantages in certain circumstances, for example, in the preparation of vaccines or in immunologic detection assays. Exemplary advantages include the ease of preparation and purification, the relatively low cost and improved reproducibility of production, and advantageous biodistribution.

In still further embodiments, the present invention concerns immunodetection methods and associated kits. It is contemplated that the proteins or peptides of the invention may be employed to detect antibodies having reactivity therewith, or, alternatively, antibodies prepared in accordance with the present invention, may be employed to detect FnBPA proteins or peptides. Either type of kit may be used in the immunodetection of compounds, present within clinical samples, that are indicative of staphylococcal and/or streptococcal infection. The kits may also be used in antigen or antibody purification, as appropriate.

In general, the preferred immunodetection methods will include first obtaining a sample suspected of containing an FnBPA-reactive antibody, such as a biological sample suspected of containing such antibodies, or alternatively, from a clinical sample such as blood, serum, and the like, from a patient, and contacting the sample with a first FnBPA protein or peptide under conditions effective to allow the formation of an immunocomplex (primary immune complex). One then detects the presence of any primary immunocomplexes that are formed.

Contacting the chosen sample with the FnBPA-derived protein or peptide under conditions effective to allow the formation of (primary) immune complexes is generally a matter of simply adding the protein or peptide composition to the sample. One then incubates the mixture for a period of time sufficient to allow the added antigens to form immune complexes with, i.e., to bind to, any antibodies present within the sample. After this time, the sample composition, such as a tissue section, ELISA plate, dot blot or western blot, will generally be washed to remove any non-specifically bound antigen species, allowing only those specifically bound species within the immune complexes to be detected.

The detection of immunocomplex formation is well known in the art and may be achieved through the application of numerous approaches known to the skilled artisan and described in various publications, such as, e.g., Nakamura et al. (1987), incorporated herein by reference. Detection of primary immune complexes is generally based upon the detection of a label or marker, such as a radioactive, fluorescent, biological or enzymatic label, with enzyme tags such as alkaline phosphatase, urease, horseradish peroxidase and glucose oxidase being suitable. The particular antigen employed may itself be linked to a detectable label, wherein one then simply detects this label, thereby allowing the amount of bound antigen present in the composition to be determined.

Alternatively, the primary immune complexes may be detected by means of a second binding ligand that is linked to a detectable label and that has binding affinity for the first protein or peptide. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies and the remaining bound label is then detected.

For diagnostic purposes, it is proposed that virtually any sample suspected of containing either the antibodies or peptides of interest may be employed. Exemplary samples include clinical samples obtained from a patient such as blood or serum samples, bronchoalveolar fluid, ear swabs, sputum samples, middle ear fluid or even perhaps urine samples may be employed. This allows for the diagnosis of meningitis, otitis media, pneumonia, bacteremia and post-partum sepsis. Furthermore, it is contemplated that such embodiments may have application to non-clinical samples, such as in the titering of antibody samples, in the selection of hybridomas, and the like. Alternatively, the clinical samples may be from veterinary sources and may include such domestic animals as cattle, sheep, and goats. Samples from feline, canine, and equine sources may also be used in accordance with the methods described herein.

The methods described herein are useful for diagnosing microbial infections, such as *S. aureus* infections and disease such as upper respiratory tract infections (such as otitis media, bacterial tracheitis, acute epiglottitis, thyroiditis), lower respiratory infections (such as emphysema, lung abscess), cardiac (such as infective endocarditis), gastrointestinal (such as secretory diarrhea, splenic abscess, retroperitoneal abscess), central nervous system (such as cerebral abscess), ocular (such as blepharitis, conjunctivitis, keratitis, endophthalmitis, preseptal and orbital cellulitis, darcryocystitis), kidney and urinary tract (such as epididymitis, intrarenal and perinephric abscess, toxic shock syndrome), skin (such as impetigo, folliculitis, cutaneous abscesses, cellulitis, wound infection, bacterial myositis, bone and joint (such as septic arthritis, osteomyelitis).

The methods involve the steps of obtaining a sample suspected of containing the microbe, for example *S. aureus*. The sample may be taken from an animal, including a human subject, for example from a wound, blood, saliva, tissues, bone, muscle, cartilage, or skin.

The proteins, or active fragments thereof, and antibodies to the proteins are useful for the treatment and diagnosis of bacterial infections, such as *S. aureus* infections, as described above with regard to diagnosis methods; for the development of anti-*S. aureus* vaccines for active or passive immunization; and, when administered as pharmaceutical composition to a wound or used to coat medical devices or polymeric biomaterials in vitro and in vivo, both the proteins and the antibodies are useful as blocking agents to prevent or inhibit the binding of *S. aureus* to the wound site or biomaterials. Preferably, the antibody is modified so that it is less immunogenic in the patient to whom it is administered. For example, if the patient is a human, the antibody may be "humanized" by transplanting the complimentarity determining regions of the hybridoma-derived antibody into a human monoclonal antibody as described (Jones et al., 1986; Tempest et al., 1991).

Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber, posterior chamber or phakic), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the protein, antibody, or active fragment to a surface of the device, preferably an outer surface that would be exposed to a selected microorganism, such as during a *S. aureus* infection. The surface of the device need not be entirely covered by the protein, antibody or active fragment.

In related embodiments, the present invention contemplates the preparation of kits that may be employed to detect the presence of MSCRAMM-derived epitope-specific antibodies in a sample. Generally speaking, kits in accordance with the present invention will include a suitable protein or peptide together with an immunodetection reagent, and a means for containing the protein or peptide and reagent.

The immunodetection reagent will typically comprise a label associated with an MSCRAMM-related protein or peptide, or associated with a secondary binding ligand. Exemplary ligands might include a secondary antibody directed against the first MSCRAMM-related protein or peptide or antibody, or a biotin or avidin (or streptavidin) ligand having an associated label. Detectable labels linked to antibodies that have binding affinity for a human antibody are also contemplated, e.g., for protocols where the first reagent is an MSCRAMM-related peptide that is used to bind to a reactive antibody from a human sample. Of course, as noted above, a number of exemplary labels are known in the art and all such labels may be employed in connection with the present invention. The kits may contain antigen or antibody-label conjugates either in fully conjugated form, in the form of intermediates, or as separate moieties to be conjugated by the user of the kit.

The container means will generally include at least one vial, test tube, flask, bottle, syringe or other container means, into which the antigen may be placed, and preferably suitably allocated. Where a second binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

4.8 Pharmaceutical Compositions

Pharmaceutical compositions containing the proteins, nucleic acid molecules, antibodies, or fragments thereof may be formulated in combination with a pharmaceutical carrier such as saline, dextrose, water, glycerol, ethanol, other therapeutic compounds, and combinations thereof. The formulation should be appropriate for the mode of administration. The compositions are useful for interfering with, modulating, or inhibiting interactions of fibronectin binding proteins with fibronectin, exemplified by *S. aureus* host cell binding with fibronectin.

Suitable methods of administration include, but are not limited to, topical, oral, anal, vaginal, intravenous, intraperitoneal, intramuscular, subcutaneous, intranasal and intradermal administration. For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

The pharmaceutical compositions disclosed herein may be delivered in a variety of methods depending upon the particular application. For oral administration, the compositions may be formulated with an inert diluent or with an assimilable edible carrier, or they may be enclosed in hard- or soft-shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

Alternatively, the pharmaceutical compositions disclosed herein may be administered parenterally, intravenously, intramuscularly, or even intraperitoneally. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenyl, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions wilt be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

4.9 Vaccines

The present invention contemplates vaccines for use in both active and passive immunization embodiments. Immunogenic compositions proposed to be suitable for use as a vaccine may be prepared most readily directly from the novel immunogenic proteins and/or peptide epitopes described herein. Preferably the antigenic material is extensively dialyzed to remove undesired small molecular weight molecules and/or lyophilized for more ready formulation into a desired vehicle.

The preparation of vaccines that contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions, solid forms suitable for solution in, or suspension in, liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

A composition comprising MSCRAMM-derived proteins and/or native or modified epitopic peptides therefrom may also be the basis for human and animal vaccines, so long as the content of endotoxin (LPS) is reduced, eliminated or de-toxified. The preparation of such compositions that are essentially free from endotoxin can be achieved by following the published methodology, for example, U.S. Pat. No. 4,271,147 (incorporated herein by reference) discloses methods for the preparation of *Neisseria meningitidis* membrane proteins for use in vaccines; and describe the preparation of non-toxic protein and polysaccharide compositions essentially free from LPS.

MSCRAMM-derived epitope-based vaccines may be conventionally administered parenterally, by injection, for example, either subcutaneously or intramuscularly. Additional formulations that are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The peptides and/or proteins of the present invention may be formulated into the vaccine as neutral or salt forms. Pharmaceutically acceptable salts, include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines may be administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered will be readily determinable by the skilled practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as C. parvum or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

Of course, in light of the new technology on DNA vaccination, it will be understood that virtually all such vaccination regimens will be appropriate for use with DNA vectors and constructs, as described by Ulmer et al. (1993), Tang et al. (1992), Cox et al. (1993), Fynan et al. (1993), Wang et al. (1993) and Whitton et al. (1993), each incorporated herein by reference. In addition to parenteral routes of DNA inoculation, including intramuscular and intravenous injections, mucosal vaccination is also contemplated, as may be achieved by administering drops of DNA compositions to the nares or trachea. It is particularly contemplated that a gene-gun may be used to deliver an effectively immunizing amount of DNA to the epidermis (Fynan et al. 1993).

4.10 Affinity Chromatography

Affinity chromatography is generally based on the recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are:

(1) that the matrix must specifically-adsorb the molecules of interest;

(2) that other contaminants remain unadsorbed;

(3) that the ligand must be coupled without altering its binding activity;

(4) that the ligand must bind sufficiently tight to the matrix; and (5) that it must be possible to elute the molecules of interest without destroying them.

A preferred embodiment of the present invention is an affinity chromatography method for purification of antibodies from solution wherein the matrix contains MSCRAMM-derived peptide epitopes such as those derived from FnBPA, FnBPB, FnBA, FnBB, or Sfb, covalently-coupled to a Sepharose CL6B or CL4B. This matrix binds the antibodies of the present invention directly and allows their separation by elution with an appropriate gradient such as salt, GuHCl, pH, or urea.

Another preferred embodiment of the present invention is an affinity chromatography method for the purification of peptides and peptide epitopes from solution. A preferred matrix for this method is antibody 9C3 or 11A5 covalently-coupled to Sepharose CL4B. The matrix binds the amino acid compositions of the present invention directly, and allows their separation by elution with a suitable buffer as described above.

4.11 Bacterial Pathogens

The inventors contemplate the methods and compositions of the present invention to be useful in a number of therapeutic and prophylactic treatment regimens. Since several different organisms have been described to express Fn-binding MSCRAMMs, there are therefore a number of potential candidates for intervention. Gram-positive bacteria which are contemplated to be potential candidates include: Staphylococcus aureus, Staphylococcus epidermidis, Staphylococcus hemolyticus, Staphylococcus simulans, Staphylococcus hominus, Staphylococcus lugdunensis, Staphylococcus intermedius, Staphylococcus saprophyticus, Staphylococcus capitis, Staphylococcus warneri Streptococcus pyogenes (Group A), Streptococcus dysgalactiae (Group C), Streptococcus equisimilis (Group C), Streptococcus zooepidemicus (Group C), Streptococcus spp. (Group B), Streptococcus spp. (Group G), Enterococcus faecalis, Pneumocystis carinii, and related species.

Gram-negative species which are also contemplated to be of particular interest include: Escherichia coli, Pseudomonas aeruginosa, Klebsiella pneumoniae, Yersinia sp., Mycobacterium leprae, M. tuberculosis, M. bovis, Treponema denticola, and T. pallidum.

5. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Antibody Compositions which Inhibit Adhesion to Fn: Synthesis of *S. dysgalactiae* FnBA and FnBB-Derived Epitope Analogs Amino acid substitutions are made in synthetic peptides using the methods below to produce peptides which result in a loss of Fn binding activity. Such activity loss is evaluated in the context of the recombinant Fn-binding MSCRAMM protein. Using site-directed mutagenesis systematic changes are made in the appropriate amino acids to mimic the changes made in the synthetic peptides that lead to the loss of Fn binding activity. The Fn binding activity of native and mutated versions of isolated rFnBD-D are compared using previously published procedures (Speziale et al., 1984). Selected recombinant Fn-binding MSCRAMMs and synthetic peptides are then used as antigens to generate blocking antibodies.

5.1.1 Synthesis and Purification of Peptides

Peptides are synthesized on an Advanced ChemTech MPS 396 peptide synthesizer (Louisville, Ky.) using Fmoc (Chang and Meienhofer, 1978) or Boc chemistry (Erickson and Merrifield, 1976). Unless otherwise stated, peptides are purified from the crude preparations by reverse-phase high performance liquid chromatography (HPLC) using a preparative scale C18 column (Vydac 218TP510; The Separation Group, Hesparia, Calif.) and a Waters 625 LC HPLC system (Milford, Mass.) using the methods previously described (Hancock, 1984). The aqueous buffer used for the purification (Buffer A) consisted of 0.11% (vol/vol) phosphoric acid, 0.28% (vol/vol) triethylamine, and 0.25 mM EDTA, pH 6.5. The organic buffer (Buffer B) consisted of 15% (vol/vol) of buffer A in acetonitrile. After reverse-phase chromatography, fractions containing peptide are dialyzed extensively against 50 mM ammonium bicarbonate and lyophilized. These fractions are analyzed for purity by reverse-phase chromatography on an analytical C18 column (Vydac 218TP546). For this purpose, Buffer C consisted of 0.1% (vol/vol) trifluoroacetic acid (TFA) in water, and Buffer D was 0.1% (vol/vol) TFA in 90% (vol/vol) acetonitrile. A gradient of up to 80% Buffer E was used to elute the peptides, which are subsequently dried by roto-evaporation and submitted for either N-terminal sequence analysis or amino acid composition analysis.

Based on the amino acid sequence from the *S. aureus* fnbA gene (GenBank accession #P14738) (Signas et al., 1989), a variety of mutations may be made to produce peptides having altered amino acid residues. Bold residues indicate the proline substitution amino acid changes. The preparation of mutants of Au leads to the altered amino acid sequences described.

Similar mutations may be made in the AU, A1–A3, and B1–B3 domains of the *S. dysgalactiae* fnbA and fnbB genes, and also in the P1–P4 domains of the sfb gene of the related bacterium, *S. pyogenes*, for preparation of mutated epitopes and subsequent generation of blocking antibodies which inhibit Fn binding to *S. pyogenes*. Other regions include repeats in the *S. aureus* fnbB gene, the E1–E3 repeats of *S. equisimilis*, and the G1–G4 repeats of the group G streptococci.

Due to the extensive homology found within the conserved ligand binding regions of a variety of microorganisms, the rationale outlined herein for the *S. aureus*, *S. dysgalactiae* and related bacteria may be used to construct similar mutations in these organisms. Such an effect has been shown by Joh et al., (1994) when they showed that a peptide derived from *S. aureus* D1–D3 inhibited the binding of Fn to *S. dysgalactiae* and *S. pyogenes*. Likewise, a peptide (A1–A3) from *S. dysgalactiae* inhibited the binding of *S. aureus* and *S. pyogenes* to Fn.

5.2 Example 2

Antibody Compositions which Inhibit Adhesion to Fn: Synthesis of *S. aureus* FnBPA-Derived DU and D1–D4 Epitope Analogs In Example 1, the inventors reported the synthesis of epitope analog peptides for use in generating blocking antibodies which recognize various domains of a variety of streptococcal and staphylococcal fibronectin binding proteins. This example describes the preparation of such synthetic epitopes from the Fn binding domains DU, and D1–D4 of the *S. aureus* fbA gene (FIG. 1). The preparation of mutants of DU and D1–D4 leads to the altered amino acid sequences shown below in Table 2.

TABLE 2

| Peptide | SEQ ID NO: | Sequence |
|---|---|---|
| DU wild type | 3 | ADVVEYEEDTNPGGGQVTTESNLVEFDEEST |
| DU mutant | 4 | ADVVEYEEDTNPPGGQVTTESNLVEFDEEST |
| D1 wild type | 5 | QNSGNQSFEEDTEEDKPKYEQGGNIVDIDFDSVPQIHG |
| D1 mutant | 6 | QNSGNQSFEEDTEEDKPKYEQPGNIVDIDFDSVPQIHG |
| D2 wild type | 7 | QNKGNQSFEEDTEKDKPKYEHGGNIIDIDFDSVPHIHG |
| D2 mutant | 8 | QNKGNQSFEEDTEKDKPKYEHPGNIIDIDFDSVPHIHG |
| D3 wild type | 9 | KPSYQFGGHNSVDFEEDTLPK |
| D3 mutant | 10 | KPSYQFPGHNSVDFEEDTLPK |
| D4 wild type | 11 | GQNEGQQTIEEDTTPPIVP |
| D4 mutant | 12 | GQNEGQQTIPEDTTPPIVP |

In addition a number of combinations of single, double, and triple mutations, etc. could be made using the modified codons similar to those shown in Table 2 to produce peptides having multiple mutated amino acid residues.

Amino acid substitutions made from each of the corresponding synthetic peptides were evaluated for their loss of Fn binding activity. These peptides were then used to generate antibodies which result in prevention of Fn binding to bacterial cells both in vitro and in vivo.

5.3 Example 3

Antibody Compositions which Inhibit *S. aureus* Adhesion to Fn: Site-Specific Mutagenesis or DNAs Encoding fbpA-Derived Epitopes The *S. aureus* fnbA DNA segments of the present invention find particular utility in the production of recombinant peptides. These peptides may be native DU or D1–D4 epitopes, or site-specifically-modified DU- or D1–D4-derived peptides. The general techniques of site-specific mutagenesis disclosed herein may be used to prepare nucleic acid segments containing altered DNA sequences. Details for such procedures are given below.

The PCR™ based strand overlap extension (SOE) (Ho et al., 1989) for site-directed mutagenesis is particularly preferred for site-directed mutagenesis of the nucleic acid compositions of the present invention. The techniques of PCR™ are well-known to those of skill in the art, as described hereinabove. The SOE procedure involves a two-step PCR™ protocol, in which a complementary pair of internal primers (B and C) are used to introduce the appropriate nucleotide changes into the wild-type sequence. In two separate reactions, flanking PCR™ primer A (restriction site incorporated into the oligo) and primer D (restriction site incorporated into the oligo) are used in conjunction with primers B and C, respectively to generate PCR™ products AB and CD. The PCR™ products are purified by agarose gel electrophoresis and the two overlapping PCR™ fragments AB and CD are combined with flanking primers A and D and used in a second PCRT™ reaction. The amplified PCR™ product is agarose gel purified, digested with the appropriate enzymes, ligated into an expression vector, and transformed into *E. coli* JM101, XL1-Blue™(Stratagene, LaJolla, Calif.), JM105, or TG1 (Carter et al., 1985) cells. Clones are isolated and the mutations are confirmed by sequencing of the isolated plasmids.

Site-specifically modified DNA segments from the *S. aureus* fnbA gene may then be used to overexpress recombinant peptides and isolate these peptides in large quantities as described in the following examples. Peptides so isolated may then be used in several of the methods described herein, including the generation of an immune response in an animal, and the isolation of antibodies specific for the peptides so produced.

Protein A affinity purified IgG preparations anti-Fn-peps and anti-D3pep were examined for their epitope specificities and ability to inhibit binding of fibronectin to the D repeats of the *S. aureus* fibronectin-binding MSCRAMM, FnBPA. In an ELISA, anti-D3pep antibody interacted primarily with the D3 and D4 sequences. Anti-Fn-peps antibody revealed a broader specificity; it interacted with all the D repeats, albeit with varying affinities.

To test the blocking activities of the antibodies, they were allowed to inhibit binding of glutathione-S transferase fusions (GST) of the D repeats to fibronectin immobilized on a surface. Both of the antibodies inhibited binding of GST-D3 to fibronectin effectively. When GST-D123 was used in the inhibition assay, anti-Fn-peps revealed a strong inhibitory activity whereas anti-D3pep had a marginal effect. The lack of a strong blocking activity in anti-D3pep may reflect its narrow specificity observed in the epitope localization.

Antigen Specifications:

Anti-D3pep IgG were generated by immunizing rabbits with the following synthetic peptide, KPSYQFPGHNSVD-FEEDTLPKV (SEQ ID NO:13). The peptide contains a single amino acid change at position 7 (glycine to proline substitution). The peptide was coupled to keyhole limpet hemocyanin (KLH) prior to immunization.

Anti-Fn-peps IgG were generated by immunizing rabbits with a mixture of the mutant DU (SEQ ID NO:4), D1 (SEQ ID NO:6), D2 (SEQ ID NO:8) and D3 (SEQ ID NO:10) peptides, shown in Table 2 above. All four peptides were individually coupled to KLH then mixed at equal amounts prior to immunization. The corresponding wild type peptides (DU (SEQ ID NO:3), D1 (SEQ ID NO:5), D2 (SEQ ID NO:7) and D3 (SEQ ID NO:9)) are also listed in Table 2.

5.3.1 Antibody Epitope Compositions and Methods of Use

Anti-Fn-peps IgG interacts with all the D repeats, demonstrating a broad specificity which reflects the heterogeneity of the immunogen. A more narrow specificity is observed in anti-D3pep IgG whose major binding sites are located only in D3 and D4.

The locations of the epitopes for anti-Fn-peps and anti-D3pep antibodies were determined both by ELISA and Western blotting. For ELISA, microtiter wells were coated with glutathione-S transferase (GST) fusion proteins containing one or more of the D repeats derived from the *Staphylococcus aureus* fibronectin binding protein, FnBPA (FIG. 4A). The wells were then probed with the antibodies. The standard ELISA procedure used in these studies is as follows:

(1) Incubate the wells of Immulon 2 plates with 100 µl PBS containing 1 µg GST-fusion proteins for 16 hours at 4° C.

(2) Empty the wells and add 100 µl PBS containing 3% BSA. Hold for 1 hour at room temperature and wash the wells 5 times with PBS containing 0.1% Tween 80 (PBST).

(3) Add 100 µl PBSTB (0.1% BSA in PBST) containing 0.1 µg antibody. Hold for 1 hour at room temperature. Wash the wells 5 times with PBSTB. Incubate the wells with 100 µl PBSTB containing 0.05% goat anti-rabbit IgG conjugated with alkaline phosphatase for 1 hour at room temperature. Wash the wells 5 times with PBSTB.

(4) Add 100 µl of 1 mg/ml p-nitrophenyl phosphate in 1 M diethanolamine, 0.5 mM $MgCl_2$, pH 9.8 and hold for 10–20 minutes at room temperature. Measure the intensity of the coloring at 405 nm using a plate reader.

The result (FIG. 4B and FIG. 4C) indicated that anti-Fn-peps recognizes all the D repeats, albeit the reactivities of the repeats varied. On the other hand, anti-D3pep antibody showed relatively narrow specificity. The antibody primarily reacted with the D3 and D4. The high reactivity to GST-D123 was probably due to the presence of the D3 repeat in the recombinant protein.

5.3.2 Effects of the Antibodies in Fibronectin Binding to the D Repeats

Anti-Fn-peps and anti-D3pep antibodies inhibited the interaction between fibronectin and the D repeats effectively.

Anti-Fn-peps and anti-D3pep antibodies were tested for their ability to inhibit binding of GST-D3 or GST-D123 to bovine fibronectin immobilized on microtiter plate wells. The assay procedure utilized is detailed as follows:

(1) Coat the wells of Immulon 2 plates with 100 µl PBS containing 1 µg bovine fibronectin for 16 hours at 4° C.

(2) Empty the wells and add 100 µl PBS containing 3% BSA. Hold for 1 hour at room temperature and wash the wells 5 times with PBS containing 0.1% Tween 80 (PBST).

(3) Add to the wells 100 µl PBSTB containing 0.05% biotinylated GST fusion protein which has been premixed with various amounts of antibody. Hold for 1 hour at room temperature. Then wash the wells 5 times with PBST.

(4) Incubate the wells with 100 μl PBSTB containing streptavidin conjugated with alkaline phosphatase for 1 hour at room temperature for 1 hour. Wash the wells 5 times with PBSTB.

(5) Add 100 μl of 1 mg/ml p-nitrophenyl phosphate in 1 M diethanolamine, 0.5 mM $MgCl_2$, pH 9.8 and incubate for 10–20 minutes at room temperature. Measure the intensity of the color at 405 nm using a ELISA plate reader.

Both of the antibodies inhibited the binding of GST-D3 to fibronectin almost completely at the concentration of 5 mg/ml (FIG. 5A and FIG. 5B). Immunoglobulin from pre-immune serum was used as a control. The inability of the preimmune IgG to inhibit the binding demonstrated the specific activity of anti-Fn-peps and anti-D3pep antibodies.

Anti-D3pep did inhibit the binding of GST-D123 to fibronectin only marginally. However, the interaction between GST-D123 and fibronectin was significantly reduced by anti-Fn-peps. It appears that in the presence of anti-D3pep IgG, GST-D123 binds fibronectin via its D1 and D2 portion, which is likely to be blocked by anti-Fn-peps antibody.

5.4 Example 4

Recombinant Expression of fnbA-Derived Antigens

To overexpress the fnbA-derived MSCRAMMs, and their synthetically-modified peptide derivatives discussed in the previous examples, DNA fragments encoding either the native or genetically-modified epitopic-regions of the fnbA gene of *S. aureus* are cloned into appropriate expression vectors. Such vectors may contain a multiple restriction enzyme cloning site that situates the nucleic acid segment of interest such that its expression is controlled from an inducible promoter. Methods for determining orientation of the inserted segment, induction of the promoter, growth conditions, and restriction enzyme analysis, and recovery of the produced protein are well-known to those of skill in the art. Expression and quantitation of the peptides are determinable via standard methods such as SDS-PAGE, Western blot analysis, and protein determination assays.

The methods used to overexpress the fnbA-derived MSCRAMMs, and their synthetically-modified peptide derivatives can also be used to overexpress other bacterial fibronectin binding proteins, peptides and modified peptide derivatives, including those other peptides from the fnbA or fnbB genes of *S. aureus* described herein below, as well as peptides derived from the fnbA and fnbB genes of *S. dysgalactiae*, or the sfb gene of *S. pyogenes*.

A particular aspect of the present invention is the production of recombinant proteins in large quantity. Such methods are well-known to those of skill in the art, and have been described in detail hereinabove. In an overall and general sense, the production of a large number of recombinant proteins may be produced in either prokaryotic or eukaryotic cells using various expression systems depending upon the particular construct, and the particular advantages of the various expression systems available for such protein production. Particular aspects of the present invention include the use of PQE™ (Qiagen Inc., Catsworth, Calif.), pGEX (Pharmacia, Ltd. Piscataway, N.J.) and pMAL (New England Biolabs, Beverly Mass.), as described in detail herein above.

5.5 Example 5

Circular Dichroism (CD) Analysis of Epitopes

The use of circular dichroism (CD; Woody, 1974) is an important component in the complete analysis of mutant proteins. These data are useful in determining whether or not changes in binding activity are the result of conformational alterations in the mutated protein.

In an important aspect of the invention, the average secondary and tertiary structures of recombinant and mutant proteins are monitored by far- and near-UV circular dichroism (CD) spectroscopy on a Jasco J720 spectropolarimeter. At least four spectra, representing CD data from 190 to 250 nm (far-UV CD) are recorded at 25° C. in a 0.2-mm path length quartz cell and averaged. Likewise, at least four spectra representing CD data from 250 to 320 nm (near-UV CD) are collected at 25° C. in a 1.0-cm path length quartz cell and averaged. The results are expressed as molar ellipticity (deg-$cm^2$/mol). The observed spectra from CBD (30–529) is used as a standard.

5.6 Example 6

Preparation of Antibody Compositions

The synthetic peptides and recombinant peptides described above may be used in the generation of an immune response in an animal and the preparation of antibodies specific for these epitopes. The preparation of antibodies is well known to those of skill in the art as described hereinabove. Briefly, the novel peptides of the present invention are used as antigens in the following manner:

Each peptide is coupled to keyhole limpet hemocyanin (KLH) and used to subcutaneously immunize BALB/c mice. Initial injections contain 250 μg protein and the mice are boosted 7 weeks later with 250 μg of the respective KLH-coupled peptide and then bled 1 week later. The polyclonal antibodies produced by the injected mice are tested for their ability to recognize the native and mutated MSCRAMM in an ELISA assay. The Abs are also assayed for their ability to inhibit Fn binding to isolated MSCRAMMs and intact bacteria using established inhibition assays (Joh et al., 1994). mAbs will be generated from mice producing blocking polyclonal antibodies.

2 mg of KLH is reconstituted with 200 μl of deionized water. 2 mg of the peptide is dissolved in 0.5 ml of conjugation buffer (Pierce Chemical Co., Rockford, Ill.). 500 μl of the peptide solution is added to 200 μl carrier protein solution followed by the addition of 0.5 mg 1-ethyl-3-(3-dimethylaminopropyl) carbodiimide (EDC) in 50 μl of water. The mixtures are incubated at room temperature for 2 hours by end-over-end mixing. The contents of one bottle of the purification buffer salts is dissolved in 60 ml degassed, deionized water. The desalting column is washed with 5 ml of purification buffer, and the peptide carrier mixture is applied directly to the top of the column. 0.5 ml aliquots of wash buffer are added to the column and each fraction is collected in a separate tube. The KLH conjugated peptide are present in the first or second fraction from the column.

Real-time biospecific interaction analysis (BIAcore™; Pharmacia Biosensor AB, La Jolla, Calif.) is used to study the kinetic parameters for the interaction between various recombinant *S. aureus* MSCRAMMs, synthetic peptides, and their ligands. BIAcore™ uses surface plasmon resonance to detect molecular interactions. The ligand can be covalently immobilized on a dextran coated sensorchip using conventional coupling chemistries. Using a microfluidics system, the "analyte" is continuously flowed over the immobilized ligand. Because the biomolecular interactions are recorded in real time, kinetic data such as on rates ($K_{on}$, $\mu M^{-1}s^{-1}$) and off rates ($K_{off}$, $s^{-1}$) in most cases may be obtained. In addition, equilibrium binding constants ($K_d$) may also be calculated. After the analysis, the surface of the chip is regenerated with 5 mM HCl. This effectively removes all bound molecules and allows the next sample to be processed. This technique has permitted the critical evaluation of dissociation, association, and affinity constants of several Gram-positive MSCRAMMs (Joh et al., 1994; Patti et al., 1995).

5.7 Example 7

Passive Immunization Methods Using Modified MSCRAMMs

The antibody compositions disclosed herein find particular utility in the passive immunization of animals to prevent bacterial adhesion to ECM components such as Fn. The site-specifically modified Fn-binding MSCRAMMs described herein are contemplated to be particularly useful as antigens to immunize animal donors, and particularly mammalian donors such as humans. The immunoglobulin fraction (Ig) from the blood plasma of the donors can be purified and systemically administered to a target population. Those individuals at high risk for developing streptococcal and staphylococcal infections include, but are limited to, patients undergoing joint or valve replacements, patients with endocarditis, patients with severe trauma, patients in intensive care units, immunocompromised patients, patients with catheters such as those used for continuous ambulatory peritoneal dialysis (CAPD), surgery patients, vascular grafts, skin grafts and other invasive surgical techniques.

The anti-Fn binding MSCRAMM Ig produced by immunization with peptides of the present invention find particular utility in several areas:

(1) blocking the adhesion of bacteria to Fn-coated substrata;

(2) assisting the immune system in clearance by opsonization; and (3) lysing of bacteria by activation of the classical complement pathway.

5.8 Example 8

Biotin Labeling of S. aureus Strain Cowan and Inhibition of Fn Binding by Mutated Synthetic Peptides S. aureus strain Cowan was cultured under constant rotation for 15 h at 37° C. in brain heart infusion (BHI; Difco) broth. Bacteria were harvested by centrifugation, resuspended in a bicarbonate buffer (50 mM NaHCO$_3$, pH 8.5) to a final density of $10^{10}$ cells/ml determined by comparing the absorbance at 600 nm of the sample with a previously prepared standard curve relating $A_{600}$ to cells counted in a Petroff Hausser chamber. Bacterial cells were labeled with biotin by the addition of 100 μl of 1% NHS-biotin/ml of bacterial suspension (Pierce, Rockford, Ill.) in N,N-dimethylformamide. The staphylococcal cells were incubated with the NHS-biotin for 2 h at room temperature with constant rotation. The biotinylation reaction was stopped by removing the supernatant after centrifugation of the bacterial cells. The bacteria were then washed three times in PBS to remove unincorporated biotin. The bacterial cell suspensions were then adjusted to $1 \times 10^{10}$ cells/ml and the cells were stored at 4° C. in PBS, pH 7.4. To prevent unbiotinylated bacteria from growing and to reduce background, sodium azide and 0.1% BSA were added.

5.8.1 Synthetic Peptides Based on D3 Wild Type from S. Aureus FnBPA

A series of peptides, based on the D3 repeat of S. aureus FnBPA, were synthesized to contain a proline residue at each position throughout the entire sequence (i.e., proline scan; Table 3). The mutated peptides were initially tested for their ability to inhibit biotinylated S. aureus binding to immobilized fibronectin. Wells on a 96-well Immulon II plate were coated with 100 ml of a 30 μg/ml solution of purified Fn, either for 2 hr at room temperature or overnight at 4° C. Wells were washed three times with 1× phosphate buffered saline (PBS)-0.05% Tween-80 and blocked for 1 hr with PBS containing 0.01% Tween-80 and 1% BSA. After 1 hr, wells were washed again with PBS containing 0.05% Tween-80. Synthetic peptides were diluted to 5 mg/ml concentration in 1×PBS and tested at a concentration of 5 (FIG. 2A), 50 (FIG. 2B), or 250 μg/well (FIG. 2C). A volume of 50 ml of the synthetic peptide was added to each well, after 15–25 min, followed by 50 ml of biotinylated S. aureus cells. The plates were incubated for one hour at room temperature with slight agitation on a shaker. After 1 hr the wells were washed with PBS-0.05% Tween-80 and then incubated 30 min in 1:5000 dilution of secondary antibody streptavidin alkaline phosphatase. After 30 min, wells were washed again and developed with diethanolamine containing p-nitrophenyl phosphate (PNPP; 1 mg/ml) for 30 min at room temperature. The reaction was monitored at 405 nm.

TABLE 3

| Peptide | SEQ ID NO: | | Sequence | |
|---|---|---|---|---|
| D3 wild type | 9 | 837 | KPSYQFGGHNSVDFEEDTLPK | 857 |
| 1 | 14 | 837 | PPSYQFGGHNSVDFEEDTLPK | 857 |
| 2 | 15 | 837 | KASYQFGGHNSVDFEEDTLPK | 857 |
| 3 | 16 | 837 | KPPYQFGGHNSVDFEEDTLPK | 857 |
| 4 | 17 | 837 | KPSPQFGGHNSVDFEEDTLPK | 857 |
| 5 | 18 | 837 | KPSYPFGGHNSVDFEEDTLPK | 857 |
| 6 | 19 | 837 | KPSYQPGGHNSVDFEEDTLPK | 857 |
| 7 | 10 | 837 | KPSYQFPGHNSVDFEEDTLPK | 857 |
| 8 | 20 | 837 | KPSYQFGPHNSVDFEEDTLPK | 857 |
| 9 | 21 | 837 | KPSYQFGGPNSVDFEEDTLPK | 857 |
| 10 | 22 | 837 | KPSYQFGGHPSVDFEEDTLPK | 857 |
| 11 | 23 | 837 | KPSYQFGGHNPVDFEEDTLPK | 857 |
| 12 | 24 | 837 | KPSYQFGGHNSPDFEEDTLPK | 857 |
| 13 | 25 | 837 | KPSYQFGGHNSVPFEEDTLPK | 857 |
| 14 | 26 | 837 | KPSYQFGGHNSVDPEEDTLPK | 857 |
| 15 | 27 | 837 | KPSYQFGGHNSVDFPEDTLPK | 857 |
| 16 | 28 | 837 | KPSYQFGGHNSVDFEPDTLPK | 857 |

TABLE 3-continued

| Peptide | SEQ ID NO: | | Sequence | |
|---|---|---|---|---|
| 17 | 29 | 837 | KPSYQFGGHNSVDFEEPTLPK | 857 |
| 18 | 30 | 837 | KPSYQFGGHNSVDFEEDPLPK | 857 |
| 19 | 31 | 837 | KPSYQFGGHNSVDFEEDTPPK | 857 |
| 20 | 32 | 837 | KPSYQFGGHNSVDFEEDTLAK | 857 |
| 21 | 33 | 837 | KPSYQFGGHNSVDFEEDTLPP | 857 |
| 22 | 34 | 837 | PASYQFPPHNSVDFEEDTLPK | 857 |

In addition a number of combinations of single, double, and triple mutations, etc. could be made using the modified codons similar to those shown in 1–21 to produce peptides having multiple mutated amino acid residues.

Similarly altered amino acid sequences of the D1 region are also constructed to yield the mutations shown in Table 4, mutations in D2 are shown in Table 5, mutations in DU shown in Table 6, and mutations in D4 are shown in Table 7. Additionally, the amino acid changes made in A or B may be simultaneously combined with the change in peptide G or H to make the peptide designated V. This technique of combining mutations applies to all of the mutant peptides described in Tables 3–7 to produce a series of synthetic epitopes having either one, two, three or more mutations in a single domain. Likewise single or multiple acidic residues may be changed in each of the epitopes in a similar fashion. Such mutations may be made in DU and/or D1–D4.

TABLE 4

| Peptide | SEQ ID NO: | Sequence (bp 746–783) |
|---|---|---|
| D1 wild type | 5 | QNSGNQSFEEDTEEDKPKYEQGGNIVDIDFDSVPQIHG |
| D1/1 | 35 | QNSGNQSPEEDTEEDKPKYEQGGNIVDIDFDSVPQIHG |
| D1/2 | 36 | QNSGNQSFPEDTEEDKPKYEQGGNIVDIDFDSVPQIHG |
| D1/3 | 37 | QNSGNQSFEPDTEEDKPKYEQGGNIVDIDFDSVPQIHG |
| D1/4 | 38 | QNSGNQSFEEPTEEDKPKYEQGGNIVDIDFDSVPQIHG |
| D1/5 | 39 | QNSGNQSFEEDPEEDKPKYEQGGNIVDIDFDSVPQIHG |
| D1/6 | 40 | QNSGNQSFEEDTPEDKPKYEQGGNIVDIDFDSVPQIHG |
| D1/7 | 41 | QNSGNQSFEEDTEPDKPKYEQGGNIVDIDFDSVPQIHG |
| D1/8 | 42 | QNSGNQSFEEDTEEPKPKYEQGGNIVDIDFDSVPQIHG |
| D1/9 | 6 | QNSGNQSFEEDTEEDKPKYEQPGNIVDIDFDSVPQIHG |
| D1/10 | 43 | QNSGNQSFEEDTEEDKPKYEQGPNIVDIDFDSVPQIHG |
| D1/11 | 44 | QNSGNQSFPPDTEEDKPKYEQPPNIVDIDFDSVPQIHG |

TABLE 5

| Peptide | SEQ ID NO: | Sequence (bp 784–821) |
|---|---|---|
| D2 wild type | 7 | QNKGNQSFEEDTEKDKPKYEHGGNIIDIDFDSVPHIHG |
| D2/1 | 45 | QNKGNQSPEEDTEKDKPKYEHGGNIIDIDFDSVPHIHG |
| D2/2 | 46 | QNKGNQSFPEDTEKDKPKYEHGGNIIDIDFDSVPHIHG |
| D2/3 | 47 | QNKGNQSFEPDTEKDKPKYEHGGNIIDIDFDSVPHIHG |
| D2/4 | 48 | QNKGNQSFEEPTEKDKPKYEHGGNIIDIDFDSVPHIHG |
| D2/5 | 8 | QNKGNQSFEEDTEKDKPKYEHPGNIIDIDFDSVPHIHG |
| D2/6 | 49 | QNKGNQSFEEDTEKDKPKYEHGPNIIDIDFDSVPHIHG |
| D2/7 | 50 | QNKGNQSFPPDTEKDKPKYEHPPNIIDIDFDSVPHIHG |

TABLE 6

| Peptide | SEQ ID NO: | Sequence (bp 860–878) |
|---|---|---|
| D4 wild type | 11 | GQNEGQQTIEEDTTPPIVP |
| D4/1 | 12 | GQNEGQQTIPEDTTPPIVP |
| D4/2 | 51 | GQNEGQQTIEPDTTPPIVP |
| D4/3 | 52 | GQNEGQQTIEEPTTPPIVP |
| D4/4 | 53 | GQNEGQQTPEEDTTPPIVP |

TABLE 7

| Peptide | SEQ ID NO: | Sequence (bp 623–654) |
|---|---|---|
| DU wild type | 3 | ADVVEYEEDTNPGGGQVTTESNLVEFDEEST |
| DU/1 | 4 | ADVVEYEEDTNPPGGQVTTESNLVEFDEEST |
| DU/2 | 54 | ADVVEYEEDTNPGPGQVTTESNLVEFDEEST |
| DU/3 | 55 | ADVVEYPPDTNPPPGQVTTESNLVEFDEEST |

A particular advantage afforded by the use of the Advanced ChemTech MPS396 peptide synthesizer is the ability to create 96 peptides simultaneously. Amino acid substitutions made from each of the corresponding synthetic peptides are evaluated for their loss of Fn binding activity. Such peptides are then used to generate antibodies which result in prevention of Fn binding to bacterial cells both in vitro and in vivo.

5.8.2 Results

The development of high affinity blocking antibodies against the Fn-binding MSCRAMM have been hampered by its "induced-fit" binding mode. Site-specific alterations in the Fn adhesin binding domain that render it unable to bind Fn may lead to an antigen that would produce blocking antibodies. A series of 21 amino acid long peptides were synthesized based on the *S. aureus* D3 repeat motif. In order to maximize the chance of creating a peptide that could not bind Fn, each residue within the 21-mer peptide was serially substituted with proline (Table 3). Proline, which is often found in turns of proteins, is also known to break up the secondary structure of polypeptides. The peptides were then tested for their ability to inhibit *S. aureus* attachment to immobilized Fn in an ELISA.

As shown in FIG. 2A, FIG. 2B, and FIG. 2C, substitution with the proline residue resulted in somewhat unpredictable results. As is most readily apparent in FIG. 2C, generally, the mutant peptides exhibited a decreased ability to inhibit *S. aureus* binding to Fn (peptides 4, 7 from Table 3) however in some cases the inhibitory activity of peptides increased (peptides 1, 2, 3, 8, 11 from Table 3) and in some cases the peptides (peptides 16, 17, 18, 19, 21 from Table 3) actually enhanced *S. aureus* Fn binding ability. Because the *S. aureus* Fn-binding MSCRAMM has three individual binding domains that represent the native Fn-binding MSCRAMM, a vaccine candidate protein must contain site-specific changes in each of the domains.

Based on the ELISA experiments, and because the glycine residue is conserved at the same position within the other binding domains (DU, D1, and D2), an additional series of peptides based on the repeated motifs found in the *S. aureus* Fn-binding MSCRAMM was synthesized that contained a proline substitution at the identical position (Table 8). The new peptides were also analyzed for their ability to inhibit *S. aureus* binding to immobilized Fn. When low concentrations (10 μg) of the peptide derivatives were compared with control samples (no peptide), the D1 and D2 mutant peptides showed no inhibitory activity (FIG. 3A). When increasing concentrations of the mutant peptides were examined (250 μg) inhibitory activity was detected from D1–22P and DU-14P (FIG. 3B), while mutant peptides D2–22P and DU-13P exhibited virtually no inhibitory activity compared to the wild type peptides. These data suggest that the proline substitution has interfered with the overall ability of the peptides to bind Fn.

TABLE 8

| Peptide | SEQ ID NO: | Sequence |
|---------|------------|----------|
| DU wild type | 3 | ADVVEYEEDTNPGGGQVTTESNLVEFDEEST |
| DU 13P | 4 | ADVVEYEEDTNPPGGQVTTESNLVEFDEEST |
| DU 14P | 54 | ADVVEYEEDTNPGPGQVTTESNLVEFDEEST |
| D1 wild type | 55 | QNSGNQSFEEDTEEDKPKYEQGGNIVDIDFSDSVPQIHG |
| D1 22P | 56 | QNSGNQSFEEDTEEDKPKYEQGGNIVDIDFSDSVPQIHG |
| D2 wild type | 57 | QNKGNQSFEEDTEKDKYEHGGNIIDIDFDSVPHIHG |
| D2 22P | 58 | QNKGNQSFEEDTEKDKYEHPGNIIDIDFDSVPHIHG |

5.9 Example 9

Inhibition of Fn-Binding Requires Abs Specific for Certain Epitopes

The present example provides an analysis of the immunological response towards two different forms of recombinant D1–3 immunogen, and demonstrates that to generate antibodies that can inhibit Fn binding to *S. aureus* and Fn-binding MSCRAMMs, the antibodies must be directed against specific epitopes containing the conserved sequence. Furthermore, antibodies specific for this conserved sequence in the C-terminal half of the D3 motif could only be obtained by immunizing with a synthetic peptide containing the desired epitope.

5.9.1 Materials and Methods 5.9.1.1 Bacterial Strains, Plasmids, and Protein Purification FnBP was purified from *S. aureus* strain Newman as described previously (Fröman et al., 1987). Plasmid pGEXD1–3, for expression in *E. coli* of the glutathione S-transferase fusion protein GSTD1–3 has been described elsewhere (Huff et al., 1994). Recombinant D1–3 was purified by treatment of GSTD1–3 with thrombin, followed by ion-exchange chromatography (Huff et al., 1994). Molar extinction coefficients of GSTD1–3 and recombinant D1–3 were used to establish that an absorbance at 280 nm of 1.0 is equivalent to protein concentrations of 0.95 and 3.6 mg/ml respectively. DNA encoding D1–3 was also cloned in the vector pMAL-c2 (New England BioLabs), creating pMALD1–3 for expression in *E. coli* TB1 of a maltose binding fusion protein MBPD1–3. The MBPD1–3 fusion protein was purified from cell lysates by selective ammonium sulfate precipitation, followed by Q-Sepharose and Phenyl-Sepharose (Pharmacia) chromatography employing a Pharmacia Gradi-Frac chromatography system. For purification of antibodies, an affinity matrix was prepared by dissolving the lyophilized fusion protein in 0.5 M sodium bicarbonate (2 mg/ml), and adding an equal volume of carbonyldiimidazole-activated (Bethell et al. 1979) Sepharose CL4B (Pharmacia). After coupling for 48 h at 4° C. with end-over-end mixing, assay of residual protein using the bicinchoninic acid protocol (Smith et al. 1985) established a coupling efficiency of 70%.

5.9.1.2 Preparation of Synthetic Peptide Antigens

Amino acids 21–34 of the D1 motif (D1$_{21-34}$; QGGNIVDIDFDSVP; SEQ ID NO:60) and 20–33 of the D3 motif (D3$_{20-33}$; QFGGHNSVDFEEDT; SEQ ID NO:61) were synthesized with an N-terminal cysteine by the University of Calgary Peptide Synthesis Core Facility, utilizing an Applied Biosystems model 431A peptide synthesizer. The peptides were coupled via the N-terminal cysteine to maleimide-activated Keyhole Limpet Hemocyanin (KLH) or bovine serum albumin (BSA) according to the protocols provided with the Imject Immunogen Conjugation kit (Pierce; Rockford, Ill.).

5.9.1.3 Production of Antisera and Purification of Antibodies

Six male New Zealand White rabbits were immunized subcutaneously with 1 mg of GSTD1–3 in Freunds complete adjuvant (Sigma). Groups of three rabbits were boosted at two week intervals by intramuscular injection of 80 μg of either GSTD1–3, or D1–3 peptide, in incomplete adjuvant. The animals were bled ten days after each immunization, and terminally bled by heart puncture after 128 days. For purification of antibodies, antisera was depleted of Fn by chromatography on gelatin Sepharose (Miekka et al., 1982), then passed over an affinity matrix consisting of MBPD1–3 fusion protein coupled to Sepharose CL4B. After sequential washes with phosphate buffered saline (PBS), and PBS containing 0.5 M sodium chloride, bound antibodies were eluted in 3.5 M MgCl$_2$, dialyzed in 20 mM ammonium bicarbonate, and lyophilized.

For anti-peptide antibodies, each of two male New Zealand White rabbits were immunized subcutaneously with either 100 μg of D1$_{21-34}$ coupled to BSA (D1$_{21-34}$BSA), or D3$_{20-33}$ coupled to KLH (D3$_{20-33}$KLH), emulsified in Freunds complete adjuvant. Booster doses of 100 μg were administered at two week intervals until a plateau in antibody titer was observed. IgG from immune or pre-immune sera were purified on Protein-A agarose (Harlow and Lane, 1987). To prepare F(ab')$_2$ fragments, 20 mg of lyophilized IgG was dissolved in 2 ml of 70 mM sodium acetate, 50 mM NaCl, pH 4.0, and pepsin (Boehringer Mannheim 108 057) was added at a ratio of 30 μg per mg of IgG. After overnight incubation in a 37° C. water bath, Tris buffer pH 8.0 was added to 0.1 M, and F(ab')$_2$ fragments were separated from the pepsin digested Fc fragments by chromatography on a 1.5×90 cm column of Sephacryl S100 (Pharmacia), equilibrated in 50 mM Tris, 150 mM NaCl, 0.02% sodium azide, pH 7.4.

5.9.1.4 ELISA and Epitope Mapping

ELISA was performed in Corning 96 well microtiter plates, with wash buffer consisting of PBS containing 0.05% vol/vol Tween-20, a blocking solution of 3% wt/vol BSA in PBS, and antibody dilution buffer consisting of PBS containing 0.05% Tween-20 and 0.1% BSA. Incubation with primary and secondary antibody was for 60 min at 20° C. on an orbital mixer. Secondary antibody was alkaline phosphatase-conjugated goat anti-rabbit immunoglobulin G, or alkaline phosphatase-conjugated F(ab')$_2$ fragment of F(ab')$_2$-specific goat anti-rabbit IgG (Jackson Immuno Research Laboratories, West Grove Pa.), diluted 5000-fold in antibody buffer. ELISA plates were developed for 60 min at 20° C. with 1 mg/ml p-nitrophenyl phosphate (Sigma) in 0.1 M diethanolamine buffer, pH 9.8, and quantified on a Titertek Multiskan Plus ELISA plate reader equipped with a 405 nm filter. Titters are defined as the dilution of antiserum, or concentration of antibody yielding one-half of the maximal ELISA response (A$_{405}$).

For epitope mapping, overlapping decapeptides spanning the D1 motif, and N-terminal 18 residues of D2 were synthesized by Chiron Mimitopes (Clayton Victoria, Australia), with each consecutive peptide sequence being offset by two amino acids from the previous sequence. A separate set of 15 overlapping decapeptides spanning the D3 motif were also synthesized. Each peptide contained an N-terminal biotin, and a four amino acid spacer sequence consisting of SGSG. Wells of Corning microtiter plates were coated with 100 μl of 5 μg/ml streptavidin (GIBCO/BRL; Gaithersburg, Md.) in distilled, deionized H$_2$O, and allowed to dry on the plates during overnight incubation at 37° C. Blocking and washing procedures were as described for the general ELISA protocol. Biotinylated peptides (2 mg/ml) in 6 M guanidinium hydrochloride were diluted 1000-fold in PBS, and 100 μl aliquots were incubated in the streptavidin-coated microtiter plates for 60 min at 20° C. Plates were then washed and incubated for 60 min with 100 μl of 50 ng/ml affinity purified antibody, diluted in PBS-0.1% BSA-0.05% Tween-20. Plates were then developed as described in the general ELISA protocol.

5.9.1.5 Assay for Inhibition of Fn-Binding

The different antibody preparations were assayed for the ability to inhibit binding of Fn to *S. aureus* cells coated on Corning polystyrene ELISA well strips. Human plasma Fn was obtained from GIBCO/BRL, and labeled with $^{125}$I to a specific activity of 27 MBq/nmol, using the chloramine T procedure (Hunter, 1978). *S. aureus* L857, a blood culture isolate obtained from the University of Manitoba Health Sciences Centre Clinical Microbiology Laboratory, was grown to mid-exponential phase in BHI broth (Difco, Detroit, Mich.) at 37° C. Suspensions of 1×10$^{10}$/ml heat-killed bacteria were prepared as described previously (McGavin et al., 1991), diluted 10-fold in carbonate:bicarbonate buffer, and allowed to coat Corning polystyrene ELISA well strips during overnight incubation at 4° C. with orbital mixing. The wells were washed with PBS containing 0.05% vol/vol Tween-20, and blocked by incubation with 200 μl of 3% wt/vol BSA in PBS for 60 min at 37° C. After washing with PBS-Tween-20, 50 μl of antibody or F(ab')$_2$ inhibitor was added, diluted in PBS containing 0.05% Tween 80 and 0.1% BSA. The cells were pre-incubated with inhibitor for 30 min on an orbital mixer, followed by addition of 50 μl of $^{125}$I-Fn (50,000 cpm) diluted in the same buffer. After an additional 60' incubation, the wells were washed extensively with PBS-0.1% Tween 80, then transferred to Sarstedt 75×12 mm polystyrene centrifuge tubes. The amount of $^{125}$I-Fn bound was then quantified in an LKB Wallac model 1272 automatic gamma counter.

5.9.2 Results 5.9.2.1 Affinity Purification of Abs and Inhibition of Fn-Binding

As measured by ELISA with D1–3 as the test antigen, pooled antisera from animals boosted with GSTD1–3 or recombinant D1–3 yielded maximum titers of 110,000 and 7000 to 9000 respectively. Affinity purification from 300 ml of pooled antisera yielded 35 mg and 7 mg of antibody from antisera generated using the GSTD1–3 and D1–3 immunogens respectively. The affinity purified antibodies exhibited respective titer values of 20 ng/ml and 10 ng/ml (FIG. 6). Therefore, while GSTD1–3 was a better immunogen for eliciting high titer antisera, there was not a dramatic difference in the titters of the affinity purified antibodies. However, the GSTD1–3 fusion protein produced antibodies that were more effective inhibitors of Fn-binding to *S. aureus* (FIG. 7). Dose-dependent inhibition was observed at antibody concentrations from 1 to 20 μg/ml, with 50% inhibition occurring at 20 μg/ml. However, higher concentrations did not promote more than 50% inhibition. For antibodies obtained with the D1–3 immunogen, a concentration of 200 μg/ml was required to achieve 50% inhibition. Therefore, the D1–3 immunogen generated antibodies that were approximately 10-fold less effective as inhibitors of Fn-binding relative to antibodies obtained by immunizing with the fusion protein.

5.9.2.2 Epitope Specificity

Initially, twenty-four decapeptides were synthesized to span the entire D1 motif and the N-terminal 18 amino acids of D2, with each consecutive peptide overlapping by eight amino acids with the previous sequence (Table 9). The D1 and D2 motifs are highly homologous, differing at only 5 of 38 amino acids (Signäs et al., 1989). Therefore, these decapeptides were designed to map dominant epitopes within the D1 motif, and to identify epitopes spanning the C-terminus of D1 and the N-terminus D2. The D1–3 immunogen produced antibodies with a broad spectrum of epitope specificities (FIG. 8A). Most notable was the recognition of epitopes with clusters of acidic amino acids, defined by SFEEDTEEDKPKYE (SEQ ID NO:105; peptides #4–6; Table 9) and SFEEDTEKDKPK (SEQ ID NO:62; peptides #23 and 24; Table 9), spanning residues 7–20 of the D1-motif (D1$_{7-20}$) and D2$_{7-18}$ respectively. Previous work has shown that synthetic peptides D1$_{1-18}$ and D2$_{1-18}$ do not interact with the N-terminal fragment of Fn (Huff et al., 1994). Therefore, this antibody preparation contains a significant population of antibodies specific for amino acid sequences that do not contribute to Fn-binding. There was also more variable recognition of several decapeptides spanning the sequence $D1_{17-38}$.

In contrast, antibodies generated using GSTD1–3 as the immunogen exhibited a restricted specificity, predominantly recognizing three consecutive decapeptides spanning the amino acid sequence $D1_{21-34}$, QGGNIVDIDFDSVP (SEQ ID NO:60; peptides #11–13; Table 9; FIG. 8B). In a previous study, synthetic peptides representing amino acids $D2_{18-38}$ and $D3_{16-36}$ respectively bound the N-terminal fragment of Fn with an affinity comparable to the intact D2 and D3 motifs (Huff et al., 1994). Therefore, the major epitopes recognized by this antibody preparation occur within an amino acid sequence that is critical to Fn-binding. Furthermore, this antibody preparation demonstrated little reactivity towards the clusters of acidic amino acids that were major epitopes for antibodies generated with D1–3 as an immunogen. Neither of the antibody preparations recognized epitopes within an amino acid sequence spanning the C-terminal eight amino acids of the D1 motif, and the first eight amino acids of the D2 motif. Therefore, there appears to be no significant epitopes consisting of amino acid sequences that span two individual motifs.

When assayed with a series of 15 decapeptides spanning the D3 motif (Table 10; FIG. 9A and FIG. 9B), antibodies obtained with the GSTD1–3 immunogen exhibited no appreciable recognition of these peptides (FIG. 9B), while antibodies obtained with the D1–3 immunogen recognized VDFEEDTLPKV (SEQ ID NO:86; peptides #14 and 15; Table 10), representing the C-terminal 11 amino acids of D3 (FIG. 9A). The sequence FEEDT (SEQ ID NO:87) is observed within this 11 amino acid sequence, and also in the two major epitopes within the D1 and D2 motifs that are recognized by this antibody preparation. Therefore, the D1–3 immunogen appears to have generated antibodies with a high specificity for clusters of acidic amino acids, most notably in the N-terminal halves of the D1 and D2 motifs that do not contribute to Fn-binding.

TABLE 9

| Peptide | D1 and/or D2 | SEQ ID NO | Sequence |
|---|---|---|---|
| 1 | D1 | 63 | QNSGNQSFEE |
| 2 | D1 | 64 | SGNQSFEEDT |
| 3 | D1 | 65 | NQSFEEDTEE |
| 4 | D1 | 66 | SFEEDTEEDK |
| 5 | D1 | 67 | EEDTEEDKPK |
| 6 | D1 | 68 | DTEEDKPKYE |
| 7 | D1 | 69 | EEDKPKYEQG |
| 8 | D1 | 70 | DKPKYEQGGN |
| 9 | D1 | 71 | PKYEQGGNIV |
| 10 | D1 | 72 | YFQGGNIVDI |
| 11 | D1 | 73 | QGGNIVDIDF |
| 12 | D1 | 74 | GNIVDIDFDS |
| 13 | D1 | 75 | IVDIDFDSVP |
| 14 | D1 | 76 | DIDFDSVPQI |
| 15 | D1 | 77 | DFDSVPQIHG |
| 16 | D1/D2 | 78 | DSVPQIHGQN |
| 17 | D1/D2 | 79 | VPQIHGQNKG |
| 18 | D1/D2 | 80 | QIHGQNKGNQ |
| 19 | D1/D2 | 81 | HGQNKGNQSF |
| 20 | D2 | 82 | QNKGNQSFEE |
| 21 | D2 | 83 | KGNQSFEEDT |
| 22 | D2 | 84 | NQSFEEDTEK |
| 23 | D2 | 85 | SFEEDTEKDK |
| 24 | D2 | 2 | EEDTEKDKPK |

TABLE 10

| Peptide | SEQ ID NO | Sequence |
|---|---|---|
| D3/1 | 88 | FNKHTEIIEE |
| D3/2 | 89 | KHTEIIEEDT |
| D3/3 | 90 | TEIIEEDTNK |
| D3/4 | 91 | IIEEDTNKDK |
| D3/5 | 92 | EEDTNKDKPS |
| D3/6 | 93 | DTNKDKPSYQ |
| D3/7 | 94 | NKDKPSYQFG |
| D3/8 | 95 | DKPSYQFGGH |
| D3/9 | 96 | PSYQFGGHNS |
| D3/10 | 97 | YQFGGHNSVD |
| D3/11 | 98 | FGGHNSVDFE |
| D3/12 | 99 | GHNSVDFEED |
| D3/13 | 100 | NSVDFEEDTL |
| D3/14 | 101 | VDFEEDTLPK |
| D3/15 | 102 | DFEEDTLPKV |
| $D1_{11-20}$ | 68 | DTEEDKPKYE |
| $D1_{23-32}$ | 74 | GNIVDIDFDS |

5.9.2.3 Use of Synthetic Peptides to Generate Abs of Defined Specificity

The GSTD1–3 immunogen produced antibodies that were effective inhibitors at low concentrations, and exhibited a high specificity for QGGNIVDIDFDSVP (SEQ ID NO:60), spanning the amino acid sequence $D1_{21-34}$. The sequence $D2_{21-34}$ of the D2 motif (HGGNIIDIDFDSVP; SEQ ID NO:103) is nearly identical, suggesting that antibodies specific for these epitopes alone are responsible for the inhibition of Fn-binding to S. aureus. However, the inhibition of Fn-binding was incomplete, and these antibodies exhibited no reactivity towards the sequence QFGGHNSVDFEEDT (SEQ ID NO:61), comprising amino acids 20–33 of the D3 motif ($D3_{20-33}$), and containing amino acids that are known to be critical for Fn-binding (McGavin et al., 1993; McGavin et al., 1991).

To obtain antibodies specific for this sequence, rabbits were immunized with a synthetic peptide $D3_{20-33}$, synthesized with an N-terminal cysteine for coupling to maleimide activated KLH. Rabbits were also immunized with $D1_{21-34}$ coupled to maleimide activated BSA, representing the major epitope recognized by antibodies generated with the GSTD1–3 immunogen. Both anti-peptide antibody preparations recognized the recombinant D1–3 peptide. Although the $D1_{21-34}$ immunogen was coupled to BSA, inclusion of 0.1% BSA in the antibody dilution buffers was sufficient to eliminate interference from recognition of the BSA blocking reagent that was employed in the ELISA assay.

Subsequently, IgG was purified from immune sera utilizing Protein A, and converted into F(ab')$_2$ fragments. The resulting F(ab')$_2$ fragments recognized FnBP purified from *S. aureus* strain Newman (FIG. 10), and a reduction in the ELISA response was observed in the presence of increasing concentrations of soluble competing Fn, such that recognition of FnBP was virtually eliminated at 50 µg/ml of soluble Fn. Consistent with the recognition of epitopes containing amino acid sequences that are critical to Fn-binding, both F(ab')$_2$ preparations exhibited concentration-dependent inhibition of Fn-binding to *S. aureus* cells in the range of 5- to 2000 µg/ml (FIG. 11). At a concentration of 1 mg/ml, the F(ab')$_2$ preparations obtained by immunizing with $D1_{21-34}$ and $D3_{20-33}$ elicited 48.5% and 45.6% inhibition of Fn-binding respectively. However, when mixtures of the two F(ab')$_2$ preparations were assayed for inhibition of Fn-binding at either 100 or 200 µg/ml, the extent of inhibition was not greater than that observed with the same concentrations of either F(ab')$_2$ alone (FIG. 12). Therefore, although the F(ab')$_2$ fragments were specific for epitopes within the D1 and D3 motifs that are critical for Fn-binding, there did not appear to be either an additive or synergistic effect when assayed in combination.

5.9.3. Discussion

The inventors have identified specific amino acid sequences which constitute epitopes for antibodies that inhibit Fn-binding. Antibodies generated with recombinant D1–3 as the immunogen were comparatively poor inhibitors of Fn-binding, and a significant proportion of these antibodies were specific for epitopes in the N-terminal 18 amino acids of the D1 and D2 motifs, which have been shown to exhibit no affinity for Fn (Huff et al., 1994). In contrast, antibodies generated with GSTD1–3 as the immunogen provided dose-dependent inhibition at low concentrations, and were specific primarily for epitopes within the amino acid sequence $D1_{21-34}$. This sequence contains the conserved amino acids, GG and IDF that are essential for Fn-binding by the A2 motif of *S. dysgalactiae*, and present in repeated motifs of several different Fn-binding adhesins from *Staphylococcus* and *Streptococcus* species (McGavin et al., 1993; Patti et al., 1994; Patti and Höök, 1994).

The comparable sequence $D2_{21-34}$ of the D2 motif is nearly identical, therefore, these data establish a correlation between inhibition of Fn-binding, and recognition of epitopes containing a conserved pattern of amino acids that is critical to ligand-binding. However, a limitation associated with both immunogens was the failure to generate antibodies specific for a Fn-binding sequence in the C-terminal half of the D3-motif.

Another study reported that antisera of mice immunized with a D1–3:β-galactosidase fusion protein recognized synthetic peptides representing the D1 and D2 motifs, but failed to recognize D3 (Rozalska et al., 1994). Therefore, similar difficulties have been reported in studies employing different animals and three different forms of D1–3 immunogen.

The inventors have demonstrated that $D1_{21-34}$ was a major epitope for antibodies generated with the GSTD1–3 immunogen, but these antibodies exhibited no appreciable recognition of $D3_{20-33}$ in the D3 motif. The only identity between $D1_{21-34}$ and $D3_{20-33}$ comprises the conserved GG and (I/V) DF sequence motif that is conserved in repeated motifs of other Fn-binding adhesins, and essential for Fn-binding. Therefore, although these two sequences are functionally identical, antibodies specific for $D3_{20-33}$ could not be obtained by immunizing with either D1–3 or GSTD1–3. One explanation for this observation could involve antigen presentation. When D3 is presented as an immunogen as a component of the D1–3 polypeptide, its amino acid sequence divergence from D1 and D2, combined with its 5- to 10-fold greater affinity for Fn (Huff et al., 1994) may contribute to it being less immunogenic.

Furthermore, D1–3 and tandem Fn-binding repeated motifs from other Gram-positive adhesins are essentially unstructured in solution, but undergo a significant rearrangement when complexed with the N-terminal fragment of Fn. Therefore, the interaction of D1–3 with Fn in vivo could either mask epitopes that are critical to ligand binding, interfere with antigen processing, or promote the generation of antibodies specific for amino-acid sequences that are not essential for ligand binding.

Antibodies specific for $D3_{20-33}$ could only be obtained by immunizing with a synthetic peptide corresponding to this specific sequence. In a previous study, it was found that $D3_{20-33}$ could not inhibit binding of Fn to *S. aureus*, but addition of the tripeptide PSY to the N-terminus ($D3_{17-33}$), or LPK to the C-terminus ($D3_{20-36}$) restored Fn-binding function (McGavin et al., 1991). Therefore, although this sequence contains the conserved GG and (I/V)DF amino acids that are essential for Fn-binding, it is by itself unable to bind Fn. It was postulated that $D3_{20-33}$ represents a core sequence that is critical to Fn-binding, but requires three or more N- or C-terminal amino acids to achieve a secondary structure that is favorable for Fn-binding.

Alternatively, it was also suggested that initial contact with Fn might trigger a conformational change necessary for the peptide to maintain contact with the ligand, and that $D3_{20-33}$ was unable to achieve this conformational change. This hypothesis is favored by the observation that D1–3 undergoes a structural rearrangement on contact with the N-terminal fragment of Fn. This may be relevant to many receptor-ligand interactions, and could influence the production of antibodies that inhibit receptor function, as demonstrated when the Fn-binding FnBA adhesin of *S. dysgalactiae* was used as an immunogen. This resulted in a monoclonal antibody that recognized a ligand-induced binding site, and stimulated the ability of peptides containing this sequence to inhibit Fn-binding to *Staphylococcus aureus* cells (Speziale et al, 1996). It was postulated that the ligand-bound conformation of the Fn-binding site was stabilized by the monoclonal antibody.

Since the D1–3 polypeptide is unstructured in solution, binding of polyclonal antibodies to different epitopes may result in a number of unpredictable effects, as evident from the use of synthetic peptides to produce antibodies specific for the catalytic g-subunit of phosphorylase kinase (Wangsgard et at, 1996). Antibodies produced with amino acids 322–346 as an immunogen inhibited phosphorylase activity, whereas activity was stimulated by antibodies specific for the partially overlapping sequence, 342–366.

It has been proposed that during a polyclonal antibody response towards immunogens containing Fn-binding repeated motifs, antibodies that stimulate Fn-binding may compromise the effect of adhesion blocking antibodies, and this may represent a process that has been evolved by bacteria to avoid immunological interference of adherence to Fn (Speziale et al., 1996). In this situation, it would be beneficial to limit the diversity of epitope specificities. This was the rationale in immunizing with synthetic peptides $D1_{21-34}$ and $D3_{20-33}$. This strategy was successful in generating antibodies specific for amino acid sequences that are involved in ligand-binding, as evident from the ability of soluble Fn to compete with the corresponding F(ab')$_2$ preparations for binding to FnBP purified from S. aureus, and from the concentration-dependent inhibition of Fn-binding to S. aureus cells. However, it is not clear why a mixture of the two F(ab')$_2$ preparations did not provide greater inhibition than either one alone. As the peptide sequences $D1_{21-34}$ and $D2_{21-34}$ are nearly identical (Table 8), a mixture of the two F(ab')$_2$ preparations should be sufficient to recognize epitopes that are critical to Fn-binding within each of the three D-motifs. Potential explanations for the failure to observe an additive or a synergistic effect include stearic hindrance considerations, or alternatively, binding of antibody to $D3_{20-33}$ could elicit a conformational change in D1–3 that limits access of antibody to the $D1_{21-34}$ epitope (or vice-versa).

5.10 Example 10

Serum Antibody Response to Fibronectin-Binding MSCRAMM in Patients Diagnosed with *Staphylococcus aureus* Infections This example presents an analysis of the immunological response against Fn-binding MSCRAMM FnBPA of sera from human patients diagnosed with S. aureus infections. The immunodominance of the Fn-binding domain in FnBPA was demonstrated, and a class of antibodies in the sera was identified which recognize epitopes formed on Fn binding (LIBS antibodies). Furthermore, an absence of antibodies that stimulate or inhibit Fn binding to staphylococci was noted.

5.10.1 Materials and Methods

5.10.1.1 Human Sera

Serum specimens from 34 individuals with staphylococcal infections (S. aureus infected) were derived from the Ospedale di Circolo di Varese, Varese, Italy. All the human sera were derived from adult patients. Control IgG was obtained from pooled sera of healthy 2 year-old children. Antibodies from the sera were purified by chromatography on protein A-Sepharose (Pharmacia) and the concentration of the purified IgG was quantitated by absorbance at 280 nm using human IgG as a standard.

5.10.1.2 Isolation and Labeling of Ligands

Human Fn was prepared as previously reported (Vuento and Vaheri, 1979). The N-terminal Fn fragment (N29) was isolated as described (House-Pompeo et al., 1996). The N29 fragment was $^{125}$I-labeled using IODO-BEADS Iodination Reagent as recommended by the manufacturer (Pierce, Rockford, Ill.).

5.10.1.3 Recombinant Proteins: ELISA Assay

Immunoglobulins isolated from human sera were tested for antibodies against FnBPA recombinant proteins in ELISA where microtiter wells (Costar, Cambridge, Mass.) were incubated overnight at 4° C. with 100 µl of 50 mM sodium carbonate, pH 9.5, containing 10 µg/ml protein. Additional protein binding sites in the wells were blocked by incubation for 1 h with 200 µl of 2% (w/v) bovine serum albumin in 10 mM sodium phosphate, pH 7.4, containing 0.13 M sodium chloride (PBS). The wells were then washed 5 times with PBST (0.1% Tween 20 in 150 mM NaCl) and incubated with 2 µg antibody dissolved in 100 µl 2% BSA in PBS at 22° C. Unbound antibody was removed by washing the wells 5 times with PBST. Bound antibody was detected by incubation (1 h at 37° C.) with a peroxidase-conjugated rabbit anti-human IgG (Dako, Gostrup, Denmark) diluted 1:2000. After washing, the conjugated enzyme was reacted with o-phenylenediamine dihydrochloride (Sigma) and the absorbance at 492 nm was monitored in a microplate reader (Bio-Rad).

5.10.1.4 Recombinant Proteins: Fn Binding Assay

Binding of $^{125}$I-N29 to surface-immobilized MSCRAMM was performed in microtiter plates. Wells were coated with 100 µl of GST-Du1234 (10 µg/ml) in 50 mM sodium carbonate, incubated overnight at 4° C. and then subjected to blocking with 200 µl of 2% (w/v) bovine serum albumin in PBS. The wells were subsequently incubated for 2 h at 37° C. with $^{125}$I-labeled N29 ($8\times10^4$ cpm). After extensive washing ($\times 5$) with PBST (PBS containing 0.1% Tween) radioactivity associated with the wells was quantitated in a γ counter. The binding of $^{125}$I-labeled N29 to staphylococci was quantitated as described (Speziale et al., 1996).

5.10.1.5 Isolation of Anti-LIBS Antibodies by Affinity Chromatography on GSTA-DU1234-Sepharose 8 mg of IgG isolated from a patient (I. Z.) were adsorbed on gelatin-Sepharose and not bound material was passed through a column (1×4 cm) of Sepharose 4B substituted with GST-DU1234 recombinant protein and equilibrated with PBS-azide. The column was washed with equilibration buffer until a stable base line of absorbance at 280 nm of the column effluent was observed (flow-through) and then with 0.4 M NaCl in phosphate buffer. The material specifically bound to the column was eluted with 0.1 M glycine, pH 2.8 and the fractions were neutralized with 1M Tris. The unadsorbed material and that bound and eluted from the column were analyzed in ELISA, Western blot and dot blot.

5.10.2 Results

5.10.2.1 Isolation of Anti-LIBS Antibodies

To assess whether the LIBS epitopes are recognized by a specific class of IgG, immunoglobulins isolated from the serum of a patient (I. Z.) were loaded onto a GST-Du124-Sepharose affinity matrix equilibrated with PBS-azide. The column was washed with 10 mM phosphate buffer containing 0.4 M NaCl and proteins adsorbed to the column were eluted with 0.1 M glycine, pH 2.8, neutralized with 1 M Tris and dialyzed against PBS. Analysis by ELISA showed that the IgG purified on the affinity matrix were reactive to GST-Du1234 irrespective of the presence of N29 (FIG. 13C), whereas the non-binding material (flow-through) contained antibodies which predominantly recognized GST-Du1234 only in the presence of N29 (FIG. 13B). Unfractionated material showed an intermediate effect (FIG. 13A).

5.10.2.2 Effect of Antibodies on the Fn Binding to Bacteria

The data described above indicate that the sera from all the patients diagnosed with staphylococcal infections contain antibodies recognizing Fn-induced epitopes. The presence in the sera of blocking antibodies was analyzed by incubating S. aureus cells with $^{125}$I N29 in the presence of IgG isolated from all the patients. None of the antibodies inhibited binding of $^{125}$I-N29 to bacteria (FIG. 14B). Moreover, the IgG did not affect binding of the ligand to recombinant GST-Du1234 segment adsorbed in microtiter wells (FIG. 14A). Thus, the immune response elicited by staphylococcal Fn-binding MSCRAMM does not produce blocking antibodies.

5.11 Example 11

Monoclonal Antibodies to *S. aureus* FnBPA Peptide

This Example describes the production, screening, and inhibitory activity of two monoclonal antibodies, mAb 9C3 and mAb 11A5, which were produced by immunizing mice with the $D3_{20-33}$ peptide derived from FnBPA of *S. aureus*.

A synthetic peptide corresponding to amino acids 20–33 of the D3 motif ($D3_{20-33}$; QFGGHNSVDFEEDT; SEQ ID NO:61) from *S. aureus* fnbA was synthesized with an N-terminal cysteine by the University of Calgary Peptide Synthesis Core Facility, utilizing an Applied Biosystems model 431A peptide synthesizer. The peptide was coupled via the N-terminal cysteine to maleimide-activated Keyhole Limpet Hemocyanin (KLH). Balb/C mice were immunized subcutaneously in the rear footpad with 100 μg of $D3_{20-33}$-KLH peptide emulsified in complete Freund's adjuvant. Three additional injections consisting of 100 μg $D3_{20-33}$-KLH peptide in saline were given on days 4, 8 and 15. On day 16, the mice were sacrificed and the lymphocytes from the politeal lymph nodes were harvested and fused with the mouse myeloma line P3×63-Ag8.653. The cells were cultured in RPMI 1640 HAT medium containing 15% fetal calf serum, penicillin-streptomycin, glutamine and 2-mercaptoethanol.

The hybridomas were screened by ELISA for recognition of $D3_{20-33}$ coupled to BSA 14 days post fusion. Clones reacting to $D3_{20-33}$-BSA were then tested for reactivity to both the wild type peptide $D3_{20-33}$ as well as the recombinant peptide GST-D1–D3 in an ELISA. Two clones designated mAb 9C3 and mAb 11A5 were finally selected and used for ascites production. Both mAbs recognize the sequence SVDFEEDT (SEQ ID NO:104) in the D3 motif Single substitutions of alanine at the S, V, D, E, E or D position result in complete loss of mAb recognition, while substitution at the F or T position has no effect on mAb reactivity.

To determine the inhibition of $^{125}$I-N29 fragment of Fn binding to *S. aureus* fnbA encoded proteins by mAb 9C3, Corning polystyrene ELISA well strips were coated with 1 μg/ml of recombinant proteins D1–3, D2–3, GSTD3 or $1×10^8$ CFU *S. aureus* cells during overnight incubation at 4° C. with orbital mixing. The wells were washed with PBS containing 0.05% vol/vol Tween-20, and blocked by incubation with 200 μl of 3% wt/vol BSA in PBS for 60 min at 37° C. After washing with PBS-Tween-20, 50 μl of antibody inhibitor was added, diluted in PBS containing 0.05% Tween 80 and 0.1% BSA. The wells were pre-incubated with inhibitor for 30 min on an orbital mixer, followed by addition of 50 μl of $^{125}$I-N29 fragment of Fn (50,000 cpm) diluted in the same buffer. After an additional 60 min incubation, the wells were washed extensively with PBS-0.1% Tween 80, then transferred to Sarstedt 75×12 mm polystyrene centrifuge tubes. The amount of $^{125}$I-N29 fragment bound was then quantified in an LKB Wallac model 1272 automatic gamma counter. The results show that mAb 9C3 inhibits the binding of the N29 fragment of Fn to *S. aureus* fnbA encoded proteins in a dose-dependent manner (FIG. 15).

The inhibitory activity of 9C3 and 11A5 monoclonal antibodies was also shown by coating Corning polystyrene ELISA well strips with 1 μg/ml of the recombinant protein GSTD3 during overnight incubation at 4° C. with orbital mixing. The samples were then prepared and analyzed as described above. Both mAb 9C3 and mAb 11A5 were shown to inhibit the binding of the N29 fragment of Fn to *S. aureus* fnbA encoded proteins in a dose-dependent manner (FIG. 16).

5.12 Example 12

Methods for Detecting Passive Immunization Efficacy Animal Models for Endocarditis, Pneumonia and Endophthalmitis The protective efficacy of the antibodies of the present invention may be tested using an in vivo model of endocarditis as described by Moreillon and colleagues (Moreillon et al., 1995). The purified anti-Fn MSCRAMM hyperimmune antibodies (several doses may be used; e.g., ranging from about 100 mg/kg IgG to about 600 mg/kg IgG) may be administered intravenously at various time points (e.g., 21, 14, 7, or 1 day) prior to the infection with *S. aureus* or other staphylococcal species.

Briefly, sterile vegetations are produced in female Wistar rats by inserting a polyethylene catheter via the right carotid artery through the aortic valve. The catheter is secured with silk ligature and left in place for 24 hours. Twenty-four hours after catheterization, rats are inoculated through the tail vein with 0.5 ml saline containing bacterial cells from a culture in the exponential phase of growth. The rats are sacrificed 12 h later, the aortic valves and vegetations excised, weighed, and homogenized in 1 ml of saline, and dilutions are of the homogenate plated for colony counts.

The effectiveness of passive immunization is determined using the pneumonia model as described (Ramisse et al., 1993). According to the Center for Disease Control, *S. aureus* is the second most common organism responsible for lower respiratory infection (Center for Disease Control, 1986). The ability to prevent or minimize pneumonia infection by intravenous or intranasal immunotherapy with anti-Fn binding MSCRAMM Ig (several doses could be used; for example ranging from 100 mg/kg IgG–600 mg/kg IgG) may be tested by administration either pre- or post staphylococcal challenge. 3 week old female BALB/c mice are treated with cyclophosphamide (200 mg/kg intravenous injection) to induce a temporary intense leukopenia. Leukopenia is confirmed by the decrease in the total number of white blood cells as enumerated in an hemocytometer. Immunosuppressed mice are then challenged with *S. aureus* 4 days after cyclophosphamide injection. The mice receive 50 μl of the bacterial inoculum ($6×10^7$ cfu/ml) intranasally. *S. aureus* are cultured in brain heart infusion broth (Difco, Detroit, Mich.) at 37° C. with constant rotation, harvested by centrifugation, and resuspended in sterile phosphate buffered saline (PBS; 10 mM phosphate, 150 mM NaCl, pH 7.4). Bacteria are resuspended to a final density of $6×10^7$ cfu/ml as determined by comparing the $A_{600}$ of the sample with a standard curve relating $A_{600}$ to cell number. The mice are then inoculated intranasally with the bacteria as described above. At selected times following inoculation, mice are sacrificed and the lungs are dissected, homogenized in PBS and the homogenates are serially diluted by plating 100 μl aliquots on blood agar plates. Bacterial counts are determined after growth for 24 hr at 37° C.

Alternatively, the animal model for staphylococcal endophthalmitis is used to determine efficacy of passive immunization methods (Ravindranath et al., 1995). *S. aureus* and *S. epidermidis* are important etiologic agents in the development of postoperative endophthalmitis. Moreover, *S. aureus* endophthalmitis left untreated can quickly lead to the loss of vision (Mao et al., 1993). The ability of anti-Fn MSCRAMM Ig to protect against staphylococcal endophthalmitis can be determined using the model described below. The purified anti-$D3_{20-33}$ epitope MSCRAMM hyperimmune antibodies or 9C3 or 11A5 monoclonal antibodies (several doses may be used; for example ranging from 100 mg/kg IgG to 600 mg/kg IgG) are administered intravenously at various time points (21, 14, 7, or 1 day) prior to the infection with *S. aureus* or other staphylococcal species.

Briefly, staphylococci are cultured in brain heart infusion broth (Difco, Detroit, Mich.) at 37° C. with constant rotation, harvested by centrifugation, and resuspended in sterile phosphate buffered saline (PBS; 10 mM phosphate, 150 mM NaCl, pH 7.4). Bacteria are resuspended to a final density of $1.5 \times 10^8$ cfu/ml as determined by comparing the $A_{600}$ of the sample with a standard curve relating $A_{600}$ to cell number. The suspension is then serially diluted in saline to a concentration of 65 cfu/50 µl for intravitreal injection. Female Lewis rats aged 7 to 8 weeks are anesthetized by inhalation with Metafane™ (methoxyflurane; Pitman-Moore, Mundelein, Ill.)—soaked cotton balls for 5 min. After general anesthesia a drop of proparacaine 0.5% solution (Alcaine R; Alcon, Humanco PR) is applied to the eye. Just before intravitreal injection of bacteria, paracentesis of 5 µl of aqueous humor fluid is performed at the corneoscleral limbus using a 30-Ga needle on a tuberculin syringe to limit intraocular pressure increases and to minimize extrusion of the bacterial inoculum. The right eye of the rat is then injected intravitreally with the 50 µl bacterial suspension and the left eye serves as a control. Several days later (3, 7, 14, 21 etc.) rats are graded by gross external examination and direct ophthalmoscopy then sacrificed. Vitreous humor aspirates (20–25 µl) are collected from each eye using a 20-Ga needle on a tuberculin syringe inserted through the pars plana. The sample is serially diluted and plated on blood agar plates and incubated for 24 hr at 37° C. Bacterial growth after 24 hr is expressed as cfu/ml.

5.13 Example 13

Active Immunization Methods Using Modified MSCRAMMs

The site-specifically modified Fn-binding MSCRAMMs of the present invention are also contemplated to be particularly useful as antigens in a subunit vaccine to immunize animals, and in particular mammals such as humans for protection against staphylococcal infections.

Such methods could also be useful in the veterinary sciences, as the site-specifically modified Fn-binding MSCRAMMs may also be used to immunize animals against infections such as endometritis, mastitis, canine pyoderma, strangles or otitis.

5.14 Example 14

Methods for Detecting Immunization Efficacy: Animal Models for Mastitis

The efficacy of active immunization with the site-specifically modified Fn-binding MSCRAMMs may be tested using a mouse model of mastitis as described (Mamo et al., 1994). Female mice are immunized subcutaneously with 100 µg of the antigen emulsified with Freund's complete adjuvant (Difco). Booster doses are given 14 days later with 50 µg antigen emulsified in Freund's incomplete adjuvant. Mice are then challenged three weeks after the final booster by intramammary inoculation with 0.1 ml of the bacterial suspension ($1 \times 10^6$ cfu/ml) into the left quarter and right quarter mammary glands. The mice are sacrificed 48 hr later and their mammary glands are aseptically removed for histopathological examination and quantification of bacteria. Each dissected mammary gland is placed in a glass tube containing 5 ml of sterile saline and homogenized. Serial dilutions of the homogenates are plated for bacterial counts. The results from these animal trials indicate candidates for use in treating mastitis in cattle.

Alternatively, the animal models for endometritis (Widders et al., 1995) and strangles (a highly-contagious disease of the respiratory tract of horses) (Wallace et al., 1995) may be used to determine effectiveness of the immunization methods. Endometritis refers to genital infections which lead to reproduction failure in horses, and represents a major economic loss to the horse breeding industry. *S. zooepidemicus* is the principal cause of this diseases, with infection rates as high as 54%. Group C streptococci, and predominantly *S. equi*, are the major etiologic agents of strangles, which also has devastating impacts on equine breeders worldwide.

5.15 Example 15

Clinical Detection of Isolates Expressing FnBP MSCRAMMS

One contemplated clinical detection utility is the use of nucleic acid sequences of the present invention as molecular probes for detection of fnA, fnB, fnbA, fnbB, fse and sfb genes in a PCR™-based detection system. The length of the sequence to be detected/amplified is contemplated to range from 50–500 bp. Southern hybridization analysis is readily performed in order to determine the DNA sequences from the region of the particular gene segment used for primers and the DNA sequences to be detected are specific for detecting either chromosomal or plasmid-encoded DNA or RNA sequences. Also, the set or sets of primers selected may also be used to reproducibly prime the synthesis of specific DNA fragments from a variety of different isolates. Sets of primers may be used therefore, in the identification of staphylococcal and streptococcal bacteria in both clinical and non-clinical samples.

For detection, clinical isolate samples (i.e., sputum from lungs, secretions from middle or inner ear, cerebrospinal fluid) are obtained from a patient. The isolate is centrifuged to pellet bacteria. Alternatively, the bacterial sample may be propagated prior to identification by growth on selective media. Bacterial cells are lysed, pelleted, and a sample of the supernatant added to a PCR™ reaction using the FnBP-specific nucleic acid segments disclosed herein. Following amplification, the products are separated via agarose gel electrophoresis and the banding patterns visualized via ethidium bromide. The presence of DNA fragments amplified using such gene-specific primers would indicate the presence of staphylococcal or streptococcal bacteria in the clinical isolate. By using particular nucleic acid segments which are species-specific sequences of the particular MSCRAMM-encoding genes, it is possible to further identify and even speciate the particular bacteria so detected by this method. Compositions comprising novel DNA segments of the present invention, diagnostic kits containing such segments, and methods for the detection of FnBP-encoding nucleic acids are all aspects of the present invention.

5.16 Example 16

Methods for Preventing Bacterial Adhesion to Fn Using Recombinant fnbA-Derived Epitopes Another aspect of the present invention is the use of native and recombinant peptides derived from the fnbA and/or the fnbB genes of *S. aureus* in therapeutic compositions for the prevention of bacterial adhesion to the ECM component Fn. Pharmaceutical compositions are contemplated which are useful in preventing staphylococcal and streptococcal infection in an animal.

Briefly, the introduction of peptide epitopes which recognize and bind Fn into an animal acts as a competitive inhibitor of bacterial adhesion to the same substrate by effectively saturating the available ECM Fn, thereby preventing bacteria expressing FnBPA on its surface from adhering to Fn.

The efficacy of FnBP-derived epitopes' ability to inhibit bacterial adhesion to Fn-coated materials, such as implanted biomaterials, catheters, or vascular grafts can be demonstrated using an in vitro perfusion continuous flow system. Such methods are well-known to those of skill in the art, and described elsewhere in detail (Sapatnekar et al., 1995). Briefly, human blood is continuously pumped over a series of test materials (e.g., hydrophilic polymers, hydrophobic polymers, etc.) in a loop. Tritium-labeled bacteria are then added to the blood and are allowed to interact with the test materials. The test materials are then washed to remove non-adherent bacteria and the remaining bacteria can be quantitated in a 13-counter. The addition of FnBP-derived proteins should lead to a dose-dependent inhibition of bacterial binding to the test materials.

A similar model has been developed by Vaudaux et al. In this model, sterile pieces of tubing (polyvinyl chloride or polyethylene) are sutured into the femoral artery of dogs. The tubing is exposed for varying amounts of time then removed, washed with PBS, and cut into 1.5-cm sections. Each section can be incubated varying amounts of tritium labeled bacteria. The addition of fnbA-derived proteins should lead to a dose-dependent inhibition of bacterial binding to the test materials.

One other potential use could be to covalently couple the fnbA-derived proteins to a catheter or graft. The bound fnbA-derived proteins would then bind Fn at the same site that bacterial normally use, thereby preventing colonization of the biomaterial.

To prepare particular Fn analogs one could use recombinant DNA technology to express the cDNA's in yeast, viruses, or bacterial that encode the amino terminal domain of Fn(N29). The expressed proteins would be purified using standard chromatographic techniques used in the appropriate manner. For example, one could covalently couple the Fn analogs onto a wound dressing. The modified wound dressing is applied to the site of dermal infection (wound) and the bacteria present in the wound site would specifically bind to the wound dressing.

Frequent changing of the modified wound dressing leads to a dramatic reduction in the number of bacteria in the wound thereby minimizing the infection and this should also enhance wound healing.

5.17 Example 17

Antibody Compositions which Inhibit Adhesion to Fn: Site-Specific Mutagensis of DNAs Encoding FnBP Epitopes The *S. dysgalactiae* fnA and fnB DNA segments of the present invention find particular utility in the production of recombinant peptides. These peptides may be native AU or A1–A3 epitopes, or site-specifically-modified AU- or A1–A3-derived peptides. The general techniques of site-specific mutagenesis disclosed hereinabove may be used to prepare nucleic acid segments containing altered DNA sequences. Such segments may then be used to overexpress recombinant peptides and isolate these peptides in large quantities. Peptides so isolated may then be used in several of the methods described herein, including the generation of an immune response in an animal, and the isolation of antibodies specific for the peptides so produced.

In a similar fashion to that shown in Example 2, peptides are synthesized corresponding to the Au, A1–A3 and B1–B3 regions of the *S. dysgalactiae* fnbA and fnB genes and to the P1–P4 regions of the *S. pyogenes* sfb gene. These peptides are contemplated for use in similar aspects of the present invention as those described above for the *S. aureus* fnbA and fnbB peptides.

*----*----*

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

6. REFERENCES

The following literature citations as well as those cited above are incorporated in pertinent part by reference herein for the reasons cited in the above text:

U.S. Pat. No. 3,791,932
U.S. Pat. No. 3,949,064
U.S. Pat. No. 4,174,384
U.S. Pat. No. 4,196,265
U.S. Pat. No. 4,271,147
U.S. Pat. No. 4,358,535
U.S. Pat. No. 4,514,498
U.S. Pat. No. 4,554,101
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251

U.S. Pat. No. 4,683,195
U.S. Pat. No. 4,683,202
U.S. Pat. No. 4,740,467
U.S. Pat. No. 4,965,188
U.S. Pat. No. 5,176,995
Allen and Choun, "Large Unilamellar Liposomes with Low Uptake into the Reticuloendothelial System," *FEBS Lett.*, 223:42–46, 1987.
Baron et al., *Nature*, 345:642–646, 1990.
Bauer, et al., *Vox Sang*, 61:156–157, 1991.
Bayer and Wilchek, "The use of the avidin-biotin complex as a tool for molecular biology" In: *Methods of Biochemical Analysis*, Glick, D., John Wiley and Sons, New York, 1980.
Begley, *Newsweek*, 46–51, Mar. 28, 1994.
Bethell, Ayers, and Hancock, "A novel method of activation of cross-linked agaroses with 1,1'-carbonyldlimidazole which gives a matrix for affinity chromatography devoid of additional charged groups," *J. Biol. Chem.*, 254:2572–2574, 1979.
Bodön and Flock, "Cloning and Characterization of a Gene for a 19 kDa Fibrinogen-Binding Protein from *Staphylococcus aureus*," *Molec. Microbiol.*, 12:599–606, 1994.
Bolivar et al., *Gene*, 2:95, 1977.
Bornstein and Sage, *Ann. Rev. Biochem.*, 49:957–1003, 1980.
Boshart et al., *Cell*, 66:849–859, 1991.
Boyle, "Variation of multifunctional surface binding proteins—a virulence strategy for group A streptococci?" *J. Theor. Biol.* 173:415–426, 1995.
Bozzini et al., "Multiple Binding Sites in Fibronectin and the Staphylococcal Fibronectin Receptor," *Eur. J. Biochem.*, 207:327–333, 1992.
Campbell, "Monoclonal Antibody Technology, Laboratory Techniques in Biochemistry and Molecular Biology," Vol. 13, Burden and Von Knippenberg, Eds., pp. 75–83, Elsevier, Amsterdam, 1984.
Capecchi, "High efficiency transformation by direct microinjection of DNA into cultured mammalian cells," *Cell*, 22(2):479–488, 1980.
Caput et al., *Proc. Natl. Acad. Sci. USA*, 83:1670–1674, 1986.
Carter et al., *Nucl. Acids Res.*, 12:4431–4443, 1985.
Centers for Disease Control, "Nosocomial Infection Surveillance 1984," In: *CDC Surveillance Summaries* 35, 155: 1755–2955, 1986.
Chang and Meienhofer, *Int. J. Peptide Protein Res.*, 11:246–249, 1978.
Chang et al., *Nature*, 375:615, 1978.
Chou and Fasman, "Conformational Parameters for Amino Acids in Helical, β-Sheet, and Random Coil Regions Calculated from Proteins," *Biochemistry*, 13(2):211–222, 1974b.
Chou and Fasman, "Empirical Predictions of Protein Conformation," *Ann. Rev. Biochem.*, 47:251–276, 1978b.
Chou and Fasman, "Prediction of B-Turns," *Biophys. J*, 26:367–384, 1979.
Chou and Fasman, "Prediction of Protein Conformation," *Biochemistry*, 13(2):222–245, 1974a.
Chou and Fasman, "Prediction of the Secondary Structure of Proteins from Their Amino Acid Sequence," *Adv. Enzymol. Relat. Areas Mol. Biol.*, 47:45–148, 1978a.
Chuard et al., "Susceptibility of *Staphylococcus aureus* growing on fibronectin-coated surfaces to bactericidal antibiotics," *Infect. Immun.* 37:625–632, 1993.
Church et al., *Proc. Nat. Acad. Sci. USA*, 81:1991, 1995.

Ciborowski, Flock, and Wadström, "Immunological response to a *Staphylococcus aureus* fibronectin-binding protein," *J. Med. Microbiol.*, 37:376–381, 1992.
Clark et al., *Int. J. Cancer*, 2:15–17, 1988.
Cleary and Retnoningrum, "Group A streptococcal immunoglobulin binding proteins: Adhesins, molecular mimicry, or sensory proteins?" *Trends in Microbiol.*, 2:131–136, 1994.
Couvreur et al., "Nanocapsules, a New Lysosomotropic Carrier," *FEBS Lett.*, 84:323–326, 1977.
Couvreur, "Polyalkyleyanoacrylates as Colloidal Drug Carriers," *Crit. Rev. Ther. Drug Carrier Syst.*, 5:1–20, 1988.
Cox et al., *J. Virol.* 67(9):5664–5667, 1993.
Creighton, "Proteins: Structures and Molecular Properties," 2nd Ed., W. H. Freeman and Co., New York, pp. 287–291, 1992.
Curiel et al., "Adenovirus enhancement of transferrin-polylysine-mediated gene delivery," *Proc. Natl. Acad. Sci. USA*, 88(19):8850–8854, 1991.
Curiel et al., "High-efficiency gene transfer mediated by adenovirus coupled to DNA-polylysine complexes," *Hum. Gen. Ther.*, 3(2):147–154, 1992.
Eglitis and Anderson, "Retroviral vectors for introduction of genes into mammalian cells," *Bio/techniques*, 6(7):608–614, 1988.
Embleton et al., *Br. J. Cancer*, 63(5):670–674, 1991.
Erickson and Merrifield, "Solid-phase peptide synthesis," In: *The Proteins*, vol. II, 3rd Ed., Neurath and Hill, eds., Academic Press, New York, N.Y., pp. 255–527, 1976.
Farrell et al., "Binding of Recombinant Fibrinogen Mutants to Platelets," *J. Biol. Chem.*, 226–231, 1994.
Fattom and Naso, "Staphylococcal vaccines: a realistic dream?" *Ann. Med.*, 28:43–46, 1996.
Fattom, Sarwar, Oritz, and Naso. "A *Staphylococcus aureus* capsular polysaccharide (CP) vaccine and CP-specific antibodies protect mice against bacterial challenge." *Infect. Immun.*, 64:1659–1665, 1996.
Fedson, Shapiro, LaForce, Mufson, Musher, Spika, Breiman, and Broome, "Pneumococcal vaccine after 15 years of use. Another view," *Arch. Intern. Med.*, 154: 2531–2535, 1994.
Fiers et al., *Nature*, 273:113, 1978.
Flavell et al., *Br. J. Cancer*, 64(2):274–280, 1991.
Flavell et al., *Br. J. Cancer*, 65:545–551, 1992.
Flock et al., "Cloning and Expression of the Gene for a Fibronectin-Binding Protein From *Staphylococcus aureus*," *EMBO J.*, 6:2351–2357, 1987.
Frelinger et al., *J. Biol. Chem.*, 265:6346–6352, 1990.
Frelinger et al., *J. Biol. Chem.*, 266:17106–17111, 1991.
French et al., *Cancer Res.*, 51:2358–2361, 1991.
Fröman, Switalski, Speziale, and Höök, "Isolation and characterization of a fibronectin receptor from *Staphylococcus aureus.*" *J. Biol. Chem.*, 262:6564–6571, 1987.
Fromm et al., "Expression of genes transferred into monocot and dicot plant cells by electroporation," *Proc. Natl. Acad. Sci. USA*, 82(17):5824–5828, 1985.
Fynan et al., "DNA vaccines: protective immunizations by parenteral, mucosal, and gene gun inoculations," *Proc. Natl. Acad. Sci. USA* 90(24):11478–11482, 1993.
Gabizon and Papahadjopoulos, "Liposomes formulations with prolonged circulation time in blood and enhanced uptake by tumors," *Proc. Natl. Acad. Sci. USA*, 85:6949–6953, 1988.
Galfre et al., *Methods Enzymol.*, 73:1–46, 1981.
Gefter et al., *Somatic Cell Genet.*, 3:231–236, 1977.
Gill and Hippel, *Anal. Biochem.*, 182:319–326, 1989.
Glennie et al., *J. Immunol.*, 139:2367–2375, 1987.

Goding, "Monoclonal Antibodies: Principles and Practice," pp. 60–74, 2nd Edition, Academic Press, Orlando, Fla., 1986.

Goeddel et al., *Nature*, 281:544, 1979.

Goeddel et al., *Nucl. Acids Res.*, 8:4057, 1980.

Graham and van der Eb, "Transformation of rat cells by DNA of human adenovirus 5," *Virology*, 54(2):536–539, 1973.

Greene and Pace, *J. Biol. Chem.*, 249:5388–5393, 1974.

Greene, McDevitt, Francois, Vaudaux, Lew, and Foster. "Adhesion properties of mutants of *Staphylococcus aureus* defective in fibronectin-binding proteins and studies on the expression of fnb genes." *Mol. Microbiol.* 17:1143–1152, 1995.

Greenfield and Fasman, *Biochemistry*, 8:4108–4116, 1969.

Guner, "Complement evasion by the Lyme disease spirochete *Borrelia burgdorferi* grown in host-derived tissue co-cultures: Role of fibronectin in complement-resistance." *Experientia*, 52:364–372, 1996.

Hanski and Caparon, "Protein F, a fibronectin binding protein, is an adhesin of the group A streptococcus *Streptococcus pyogenes.*" *Proc. Natl. Acad. Sci.*, 89:6172–6176, 1992.

Hansky et al., *Infect. Immun.*, 60:5119–5125, 1992.

Harlow and Lane, "Antibodies: a Laboratory Manual," Cold Spring Harbor Laboratory, Cold Spring Harbor, N.Y. 1988.

Henry-Michelland et al., "Attachment of Antibiotics to Nanoparticles; Preparation, Drag-Release and Antimicrobial Activity in vitro," *Int. J. Pharm.*, 35:121–127, 1987.

Herbert et al., *Ann. Rheum. Dis.*, 46:734–740, 1987.

Hess et al., *J. Adv. Enzyme Reg.*, 7:149, 1968.

Hitzeman et al., *J. Biol. Chem*, 255:2073, 1980.

Ho et al., "Site-Directed Mutagenesis by Overlap Extension Using the Polymerase Chain Reaction," *Gene*, 77:51–59, 1989.

Hochuli et al., *J. Chromatogr.*, 411:177–184, 1988.

Holland et al., *Biochemistry*, 17:4900, 1978.

Homonylo-McGavin et al., "Identification of a *Staphylococcus aureus* Extracellular Matrix-Binding Protein with Broad Specificity," *Infect. and Immun.*, 61:2479–2485, 1993.

House-Pompeo, Xu, Joh, Speziale, and Höök, "Conformational changes in the fibronectin binding MSCRAMMs are induced by ligand binding." *J. Biol. Chem.* 271: 1379–1384, 1996.

Huff, Matsuka, McGavin, and Inghan. "Interaction of N-terminal fragments of fibronectin with synthetic and recombinant D-motifs from its binding protein on *Staphylococcus aureus* studied using fluorescence anisotropy." *J. Biol. Chem.* 269:15563–15570, 1994.

Hunter, "Radioimmunoasssay", In: *Handbook of experimental immunology*, Weir (ed.), Blackwell Scientific Publications, Oxford, p. 14.1–14.40., 1978.

Hynes, "Integrins-Versatility, Modulation, and Signaling in Cell Adhesion," *Cell*, 69:11–2, 1992.

Hynes, *Fibronectins*, Springer-Verlag, New York, 1989.

Itakura et al., *Science*, 198:1056, 1977.

Jameson and Wolf, *Compu. Appl. Biosci.*, 4(1):181–6, 1988.

Joh et al., "Fibronectin Receptors from Gram-Positive Bacteria: Comparison of Active Sites." *Biochemistry*, 33:6086–6092, 1994.

Jones, *Genetics*, 85:12, 1977.

Jones et al., *Nature* 321:522–525, 1986.

Jönsson et al., "A Protein G-Related Cell Surface Protein in *Streptococcus zooepidemicus*," *Infect. and Immun.*, 63:2968–2975, 1995.

Jönsson et al., "*Staphylococcus aureus* Expresses a Major Histocompatibility Complex Class H Analog," *J. Biol. Chem.*, 270:21457–21460, 1995.

Jönsson, "Fibronectin-binding proteins of *Staphylococcus aureus*," Swedish University of Agricultural Sciences (Ph.D. thesis), Uppsala, Sweden, 1992.

Jönsson, Signas, Müller, and Lindberg. "Two different genes encode fibronectin binding proteins in *Staphylococcus aureus*: the complete nucleotide sequence and characterization of the second gene." *Eur. J. Biochem.* 202:1014–1048, 1991.

Kellerman and Ferenci, *Methods Enzymol*, 90:459–463, 1992.

Khan et al., *J. Biol. Chem.*, 263:11314–11318, 1988.

Kingsman et al., *Gene*, 7:141, 1979.

Kline, Xu, Bisno, and Collins, "Identification of a fibronectin-binding protein GfbA in pathogenic group G streptococci." *Infect. Immun.* 64:2122–2129, 1996.

Kohler and Milstein, *Eur. J. Immunol.*, 6:511–519, 1976.

Kohlet and Milstein, *Nature*, 256:495–497, 1975.

Kreikemeyer et al., "Characterization of a Novel Fibronectin-Binding Surface Protein in Group A Streptococci," *Molec. Microbiol.*, 17:137–145, 1995.

Kuby, "Immunology" 2nd Edition, W. H. Freeman & Company, New York, 1994.

Kuna et al., *J. Immunol.*, 150:1932–1943, 1993.

Kuypers and Proctor, "Reduced adherence to traumatized rat heart valves by a low-fibronectin binding mutant of *Staphylococcus aureus.*" *Infect. Immun.* 57:2306–2312, 1989.

Kyte and Doolittle, *J. Mol. Biol.*, 157(1):105–132, 1982.

Lindgren et al., "2 Different Genes Coding for Fibronectin-Binding Proteins From *Streptococcus dysgalactiae*—The Complete Nucleotide Sequences and Characterization of the Binding Domains," *Eur. J. Biochem.*, 214:819–827, 1993.

Lindgren et al., "Cloning and Expression of Two Different Genes From *Streptococcus dysgalactiae* Encoding Fibronectin Receptors," *J. Biol. Chem.*, 267:1924–1931, 1992.

Ljungh et al., "Pathogenesis of wound and biomaterial associated infections," T. Wadstrom, et al., Eds., Springer-Verlag, London, p. 163–168, 1990.

Löfdhal et al, *Proc. Natl. Acad. Sci. USA*, 80:697–701, 1983.

Lu et al., "High efficiency retroviral mediated gene transduction into single isolated immature and replatable CD34(3+) hematopoietic stem/progenitor cells from human umbilical cord blood," *J. Exp. Med.*, 178(6): 2089–2096, 1993.

Luckow and Summers, *Virology*, 170:31–39.

Maina et al., *Gene*, 74:365–373.

Maloy et al., "Microbial Genetics" 2nd Edition, Jones and Bartlett Publishers, Boston, Mass. 1994.

Maloy, "Experimental Techniques in Bacterial Genetics", Jones and Bartlett Publishers, Boston, Mass. 1990.

Mamo et al., *Vaccine*, 12:988–992, 1994.

Maniatis et al., "Molecular Cloning: a Laboratory Manual," Cold Spring Harbor Laboratory, Cold Spring Harbor, N.Y., 1982.

Mao et al., "Endophthalmitis caused by *Staphylococcus aureus*," *Am. J. Ophthalmol.* 116:584–589, 1993.

McDevitt et al., "Genetic Evidence That Bound Coagulase of *Staphylococcus aureus* is not Clumping Factor," *Infect. Immun.*, 60:1514–1523, 1992.

McDevitt et al., "Molecular Characterization of the Clumping Factor (Fibrinogen Receptor) of *Staphylococcus aureus*," *Molec. Microbiol.*, 11:237–248, 1994. McGavin, Gurusiddappa, Lindgren, Lindberg, and Höök, "Fibronectin receptors from *Streptococcus dysgalactiae* and *Staphylococcus aureus*: Involvement of conserved residues in ligand binding." *J. Biol. Chem.* 268:23946–23953, 1993.

McGavin, Raucci, Gurusiddappa, and Höök. "Fibronectin binding determinants of the *Staphylococcus aureus* fibronectin receptor." *J. Biol. Chem.* 266:8343–8347, 1991.

Miekka, Ingham, and Menache, "Rapid methods for isolation of human plasma fibronectin." *Thromb. Res.*, 27:1–14, 1982.

Moreillon et al., "Role of *Staphylococcus aureus* Coagulase and Clumping Factor in the Pathogenesis of Experimental Endocarditis," *Infect. and Immun.*, 1995.

Mosher and Proctor, "Binding of Factor XIIIa-mediated Cross Linking of a 27-kilodalton Fragment of Fibronectin to *Staphylococcus aureus*," *Science*, 209:927–929, 1980.

Myers et al., *Neurochem. Res.*, 18:667–673, 1993.

Nakamura et al., "Enzyme Immunoassays: Heterogenous and Homogenous Systems," Chapter 27, 1987.

Nelson et al., "New insights into the pathogenesis of mastitis," C. Vurvenich, G. Vandepultevan Messon, and A. Hill, Eds., Rijkesuniversiteit, Ghent, p. 111–125, 1991.

Noble, Virani, and Cree, "Co-transfer of vancomycin and other resistance genes from *Enterococcus faecalis* NCTC 12201 to *S. aureus*." *FEMS Microbiol. Lett.* 93:195–198, 1992.

Odermatt et al., *J. Mol. Biol.*, 159:109–123, 1982.

Oi and Morrison, *Mt. Sinai J. Med.*, 53(3):175–180, 1986.

Okada, Pentland, Falk, and Caparon, "M protein and protein F act as important determinants of cell-specific tropism of *Streptococcus pyogenes* in skin tissue." *J. Clin. Invest.* 94:965–977, 1994.

Ozeri. Tovi. Burstein, Natanson-Yaron, Caparon. Yamada, Akiyama, Vlodavsky, and Hanski, "A two-domain mechanism for group A streptococcal adherence through protein F to the extracellular matrix." *EMBO J.* 15:989–998, 1996.

Park et al., *Protein Sci.*, 2:325–330, 1993.

Patti and Höök, "Microbial adhesins recognizing extracellular matrix macromolecules." *Curr. Opin. Cell Biol.* 6:752–758, 1994.

Patti et al., "Critical Residues in the Ligand Binding Site of the *Staphylococcus aureus* Collagen-Binding Adhesin (MSCRAMM)," *J. Biol. Chem.*, 270:12005–12001, 1995.

Patti et al., "Identification and Biochemical Characterization of the Ligand Binding Domain of the Collagen Adhesin from *Staphylococcus aureus*," *Biochemistry*, 32:11428–11435, 1993.

Patti et al., "Molecular Characterization and Expression of a Gene Encoding a *Staphylococcus aureus* Collagen Adhesin," *J. Biol. Chem.*, 267:4766–4772, 1992.

Patti et al., "The *Staphylococcus aureus* Collagen Adhesin is a Virulence Determinant in Experimental Septic Arthritis," *Infect. and Immunity*, 62:152–161, 1994.

Patti, Allen, McGavin, and Höök, "MSCRAMM mediated adherence of microorganisms to host tissues." *Annu. Rev. Microbiol.* 48:585–617, 1994.

Perczel et al., *Proteins*, 13:57–69, 1992.

Pimm et al., *J. Cancer Res. Clin. Oncol.*, 118:367–370, 1992.

Porath et al., *Nature*, (London) 258:598–599, 1975.

Potts and Campbell, *Curr. Opin. Cell Biol.*, 6:648–655, 1994.

Pozzi et al., *Infect. Immun.*, 60:1902–1907, 1992.

Prokop and Bajpai, "Recombinant DNA Technology I" *Ann. N.Y. Acad. Sci., Vol.* 646, 1991.

Ramachandran and Reddi, "Biochemistry of Collagen," Plenum Press, New York, 1976.

Ramisse et al., "Passive local immunotherapy of experimental staphylococcal pneumonia with human intravenous immunoglobulin," *J. Inf. Dis.*, 168:1030–1033, 1993.

Ratlift et al., *Cancer Res.*, 47:1762–1766, 1987.

Ravindranath et al., "Immunopathologic features of *Staphylococcus aureus* endophthalmitis in the rat," *Invest. Ophth. Vis. Sci.* 36:2482–2491, 1995.

Riggs, In: *Current Protocols in Molecular Biology*, Ausubel et al., (Eds), Greene Associates/Wiley Interscience, NY, 1992.

Rozalska, Sakata, and Wadstrom, "*Staphylococcus aureus* fibronectin-binding proteins FnBPs: Identification of antigenic epitopes using polyclonal antibodies." *APMIS* 102:112–118, 1994.

Sambrook et al., "Molecular Cloning: A Laboratory Manual," 2nd Edition; Cold Spring Harbor Laboratory, Cold Spring Harbor, N.Y., 1989.

Sapatnekar et al., *J. Biomedical Afater. Res.*, 29:247–256, 1995.

Schneewind et al., *Science*, 268:103–106, 1995.

Segal, "Biochemical Calculations" 2nd Edition, John Wiley and Sons, New York, 1976.

Sela et al., "Protein F; An Adhesin of *Streptococcus pyogenes* Binds to Fibronectin via Two Distinct Domains," *Molec. Microbiol.*, 10: 1049–1055, 1993.

Semisotnov et al., *Biopolymers*, 31:119–128, 1991.

Shapiro, Berg, Austrian, Schroeder, Parcelis, Margolis, Adair, and Clemens, "Protective efficacy of polyvalent pneumococcal polysaccharide vaccine." *N. Engl. J. Med.* 325:1453–1460, 1991.

Sheagren, "Inflammation induced by *Staphylococcus aureus*," p. 829–840, In *Inflammation: Basic Principles and Clinical Correlates*, Gallin, Goldstein, and Snyderman (ed.), Raven Press, New York, 1988.

Sheagren, "*Staphylococcus aureus*: the persistent pathogen." *N. Engl. J. Med.* 310:1368–1373, 1437–1442, 1984.

Siber, "Pneumococcal disease: Prospects for a new generation of vaccines." *Science* 265:1385–1387, 1994.

Signas, Raucci, Jönsson, Lindgren, Anantharamaiah, Höök, and Lindberg, "Nucleotide sequence of the gene for a fibronectin binding protein from *Staphylococcus aureus*: Use of this peptide sequence in the synthesis of biologically active peptides." *Proc. Natl. Acad. Sci. USA.* 86:699–703, 1989.

Smith and Johnson, *Gene*, 67:31–40, 1988.

Smith, Krohn, Hermanson, Mallia, Gartner, Provenzano, Fujimoto, Goeke, Olson, and Klenk, "Measurement of protein using bicinchoninic acid." *Anal. Biochem.* 150:76–85, 1985.

Speziale et al., "Binding of Collagen to *Staphylococcus aureus* Cowan 1," *J. Bact.*, 1967:77–81, 1986.

Speziale et al., "Fibronectin Binding to a *Streptococcus pyogenes* Strain," *J. Bact.*, 157:420–427, 1984.

Speziale, Joh, Visai, Bozzini, House-Pompeo, Lindberg, and Höök, "A monoclonal antibody enhances ligand binding of fibronectin MSCRAMM (adhesin) from *S. dysgalactiae*." *J. Biol. Chem.* 271:1371–1378, 1996.

Spoerel, *Methods Enzymol.* 152:588–597, 1987.

Stevens et al., *J. Mol. Biol.*, 197:743–745, 1987.

Stinchcomb et al., *Nature*, 282:39, 1979.

Strong et al., "Isolation, Characterization and Synthesis of Peptides from Human Fibrinogen that Block the Staphylococcal Clumping Reaction and Construction of a Synthetic Clumping Particle," *Biochemistry,* 21:1414–1420, 1982.

Switalski et al., *J. Biol. Chem.,* 264:21080–21086, 1989.

Switalski et al., "Collagen Mediates Adhesion of *Streptococcus Mutans* to Human Dentin," *Infect. and Immun.,* 61:4119–4125, 1993.

Talay et al., "Fibronectin-Binding Protein of *Streptococcus pyogenes*: Sequence of the Binding Domain Involved in Adherence of Streptococci to Epithelial Cells," *Infect. Immun.,* 60:3837–3844, 1992.

Talay et al., *Mol. Microbiol.,* 13:531–539, 1994.

Talay, Valentin-Weigand, Jerlstrom, Timmis and Chhatwal. "Fibronectin-binding protein of *Streptococcus pyogenes*: sequence of the binding domain involved in adherence of streptococci to epithelial cells?" *Infect. Immun.* 60:3837–3844, 1992.

Tanford et al., *J. Am. Chem. Soc.,* 89:729–736, 1967.

Tang et al., *Nature,* 356:152–154, 1992.

Tempest et al. *Biotechnology* 9:266–273, 1991.

Titus et al., *J. Immunol.,* 138:4018–4022, 1987.

Tschemper et al., *Gene,* 10:157, 1980.

Tung and Knight, *Anal. Biochem.,* 48:153–163, 1972.

Tutt et al., *Eur. J. Immunol.,* 21:1351–1358, 1991.

Ulmer et al., "Heterologous Protection Against Influenza by Injection of DNA Encoding a Viral Protein," *Science,* 259:1745–1749, 1993.

Vanderrest and Garrone, *FASEB. J,* 5:2814–2823, 1991.

Van Duk et al., *Int. J. Cancer,* 43:344–349, 1989.

Vaudaux et al., "Use of Adhesion-Defective Mutants of *Staphylococcus aureus* to Define the Role of Specific Plasma Proteins in Promoting Bacterial Adhesion to Canine Arteriovenous Shunts," *Infect. Immun.,* 63:585–590, 1995.

Vaudaux, Pittet, Haeberli, Lerch, Morgenthaler, Proctor, Waldvogel, and Lew. "Fibronectin is more active than fibrin or fibrinogen in promoting *Staphylococcus aureus* adherence to inserted intravascular catheters." *J. Infect. Dis.* 160:865–875, 1993.

Venyaminov et al., *Eur. J. Biochem.,* 135:485–489, 1983.

Vuento and Vaheri, *Biochem. J.* 183:331–337, 1979.

Wagner et al., "Coupling of adenovirus to transferrin-polylysine/DNA complexes greatly enhances receptor-mediated gene delivery and expression of transfected genes," *Proc. Natl. Acad. Sci. USA,* 89(13):6099–6103, 1992.

Wallace, et al., *Vet. Immunol. Immunopath.,* 48:139–154, 1995.

Wang et al., *J. Exp. Med.,* 177:699, 1993.

Wang et al., *J. Immunol.,* 150:3022, 1993.

Wangsgard, Meixell, Dasgupta, and Blumenthal. "Activation and inhibition of phosphorylase kinase by monospecific antibodies raised against peptides from the regulatory domain of the gamma subunit." *J. Biol. Chem.* 271:21126–21133, 1996.

Welsh et al., *Biopolymers,* 22:821–831, 1983.

Whitton et al., *J. Virol.,* 67:(1)348–352, 1993.

Widders, et al., *Res. Vet. Sci.,* 58:75–81, 1995.

Williams et al., *J. Mol. Biol.,* 235:1302–1311, 1994.

Winter and Milstein, *Nature,* 349:293–299, 1991.

Wolf et al., *Compu. Appl. Biosci.,* 4(1):187–91, 1988.

Wong and Neumann, "Electric field mediated gene transfer," *Biochim. Biophys. Res. Commun.,* 107(2):584–587, 1982.

Woody, *In: Peptides, polypeptides, and proteins*, Blout, Bovey, Goodman, and Lotan, eds, Wiley, New York, N.Y., pp. 338–350, 1974.

Wu et al., *Biochemistry,* 32:1027 1–10276, 1993.

Young and Davis, "Efficient Isolation of Genes by Using Antibody Probes," *Proc. Natl. Acad. Sci. USA,* 80:1194–1198, 1983.

---

What is claimed is:

1. A method of generating an antibody that binds to a fibronectin binding domain of a fibronectin binding protein and inhibits binding of said fibronectin binding protein to fibronectin, comprising administering to a human or animal a pharmaceutical composition comprising an immunologically effective amount of a peptide of a fibronectin binding domain of a fibronectin binding protein that does not bind to fibronectin, wherein said peptide is selected from the group consisting of SEQ ID NOS: 12, 14–16, 21–53, 62–85, 88–102 and 105.

2. The method according to claim 1 wherein said pharmaceutical composition is prepared by:
   a) contacting a peptide with fibronectin under effective binding conditions and identifying a peptide that does not bind to fibronectin; and
   b) adding said peptide that does not bind to fibronectin to a pharmaceutically acceptable diluent to form said pharmaceutical composition.

3. The method according to claim 2 wherein a plurality of peptides are contacted with fibronectin under effective binding conditions, and at least one peptide that does not bind to fibronectin is identified.

4. The method according to claim 1 wherein the pharmaceutical composition is administered to a human or animal suspected of having, or at risk of developing, a microbial infection.

* * * * *

SEQUENCE LISTING (1) GENERAL INFORMATION:

(iii) NUMBER OF SEQUENCES: 105

(2) INFORMATION FOR SEQ ID NO: 1:

(i) SEQUENCE CHARACTERISTICS:
      (A) LENGTH: 6 amino acids
      (B) TYPE: amino acid
      (C) STRANDEDNESS: <Unknown>
      (D) TOPOLOGY: linear (ix) FEATURE:
      (A) NAME/KEY: Modified-site
      (B) LOCATION: 3..6
      (D) OTHER INFORMATION: /note= "X = any amino acid"

(xi) SEQUENCE DESCRIPTION: SEQ ID NO: 1:

Leu Pro Xaa Thr Gly Xaa
1             5

(2) INFORMATION FOR SEQ ID NO: 2:

(i) SEQUENCE CHARACTERISTICS:
      (A) LENGTH: 10 amino acids
      (B) TYPE: amino acid
      (C) STRANDEDNESS: <Unknown>
      (D) TOPOLOGY: linear (xi) SEQUENCE DESCRIPTION: SEQ ID NO: 2:

Glu Glu Asp Thr Glu Lys Asp Lys Pro Lys
1               5                   10

(2) INFORMATION FOR SEQ ID NO: 3:

(i) SEQUENCE CHARACTERISTICS:
        (A) LENGTH: 31 amino acids
        (B) TYPE: amino acid
        (C) STRANDEDNESS: <Unknown>
        (D) TOPOLOGY: linear (xi) SEQUENCE DESCRIPTION: SEQ ID NO: 3:

Ala Asp Val Val Glu Tyr Glu Glu Asp Thr Asn Pro Gly Gly Gln
1               5                   10                  15

Val Thr Thr Glu Ser Asn Leu Val Glu Phe Asp Glu Glu Ser Thr
                20                  25                  30

(2) INFORMATION FOR SEQ ID NO: 4:

(i) SEQUENCE CHARACTERISTICS:
        (A) LENGTH: 31 amino acids
        (B) TYPE: amino acid
        (C) STRANDEDNESS: <Unknown>
        (D) TOPOLOGY: linear (xi) SEQUENCE DESCRIPTION: SEQ ID NO: 4:

Ala Asp Val Val Glu Tyr Glu Glu Asp Thr Asn Pro Pro Gly Gln
1               5                   10                  15

Val Thr Thr Glu Ser Asn Leu Val Glu Phe Asp Glu Glu Ser Thr
                20                  25                  30

(2) INFORMATION FOR SEQ ID NO: 5:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 5:

Gln Asn Ser Gly Asn Gln Ser Phe Glu Glu Asp Thr Glu Glu Asp Lys
1               5                   10                      15

Pro Lys Tyr Glu Gln Gly Gly Asn Ile Val Asp Ile Asp Phe Asp Ser
                20                  25                  30

Val Pro Gln Ile His Gly
        35

(2) INFORMATION FOR SEQ ID NO: 6:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 6:

Gln Asn Ser Gly Asn Gln Ser Phe Glu Glu Asp Thr Glu Glu Asp Lys
1               5                   10                      15

Pro Lys Tyr Glu Gln Pro Gly Asn Ile Val Asp Ile Asp Phe Asp Ser
                20                  25                  30

Val Pro Gln Ile His Gly
        35

```
(2) INFORMATION FOR SEQ ID NO: 7:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 7:

Gln Asn Lys Gly Asn Gln Ser Phe Glu Glu Asp Thr Glu Lys Asp Lys
1               5                   10                  15

Pro Lys Tyr Glu His Gly Gly Asn Ile Ile Asp Ile Asp Phe Asp Ser
            20                  25                  30

Val Pro His Ile His Gly
            35

(2) INFORMATION FOR SEQ ID NO: 8:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 8:

Gln Asn Lys Gly Asn Gln Ser Phe Glu Glu Asp Thr Glu Lys Asp Lys
1               5                   10                  15

Pro Lys Tyr Glu His Pro Gly Asn Ile Ile Asp Ile Asp Phe Asp Ser
            20                  25                  30

Val Pro His Ile His Gly
            35

(2) INFORMATION FOR SEQ ID NO: 9:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 9:

Lys Pro Ser Tyr Gln Phe Gly Gly His Asn Ser Val Asp Phe Glu Glu
1               5                   10                  15

Asp Thr Leu Pro Lys
            20

(2) INFORMATION FOR SEQ ID NO: 10:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 10:

Lys Pro Ser Tyr Gln Phe Pro Gly His Asn Ser Val Asp Phe Glu Glu
1               5                   10                  15

Asp Thr Leu Pro Lys
            20
```

(2) INFORMATION FOR SEQ ID NO: 11:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (xi) SEQUENCE DESCRIPTION: SEQ ID NO: 11:

Gly Gln Asn Glu Gly Gln Gln Thr Ile Glu Glu Asp Thr Thr Pro Pro
1               5                   10                  15

Ile Val Pro (2) INFORMATION FOR SEQ ID NO: 12:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (xi) SEQUENCE DESCRIPTION: SEQ ID NO: 12:

Gly Gln Asn Glu Gly Gln Gln Thr Ile Pro Glu Asp Thr Thr Pro Pro
1               5                   10                  15

Ile Val Pro (2) INFORMATION FOR SEQ ID NO: 13:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (xi) SEQUENCE DESCRIPTION: SEQ ID NO: 13:

Lys Pro Ser Tyr Gln Phe Pro Gly His Asn Ser Val Asp Phe Glu Glu
1               5                   10                  15

Asp Thr Leu Pro Lys Val
            20

(2) INFORMATION FOR SEQ ID NO: 14:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 14:

Pro Pro Ser Tyr Gln Phe Gly Gly His Asn Ser Val Asp Phe Glu Glu
1               5                   10                  15

Asp Thr Leu Pro Lys
            20

(2) INFORMATION FOR SEQ ID NO: 15:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 15:

Lys Ala Ser Tyr Gln Phe Gly Gly His Asn Ser Val Asp Phe Glu Glu
1               5                   10                  15

Asp Thr Leu Pro Lys
            20

(2) INFORMATION FOR SEQ ID NO: 16:

(i) SEQUENCE CHARACTERISTICS:
            (A) LENGTH: 21 amino acids
            (B) TYPE: amino acid
            (C) STRANDEDNESS: <Unknown>
            (D) TOPOLOGY: linear (xi) SEQUENCE DESCRIPTION: SEQ ID NO: 16:

Lys Pro Pro Tyr Gln Phe Gly Gly His Asn Ser Val Asp Phe Glu Glu
1               5                   10                  15

Asp Thr Leu Pro Lys
            20

(2) INFORMATION FOR SEQ ID NO: 17:

(i) SEQUENCE CHARACTERISTICS:
            (A) LENGTH: 21 amino acids
            (B) TYPE: amino acid
            (C) STRANDEDNESS: <Unknown>
            (D) TOPOLOGY: linear (xi) SEQUENCE DESCRIPTION: SEQ ID NO: 17:

Lys Pro Ser Pro Gln Phe Gly Gly His Asn Ser Val Asp Phe Glu Glu
1               5                   10                  15

Asp Thr Leu Pro Lys
            20

(2) INFORMATION FOR SEQ ID NO: 18:

(i) SEQUENCE CHARACTERISTICS:
            (A) LENGTH: 21 amino acids
            (B) TYPE: amino acid
            (C) STRANDEDNESS: <Unknown>
            (D) TOPOLOGY: linear (xi) SEQUENCE DESCRIPTION: SEQ ID NO: 18:

Lys Pro Ser Tyr Pro Phe Gly Gly His Asn Ser Val Asp Phe Glu Glu
1               5                   10                  15

Asp Thr Leu Pro Lys
            20

(2) INFORMATION FOR SEQ ID NO: 19:

(i) SEQUENCE CHARACTERISTICS:
            (A) LENGTH: 21 amino acids
            (B) TYPE: amino acid
            (C) STRANDEDNESS: <Unknown>
            (D) TOPOLOGY: linear (xi) SEQUENCE DESCRIPTION: SEQ ID NO: 19:

Lys Pro Ser Tyr Gln Pro Gly Gly His Asn Ser Val Asp Phe Glu Glu
1               5                   10                  15

Asp Thr Leu Pro Lys
            20

-continued (2) INFORMATION FOR SEQ ID NO: 20:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 20:

```
Lys Pro Ser Tyr Gln Phe Gly Pro His Asn Ser Val Asp Phe Glu Glu
1               5                   10                  15

Asp Thr Leu Pro Lys
            20
```

(2) INFORMATION FOR SEQ ID NO: 21:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 21:

```
Lys Pro Ser Tyr Gln Phe Gly Gly Pro Asn Ser Val Asp Phe Glu Glu
1               5                   10                  15

Asp Thr Leu Pro Lys
            20
```

(2) INFORMATION FOR SEQ ID NO: 22:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 22:

```
Lys Pro Ser Tyr Gln Phe Gly Gly His Pro Ser Val Asp Phe Glu Glu
1               5                   10                  15

Asp Thr Leu Pro Lys
            20
```

(2) INFORMATION FOR SEQ ID NO: 23:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 23:

```
Lys Pro Ser Tyr Gln Phe Gly Gly His Asn Pro Val Asp Phe Glu Glu
1               5                   10                  15

Asp Thr Leu Pro Lys
            20
```

(2) INFORMATION FOR SEQ ID NO: 24:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 24:

Lys Pro Ser Tyr Gln Phe Gly Gly His Asn Ser Pro Asp Phe Glu Glu
1               5                   10                  15

Asp Thr Leu Pro Lys
            20

(2) INFORMATION FOR SEQ ID NO: 25:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 25:

Lys Pro Ser Tyr Gln Phe Gly Gly His Asn Ser Val Pro Phe Glu Glu
1               5                   10                  15

Asp Thr Leu Pro Lys
            20

(2) INFORMATION FOR SEQ ID NO: 26:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 26:

Lys Pro Ser Tyr Gln Phe Gly Gly His Asn Ser Val Asp Pro Glu Glu
1               5                   10                  15

Asp Thr Leu Pro Lys
            20

(2) INFORMATION FOR SEQ ID NO: 27:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 27:

Lys Pro Ser Tyr Gln Phe Gly Gly His Asn Ser Val Asp Phe Pro Glu
1               5                   10                  15

Asp Thr Leu Pro Lys
            20

(2) INFORMATION FOR SEQ ID NO: 28:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 28:

Lys Pro Ser Tyr Gln Phe Gly Gly His Asn Ser Val Asp Phe Glu Pro
1               5                   10                  15

Asp Thr Leu Pro Lys
            20

```
(2) INFORMATION FOR SEQ ID NO: 29:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 29:

Lys Pro Ser Tyr Gln Phe Gly Gly His Asn Ser Val Asp Phe Glu Glu
1               5                   10                  15

Pro Thr Leu Pro Lys
            20

(2) INFORMATION FOR SEQ ID NO: 30:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 30:

Lys Pro Ser Tyr Gln Phe Gly Gly His Asn Ser Val Asp Phe Glu Glu
1               5                   10                  15

Asp Pro Leu Pro Lys
            20

(2) INFORMATION FOR SEQ ID NO: 31:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 31:

Lys Pro Ser Tyr Gln Phe Gly Gly His Asn Ser Val Asp Phe Glu Glu
1               5                   10                  15

Asp Thr Pro Pro Lys
            20

(2) INFORMATION FOR SEQ ID NO: 32:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 32:

Lys Pro Ser Tyr Gln Phe Gly Gly His Asn Ser Val Asp Phe Glu Glu
1               5                   10                  15

Asp Thr Leu Ala Lys
            20

(2) INFORMATION FOR SEQ ID NO: 33:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear
```

(xi) SEQUENCE DESCRIPTION: SEQ ID NO: 33:

Lys Pro Ser Tyr Gln Phe Gly Gly His Asn Ser Val Asp Phe Glu Glu
1               5                   10                  15

Asp Thr Leu Pro Pro
            20

(2) INFORMATION FOR SEQ ID NO: 34:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (xi) SEQUENCE DESCRIPTION: SEQ ID NO: 34:

Pro Ala Ser Tyr Gln Phe Pro Pro His Asn Ser Val Asp Phe Glu Glu
1               5                   10                  15

Asp Thr Leu Pro Lys
            20

(2) INFORMATION FOR SEQ ID NO: 35:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 35:

Gln Asn Ser Gly Asn Gln Ser Pro Glu Glu Asp Thr Glu Glu Asp Lys
1               5                   10                  15

Pro Lys Tyr Glu Gln Gly Gly Asn Ile Val Asp Ile Asp Phe Asp Ser
            20                  25                  30

Val Pro Gln Ile His Gly
        35

(2) INFORMATION FOR SEQ ID NO: 36:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 36:

Gln Asn Ser Gly Asn Gln Ser Phe Pro Glu Asp Thr Glu Glu Asp Lys
1               5                   10                  15

Pro Lys Tyr Glu Gln Gly Gly Asn Ile Val Asp Ile Asp Phe Asp Ser
            20                  25                  30

Val Pro Gln Ile His Gly
        35

(2) INFORMATION FOR SEQ ID NO: 37:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 37:

Gln Asn Ser Gly Asn Gln Ser Phe Glu Pro Asp Thr Glu Glu Asp Lys
1               5                   10                  15

Pro Lys Tyr Glu Gln Gly Gly Asn Ile Val Asp Ile Asp Phe Asp Ser
            20                  25                  30

Val Pro Gln Ile His Gly
        35

(2) INFORMATION FOR SEQ ID NO: 38:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 38:

Gln Asn Ser Gly Asn Gln Ser Phe Glu Glu Pro Thr Glu Glu Asp Lys
1               5                   10                  15

Pro Lys Tyr Glu Gln Gly Gly Asn Ile Val Asp Ile Asp Phe Asp Ser
            20                  25                  30

Val Pro Gln Ile His Gly
        35

(2) INFORMATION FOR SEQ ID NO: 39:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 39:

Gln Asn Ser Gly Asn Gln Ser Phe Glu Glu Asp Pro Glu Glu Asp Lys
1               5                   10                  15

Pro Lys Tyr Glu Gln Gly Gly Asn Ile Val Asp Ile Asp Phe Asp Ser
            20                  25                  30

Val Pro Gln Ile His Gly
        35

(2) INFORMATION FOR SEQ ID NO: 40:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 40:

Gln Asn Ser Gly Asn Gln Ser Phe Glu Glu Asp Thr Pro Glu Asp Lys
1               5                   10                  15

Pro Lys Tyr Glu Gln Gly Gly Asn Ile Val Asp Ile Asp Phe Asp Ser
            20                  25                  30

Val Pro Gln Ile His Gly
        35

(2) INFORMATION FOR SEQ ID NO: 41:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 41:

Gln Asn Ser Gly Asn Gln Ser Phe Glu Glu Asp Thr Glu Pro Asp Lys
1               5                   10                  15

Pro Lys Tyr Glu Gln Gly Gly Asn Ile Val Asp Ile Asp Phe Asp Ser
                20                  25                  30

Val Pro Gln Ile His Gly
        35

(2) INFORMATION FOR SEQ ID NO: 42:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 42:

Gln Asn Ser Gly Asn Gln Ser Phe Glu Glu Asp Thr Glu Glu Pro Lys
1               5                   10                  15

Pro Lys Tyr Glu Gln Gly Gly Asn Ile Val Asp Ile Asp Phe Asp Ser
                20                  25                  30

Val Pro Gln Ile His Gly
        35

(2) INFORMATION FOR SEQ ID NO: 43:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 43:

Gln Asn Ser Gly Asn Gln Ser Phe Glu Glu Asp Thr Glu Glu Asp Lys
1               5                   10                  15

Pro Lys Tyr Glu Gln Gly Pro Asn Ile Val Asp Ile Asp Phe Asp Ser
                20                  25                  30

Val Pro Gln Ile His Gly
        35

(2) INFORMATION FOR SEQ ID NO: 44:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 44:

Gln Asn Ser Gly Asn Gln Ser Phe Pro Pro Asp Thr Glu Glu Asp Lys
1               5                   10                  15

Pro Lys Tyr Glu Gln Pro Pro Asn Ile Val Asp Ile Asp Phe Asp Ser
                20                  25                  30

Val Pro Gln Ile His Gly
        35

(2) INFORMATION FOR SEQ ID NO: 45:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 45:

Gln Asn Lys Gly Asn Gln Ser Pro Glu Asp Thr Glu Lys Asp Lys
1               5                   10                  15

Pro Lys Tyr Glu His Gly Gly Asn Ile Ile Asp Ile Asp Phe Asp Ser
            20                  25                  30

Val Pro His Ile His Gly
        35

(2) INFORMATION FOR SEQ ID NO: 46:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 46:

Gln Asn Lys Gly Asn Gln Ser Phe Pro Glu Asp Thr Glu Lys Asp Lys
1               5                   10                  15

Pro Lys Tyr Glu His Gly Gly Asn Ile Ile Asp Ile Asp Phe Asp Ser
            20                  25                  30

Val Pro His Ile His Gly
        35

(2) INFORMATION FOR SEQ ID NO: 47:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 47:

Gln Asn Lys Gly Asn Gln Ser Phe Glu Pro Asp Thr Glu Lys Asp Lys
1               5                   10                  15

Pro Lys Tyr Glu His Gly Gly Asn Ile Ile Asp Ile Asp Phe Asp Ser
            20                  25                  30

Val Pro His Ile His Gly
        35

(2) INFORMATION FOR SEQ ID NO: 48:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 48:

Gln Asn Lys Gly Asn Gln Ser Phe Glu Glu Pro Thr Glu Lys Asp Lys
1               5                   10                  15

Pro Lys Tyr Glu His Gly Gly Asn Ile Ile Asp Ile Asp Phe Asp Ser
            20                  25                  30

Val Pro His Ile His Gly
        35

(2) INFORMATION FOR SEQ ID NO: 49:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 49:

Gln Asn Lys Gly Asn Gln Ser Phe Glu Glu Asp Thr Glu Lys Asp Lys
1               5                   10                  15
Pro Lys Tyr Glu His Gly Pro Asn Ile Ile Asp Ile Asp Phe Asp Ser
            20                  25                  30
Val Pro His Ile His Gly
        35

(2) INFORMATION FOR SEQ ID NO: 50:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (xi) SEQUENCE DESCRIPTION: SEQ ID NO: 50:

Gln Asn Lys Gly Asn Gln Ser Phe Pro Pro Asp Thr Glu Lys Asp Lys
1               5                   10                  15
Pro Lys Tyr Glu His Pro Pro Asn Ile Ile Asp Ile Asp Phe Asp Ser
            20                  25                  30
Val Pro His Ile His Gly
        35

(2) INFORMATION FOR SEQ ID NO: 51:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (xi) SEQUENCE DESCRIPTION: SEQ ID NO: 51:

Gly Gln Asn Glu Gly Gln Gln Thr Ile Glu Pro Asp Thr Thr Pro Pro
1               5                   10                  15
Ile Val Pro (2) INFORMATION FOR SEQ ID NO: 52:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (xi) SEQUENCE DESCRIPTION: SEQ ID NO: 52:

Gly Gln Asn Glu Gly Gln Gln Thr Ile Glu Glu Pro Thr Thr Pro Pro
1               5                   10                  15
Ile Val Pro (2) INFORMATION FOR SEQ ID NO: 53:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (xi) SEQUENCE DESCRIPTION: SEQ ID NO: 53:

Gly Gln Asn Glu Gly Gln Gln Thr Pro Glu Glu Asp Thr Thr Pro Pro
1               5                   10                  15
Ile Val Pro (2) INFORMATION FOR SEQ ID NO: 54:

(i) SEQUENCE CHARACTERISTICS:
        (A) LENGTH: 31 amino acids
        (B) TYPE: amino acid
        (C) STRANDEDNESS: <Unknown>
        (D) TOPOLOGY: linear (xi) SEQUENCE DESCRIPTION: SEQ ID NO: 54:

```
Ala Asp Val Val Glu Tyr Glu Glu Asp Thr Asn Pro Gly Pro Gly Gln
 1               5                  10                  15
Val Thr Thr Glu Ser Asn Leu Val Glu Phe Asp Glu Glu Ser Thr
                20                  25                  30
```

(2) INFORMATION FOR SEQ ID NO: 55:

(i) SEQUENCE CHARACTERISTICS:
        (A) LENGTH: 31 amino acids
        (B) TYPE: amino acid
        (C) STRANDEDNESS: <Unknown>
        (D) TOPOLOGY: linear (xi) SEQUENCE DESCRIPTION: SEQ ID NO: 55:

```
Ala Asp Val Val Glu Tyr Pro Pro Asp Thr Asn Pro Pro Gly Gln
 1               5                  10                  15
Val Thr Thr Glu Ser Asn Leu Val Glu Phe Asp Glu Glu Ser Thr
                20                  25                  30
```

(2) INFORMATION FOR SEQ ID NO: 56:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: linear (xi) SEQUENCE DESCRIPTION: SEQ ID NO: 56:

```
Gln Asn Ser Gly Asn Gln Ser Phe Glu Glu Asp Thr Glu Glu Asp Lys
 1               5                  10                  15
Pro Lys Tyr Glu Gln Gly Gly Asn Ile Val Asp Ile Asp Phe Ser Asp
                20                  25                  30
Ser Val Pro Gln Ile His Gly
                35
```

(2) INFORMATION FOR SEQ ID NO: 57:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: linear (xi) SEQUENCE DESCRIPTION: SEQ ID NO: 57:

```
Gln Asn Ser Gly Asn Gln Ser Phe Glu Glu Asp Thr Glu Glu Asp Lys
 1               5                  10                  15
Pro Lys Tyr Glu Gln Pro Gly Asn Ile Val Asp Ile Asp Phe Ser Asp
                20                  25                  30
Ser Val Pro Gln Ile His Gly
                35
```

```
(2) INFORMATION FOR SEQ ID NO: 58:

(i) SEQUENCE CHARACTERISTICS:
        (A) LENGTH: 36 amino acids
        (B) TYPE: amino acid
        (C) STRANDEDNESS: <Unknown>
        (D) TOPOLOGY: linear (xi) SEQUENCE DESCRIPTION: SEQ ID NO: 58:

Gln Asn Lys Gly Asn Gln Ser Phe Glu Glu Asp Thr Glu Lys Asp Lys
1               5                   10                  15

Tyr Glu His Gly Gly Asn Ile Ile Asp Ile Asp Phe Asp Ser Val Pro
            20                  25                  30

His Ile His Gly
        35

(2) INFORMATION FOR SEQ ID NO: 59:

(i) SEQUENCE CHARACTERISTICS:
        (A) LENGTH: 36 amino acids
        (B) TYPE: amino acid
        (C) STRANDEDNESS: <Unknown>
        (D) TOPOLOGY: linear (xi) SEQUENCE DESCRIPTION: SEQ ID NO: 59:

Gln Asn Lys Gly Asn Gln Ser Phe Glu Glu Asp Thr Glu Lys Asp Lys
1               5                   10                  15

Tyr Glu His Pro Gly Asn Ile Ile Asp Ile Asp Phe Asp Ser Val Pro
            20                  25                  30

His Ile His Gly
        35

(2) INFORMATION FOR SEQ ID NO: 60:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 60:

Gln Gly Gly Asn Ile Val Asp Ile Asp Phe Asp Ser Val Pro
1               5                   10

(2) INFORMATION FOR SEQ ID NO: 61:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 61:

Gln Phe Gly Gly His Asn Ser Val Asp Phe Glu Glu Asp Thr
1               5                   10

(2) INFORMATION FOR SEQ ID NO: 62:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear
```

(xi) SEQUENCE DESCRIPTION: SEQ ID NO: 62:

Ser Phe Glu Glu Asp Thr Glu Lys Asp Lys Pro Lys
1               5                   10

(2) INFORMATION FOR SEQ ID NO: 63:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 63:

Gln Asn Ser Gly Asn Gln Ser Phe Glu Glu
1               5                   10

(2) INFORMATION FOR SEQ ID NO: 64:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 64:

Ser Gly Asn Gln Ser Phe Glu Glu Asp Thr
1               5                   10

(2) INFORMATION FOR SEQ ID NO: 65:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 65:

Asn Gln Ser Phe Glu Glu Asp Thr Glu Glu
1               5                   10

(2) INFORMATION FOR SEQ ID NO: 66:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 66:

Ser Phe Glu Glu Asp Thr Glu Glu Asp Lys
1               5                   10

(2) INFORMATION FOR SEQ ID NO: 67:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 67:

Glu Glu Asp Thr Glu Glu Asp Lys Pro Lys
1               5                   10

(2) INFORMATION FOR SEQ ID NO: 68:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 68:

```
Asp Thr Glu Glu Asp Lys Pro Lys Tyr Glu
1               5                   10
```

(2) INFORMATION FOR SEQ ID NO: 69:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 69:

```
Glu Glu Asp Lys Pro Lys Tyr Glu Gln Gly
1               5                   10
```

(2) INFORMATION FOR SEQ ID NO: 70:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 70:

```
Asp Lys Pro Lys Tyr Glu Gln Gly Gly Asn
1               5                   10
```

(2) INFORMATION FOR SEQ ID NO: 71:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 71:

```
Pro Lys Tyr Glu Gln Gly Gly Asn Ile Val
1               5                   10
```

(2) INFORMATION FOR SEQ ID NO: 72:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 72:

```
Tyr Glu Gln Gly Gly Asn Ile Val Asp Ile
1               5                   10
```

(2) INFORMATION FOR SEQ ID NO: 73:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear

```
    (xi) SEQUENCE DESCRIPTION: SEQ ID NO: 73:

Gln Gly Gly Asn Ile Val Asp Ile Asp Phe
1               5                   10

(2) INFORMATION FOR SEQ ID NO: 74:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 74:

Gly Asn Ile Val Asp Ile Asp Phe Asp Ser
1               5                   10

(2) INFORMATION FOR SEQ ID NO: 75:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 75:

Ile Val Asp Ile Asp Phe Asp Ser Val Pro
1               5                   10

(2) INFORMATION FOR SEQ ID NO: 76:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 76:

Asp Ile Asp Phe Asp Ser Val Pro Gln Ile
1               5                   10

(2) INFORMATION FOR SEQ ID NO: 77:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 77:

Asp Phe Asp Ser Val Pro Gln Ile His Gly
1               5                   10

(2) INFORMATION FOR SEQ ID NO: 78:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 78:

Asp Ser Val Pro Gln Ile His Gly Gln Asn
1               5                   10
```

```
(2) INFORMATION FOR SEQ ID NO: 79:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 79:

Val Pro Gln Ile His Gly Gln Asn Lys Gly
1               5                   10

(2) INFORMATION FOR SEQ ID NO: 80:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 80:

Gln Ile His Gly Gln Asn Lys Gly Asn Gln
1               5                   10

(2) INFORMATION FOR SEQ ID NO: 81:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 81:

His Gly Gln Asn Lys Gly Asn Gln Ser Phe
1               5                   10

(2) INFORMATION FOR SEQ ID NO: 82:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 82:

Gln Asn Lys Gly Asn Gln Ser Phe Glu Glu
1               5                   10

(2) INFORMATION FOR SEQ ID NO: 83:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 83:

Lys Gly Asn Gln Ser Phe Glu Glu Asp Thr
1               5                   10

(2) INFORMATION FOR SEQ ID NO: 84:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear
```

```
    (xi) SEQUENCE DESCRIPTION: SEQ ID NO: 84:

Asn Gln Ser Phe Glu Glu Asp Thr Glu Lys
1               5                   10

(2) INFORMATION FOR SEQ ID NO: 85:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 85:

Ser Phe Glu Glu Asp Thr Glu Lys Asp Lys
1               5                   10

(2) INFORMATION FOR SEQ ID NO: 86:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (xi) SEQUENCE DESCRIPTION: SEQ ID NO: 86:

Val Asp Phe Glu Glu Asp Thr Leu Pro Lys Val
1               5                   10

(2) INFORMATION FOR SEQ ID NO: 87:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (xi) SEQUENCE DESCRIPTION: SEQ ID NO: 87:

Phe Glu Glu Asp Thr
1               5

(2) INFORMATION FOR SEQ ID NO: 88:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 88:

Phe Asn Lys His Thr Glu Ile Ile Glu Glu
1               5                   10

(2) INFORMATION FOR SEQ ID NO: 89:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 89:

Lys His Thr Glu Ile Ile Glu Glu Asp Thr
1               5                   10
```

(2) INFORMATION FOR SEQ ID NO: 90:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 90:

Thr Glu Ile Ile Glu Glu Asp Thr Asn Lys
1               5                   10

(2) INFORMATION FOR SEQ ID NO: 91:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 91:

Ile Ile Glu Glu Asp Thr Asn Lys Asp Lys
1               5                   10

(2) INFORMATION FOR SEQ ID NO: 92:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 92:

Glu Glu Asp Thr Asn Lys Asp Lys Pro Ser
1               5                   10

(2) INFORMATION FOR SEQ ID NO: 93:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 93:

Asp Thr Asn Lys Asp Lys Pro Ser Tyr Gln
1               5                   10

(2) INFORMATION FOR SEQ ID NO: 94:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 94:

Asn Lys Asp Lys Pro Ser Tyr Gln Phe Gly
1               5                   10

(2) INFORMATION FOR SEQ ID NO: 95:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 95:

Asp Lys Pro Ser Tyr Gln Phe Gly Gly His
1               5                   10

(2) INFORMATION FOR SEQ ID NO: 96:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 96:

Pro Ser Tyr Gln Phe Gly Gly His Asn Ser
1               5                   10

(2) INFORMATION FOR SEQ ID NO: 97:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 97:

Tyr Gln Phe Gly Gly His Asn Ser Val Asp
1               5                   10

(2) INFORMATION FOR SEQ ID NO: 98:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 98:

Phe Gly Gly His Asn Ser Val Asp Phe Glu
1               5                   10

(2) INFORMATION FOR SEQ ID NO: 99:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 99:

Gly His Asn Ser Val Asp Phe Glu Glu Asp
1               5                   10

(2) INFORMATION FOR SEQ ID NO: 100:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 100:

Asn Ser Val Asp Phe Glu Glu Asp Thr Leu
1               5                   10

(2) INFORMATION FOR SEQ ID NO: 101:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 101:

```
Val Asp Phe Glu Glu Asp Thr Leu Pro Lys
1               5                   10
```

(2) INFORMATION FOR SEQ ID NO: 102:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 102:

```
Asp Phe Glu Glu Asp Thr Leu Pro Lys Val
1               5                   10
```

(2) INFORMATION FOR SEQ ID NO: 103:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 103:

```
His Gly Gly Asn Ile Ile Asp Ile Asp Phe Asp Ser Val Pro
1               5                   10
```

(2) INFORMATION FOR SEQ ID NO: 104:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (xi) SEQUENCE DESCRIPTION: SEQ ID NO: 104:

```
Ser Val Asp Phe Glu Glu Asp Thr
1               5
```

(2) INFORMATION FOR SEQ ID NO: 105:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 105:

```
Ser Phe Glu Glu Asp Thr Glu Glu Asp Lys Pro Lys Tyr Glu
1               5                   10
```